(12) United States Patent
Elmann et al.

(10) Patent No.: US 11,752,125 B2
(45) Date of Patent: Sep. 12, 2023

(54) **ANTI-NEUROINFLAMMATORY AND PROTECTIVE COMPOUNDS IN *ACHILLEA FRAGRANTISSIMA***

(71) Applicant: THE STATE OF ISRAEL MINISTRY OF AGRICULTURE & RURAL DEVELOPMENT, ARGICULTURAL RESEARCH ORGANIZATION, (ARO) (VOLCANI CENTER), Rishon Le Zion (IL)

(72) Inventors: Anat Elmann, Rehovot (IL); Rivka Ofir, Moshav Hazeva (IL); Yoel Kashman, Tel Aviv (IL)

(73) Assignee: THE STATE OF ISRAEL MINISTRY OF AGRICULTURE & RURAL DEVELOPMENT, AGRICULTURAL RESEARCH ORGANIZATION, Rishon Lezion (IL)

( * ) Notice: Subject to any disclaimer, the term of this patent is extended or adjusted under 35 U.S.C. 154(b) by 0 days.

(21) Appl. No.: 15/039,429

(22) PCT Filed: Nov. 26, 2014

(86) PCT No.: PCT/IB2014/066353
§ 371 (c)(1),
(2) Date: May 26, 2016

(87) PCT Pub. No.: WO2015/079390
PCT Pub. Date: Jun. 4, 2015

(65) Prior Publication Data
US 2017/0020842 A1    Jan. 26, 2017

Related U.S. Application Data

(60) Provisional application No. 62/077,973, filed on Nov. 11, 2014, provisional application No. 61/908,762, filed on Nov. 26, 2013.

(51) Int. Cl.
*A61K 31/352* (2006.01)
*A61K 36/28* (2006.01)
*A61K 31/343* (2006.01)

(52) U.S. Cl.
CPC .......... *A61K 31/352* (2013.01); *A61K 31/343* (2013.01); *A61K 36/28* (2013.01)

(58) Field of Classification Search
None
See application file for complete search history.

(56) References Cited

U.S. PATENT DOCUMENTS

| 8,124,936 B1 | 2/2012 | Lagna |
| 2005/0156111 A1 | 7/2005 | Racca et al. |
| 2006/0208190 A1 | 9/2006 | Wood |

FOREIGN PATENT DOCUMENTS

EP    0973019    1/2000

OTHER PUBLICATIONS

Keim et al.,Antioxidant and cyclooxygenase inhibitory phenolic compounds from Ocimum sanctum Linn, 2000, Phytomedicine, vol. 7 (1), pp. 7-13.*
Elmann, Anat. et al. "Extract of Achillea Fragrantissima Downreguiates ROS Production and Protects Astrocytes from Oxidative-Stress-Induced Cell Death". Neurodegenerative Diseases—Processes, Prevention. Protection and Monitoring, InTech, Dec. 9, 2011. Crossref, doi: 10.5772/32398. (Year: 2011)*
Chauhan et al. "Oxidative Stress in Alzheimer's Disease". Pathophysiology. 2006; 13:195-208. (Year: 2006).*
Disadee et al. "Flavonol 3-O-robinobiosides and 3-O-(2"-O-alpha-rhamnopyranosyl)-robinobiosides from Sesuvium portulacastrum". Tetrahedron. 2011; 67:4221-4226. (Year: 2011).*
Galasko et al. "Antioxidants for Alzheimer Disease: A Randomized Clinical Trial with Cerebrospinal Fluid Biomarker Measures". Arch Neurol. 2012; 69(7):836-841. Published Online Mar. 19, 2012. (Year: 2012).*
Anat Elmann et al: "3,5,4,' Trihydroxy-6,7,3'-Trimethoxyflavone Prtects Astrocytes Against Oxidative Stress via Interference With Cell Signaling and by Reducing the Levels of Intracellular Reactive Oxygen Species", Neurochemistry International., vol. 78, Sep. 10, 2014 (Sep. 10, 2014), pp. 67-75, XP055309872, GB ISSN: 019-0186, DOI: 2014.09.003.
Consolacion Y. Ragasa et al: "Monoterpene 14 Glycoside and Flavonoids From Blumea Lacera", Natural Medicines—Shoyakugaku Zasshi Vo. 61, No. 4, Jul. 19, 2007 pp. 474-475, XP55309893, JP ISSN: 1340-3443,DOI: 10.1007/S11418-007-0180-5.
Neuroinflammatory effects of the extract of Achillea fragrantissima, Elmann et al. BMC Complementary and Alternative Medicine 2011, 11:98, doi: 10.1186/1472-6882-11-98 http://www.biomedcentral.com/1472-6882/11/98 Anat Elmann, Sharon Mordechay, Hilla Erlank, Alona Telerman, Miriam Rindner and Rivka Ofir, Nov. 30, 2011.
The sesquiterpene lactones from achillea fragrantissima, I. Achillolide A and B, two nvel germacranolides, Tetrahedron 1987, vol. 43, Issue 18, doi: 10.1016/S0040-4020(01) 83452-9 Segal Ruth, Dor Akiva, Duddeck Helmut, Snatzke G?nther, Rosenbaum Doris, Kajt?r M?rton, Dec. 31, 1987.

* cited by examiner

*Primary Examiner* — Leslie A. Royds Draper
(74) *Attorney, Agent, or Firm* — Vorys, Sater, Seymour and Pease LLP; Anthony P. Venturino; Maryellen Feehery Hank

(57) ABSTRACT

The invention relates to 3,5,4'-trihydroxy-6,7,3'-trimethoxyflavone (TIF) and achillolid A in prevention or treatment of Alzheimer's disease as well as other neurodegenerative diseases such as Parkinson's disease, Amyotrophic Lateral Sclerosis (ALS), ischemia, immunodeficiency virus-1 (HTV-1)-associated dementia, Lewy body associated dementia, traumatic brain injury (TBI), glioma, epilepsy. Huntington's disease, multiple sclerosis, glaucoma and schizophrenia where neuroinflammation, oxidative stress, glutamate toxicity and amyloid beta toxicity are part of the pathophysiology.

3 Claims, 39 Drawing Sheets

A.

B.

C.

ANTI-NEUROINFLAMMATORY AND PROTECTIVE COMPOUNDS IN *ACHILLEA FRAGRANTISSIMA*

FIELD OF THE INVENTION

This invention is in the field of neurodegenerative conditions.

DESCRIPTION OF THE STATE OF THE ART

The elevation in life span of the population in the western world caused an elevated frequency of neurodegenerative diseases, like Alzheimer's and Parkinson's disease. These diseases have multifactorial pathogenesis, and in most of them, a massive neuronal cell death occurs as a consequence of an uncontrolled neuroinflammatory response as well as oxidative stress. These processes play a pivotal role in the initiation and progression of various neurodegenerative diseases and involves the activation of two main cell types in the brain—astrocytes and microglia. These cells can produce proinflammatory cytokines (such as TNFα) and cytotoxic agents, leading to exaggeration of the disease processes.

Neuroinflammation, oxidative stress, glutamate toxicity and amyloid beta toxicity are involved in the pathogenesis of Alzheimer's diseases and other neurodegenerative conditions.

SUMMARY OF THE INVENTION

In the present invention, inventors have purified from the desert plant *Achillea fragrantissima* (Af) two compounds: (1) an anti-neuroinflammatory and a protective compound determined by spectroscopic methods to be the sesquiterpene lactone achillolide A (AcA). AcA showed anti-inflammatory effects on microglial cells and splenocytes, and protective activity on oxidative stress-afflicted cells. AcA also protected cultured astrocytes and neurons from induced cell death via interference with cell signaling. AcA also protected cultured neurons from amyloid beta and glutamate-induced neuronal cell death.

(2) A protective compound determined by spectroscopic methods to be 3,5,4'-trihydroxy-6,7,3'-trimethoxyflavone (TTF). TTF showed anti-inflammatory effects in microglial cells, anti-oxidative effects in astrocytes, and protective activity on oxidative stress-afflicted cells. TTF protected neuronal cells from amyloid beta and glutamate cytotoxicity. TTF also protected cultured astrocytes and neurons from induced cell death via interference with cell signaling.

There is no evidence that TTF was present in extracts of Af, even if these extracts showed biological activity. The effects of TTF in any biological system have not been studied previously, and this is the first disclosure to characterize the anti-oxidant, anti-inflammatory, and protective effects of this compound against oxidative stress, glutamate and amyloid beta toxicity in the context of neurodegenerative diseases. This is also the first study that demonstrates that TTF can interfere with cell signaling events.

The present invention relates to a composition comprising 3,5,4'-trihydroxy-6,7,3'-trimethoxyflavone (TIF), for use in treating a mammal suffering from or susceptible to a neurodegenerative condition.

The present invention further relates to the composition above, wherein said neurodegenerative condition comprising death of neurons.

The present invention further relates to the composition above, wherein said neurodegenerative condition is selected from Alzheimer's disease, Parkinson's disease, Amyotrophic Lateral Sclerosis (ALS), ischemia, Huntingtons disease, schizophrenia, immunodeficiency virus-1 (HIV-1)-associated dementia, Lewy body associated dementia, traumatic brain injury (TBI), glioma, glaucoma, multiple sclerosis and epilepsy.

The present invention relates to a composition comprising TTF, for use in treating a mammal suffering from or susceptible to a disease which can be improved or prevented by affecting neuroinflammation.

The present invention further relates to the composition above, wherein said affecting is inhibiting secretion of a cytokine selected from a group consisting of: IL-6 and IL-1β.

The present invention relates to a composition comprising TTF, for use in treating a mammal suffering from or susceptible to a disease which can be improved or prevented by affecting a condition selected from a group consisting of: neuronal oxidative stress and astrocytic oxidative stress.

The present invention relates to a composition comprising TTF, for use in treating a mammal suffering from or susceptible to a disease which can be improved or prevented by affecting oxidative stress in brain.

The present invention further relates to the composition above, wherein said affecting further comprising inhibiting phosphorylation of a factor selected from a group consisting of: extracellular signal regulated kinase (ERK) 1/2, mitogen activated protein kinase kinase (MEK1), stress-activated protein kinase/c-Jun N-terminal kinase (SAPK/JNK) and cyclic AMP response element-binding protein (CREB).

The present invention further relates to the composition above, wherein said affecting is reducing the levels of reactive oxygen species (ROS).

The present invention further relates to the composition in the preceding paragraph, wherein said ROS are induced by $H_2O_2$, amyloid beta or glutamate.

The present invention relates to a composition comprising TTF, for use in treating a mammal suffering from or susceptible to a disease which can be improved or prevented by affecting glutamate toxicity.

The present invention relates to a composition comprising TTF, for use in treating a mammal suffering from or susceptible to a disease which can be improved or prevented by affecting amyloid beta toxicity.

The present invention relates to a composition comprising TTF, for use in treating a mammal suffering from or susceptible to a disease which can be improved or prevented by affecting microglial activation.

The present invention relates to a composition comprising achillolide A (AcA), for use in treating a mammal suffering from or susceptible to a neurodegenerative condition.

The present invention further relates to the composition in the preceding paragraph, wherein said neurodegenerative condition is selected from Alzheimer's disease, Parkinson's disease and Amyotrophic Lateral Sclerosis (ALS), ischemia, immunodeficiency virus-1 (HIV-1)-associated dementia, Lewy body associated dementia, traumatic brain injury (TBI), glioma, schizophrenia, Huntington's disease, multiple sclerosis, glaucoma and epilepsy.

The present invention relates to a composition comprising AcA, for use in treating a mammal suffering from or susceptible to a disease which can be improved or prevented by affecting neuroinflammation.

The present invention relates to a composition comprising AcA, for use in treating a mammal suffering from or susceptible to a disease which can be improved or prevented by affecting a condition selected from a group consisting of: neuronal oxidative stress and astrocytic oxidative stress.

The present invention relates to a composition comprising AcA, for use in treating a mammal suffering from or susceptible to a disease which can be improved or prevented by affecting oxidative stress in brain.

The present invention relates to a composition comprising AcA, for use in treating a mammal suffering from or susceptible to a disease which can be improved or prevented by affecting glutamate toxicity.

The present invention relates to a composition comprising AcA, for use in treating a mammal suffering from or susceptible to a disease which can be improved or prevented by affecting amyloid beta toxicity.

A composition comprising AcA, for use in treating a mammal suffering from or susceptible to a disease which can be improved or prevented by affecting microglial activation.

The present invention relates to a composition comprising AcA, for use in treating a mammal suffering from or susceptible to a disease which can be improved or prevented by increasing the levels of glial derived neurotrophic factor (GDNF) in astrocytes.

The present invention relates to a composition comprising AcA, for use in treating a mammal suffering from inflammation, said inflammation can be improved or prevented by reducing levels of a cytokine in splenocytes.

The present invention further relates to a composition according to any one of the preceding paragraphs, wherein said composition in the form of drug, food, medicinal food, food additive or beverage.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

DETAILED DESCRIPTION OF THE INVENTION

Figure 1:
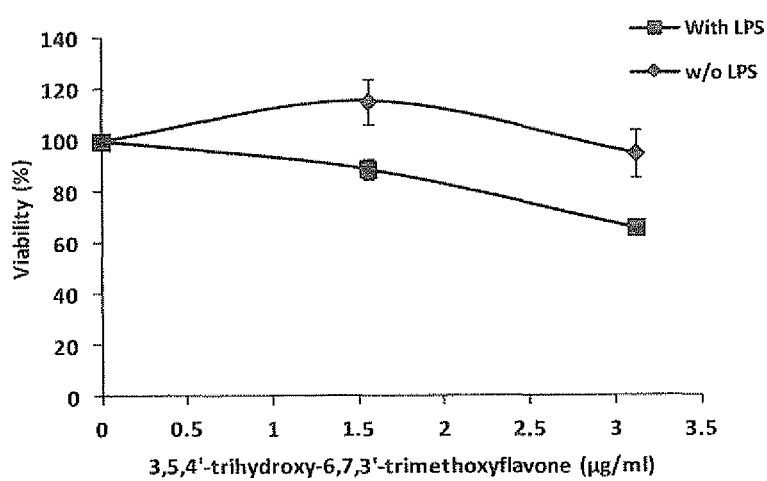
FIG. 1 shows the effect of 3,5,4'-trihydroxy-6,7,3'-trimethoxyflavone (TTF) on microglial viability.

In the present invention, inventors have purified from *Achillea fragrantissima* (Af) an active compound determined by spectroscopic methods to be a flavonoid named 3,5,4'-trihydroxy-6,7,3'-trimethoxyflavone (TTF). The structure of the TTF compound appears in formula I:

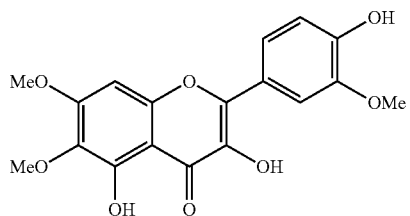

Formula I

In primary cultures of glia cells, TTF inhibited the LPS-elicited secretion of the proinflammatory cytokines Interleukin 6 (IL-6) and IL-1beta. TTF also protected cultured astrocytes from $H_2O_2$-induced cell death via interference with cell signaling (inhibition of SAPK/JNK, ERK 1/2, MEK1 and CREB phosphorylation) and by reducing the levels of oxidative stress-induced intracellular ROS. TTF protected neuronal cells from amyloid beta and glutamate cytotoxicity. TTF interfered with amyloid beta-induced cell signaling events (inhibition of SAPK/JNK, ERK 1/2, MEK1 and CREB phosphorylation) and reduced the amyloid beta and glutamate-induced levels of intracellular reactive oxygen species (ROS). Thus, the present invention relates to TTF in prevention or treatment of neurodegenerative diseases such as Alzheimer's disease, Parkinson's disease and ALS, as well as other neurodegenerative diseases, where neuroinflammation, oxidative stress, glutamate and amyloid beta toxicity are part of the pathophysiology.

The anti-neuroinflammatory compound achillolide A was purified from Af. The purified anti-inflammatory molecule was fully characterized by its 1D and 2D NMR data and was found to be achillolide A isolated from the same *Achillea*: $C_{17}H_{20}O_6$, MWt 320, 8DBEs. The structure of the pure molecule is presented in Formula II.

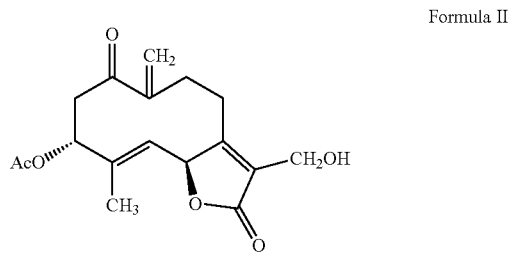 [SMILES: C=C1CCC2=C(CO)C(=O)O[C@H]2/C=C(\C)[C@H](OC(C)=O)CC1=O]

Formula II

In primary cultures of microglial cells, achillolide A inhibited the LPS-elicited expression of the proinflammatory cytokines Interleukin 1β (IL-1β) and Tumor necrosis factor-α (TNFα) and of the inflammatory enzymes cyclooxygenase-2 (COX-2), induced nitric oxide synthase (iNOS) and matrix metalloproteinase-9 (MMP-9), and down-regulated nitric oxide (NO) and glutamate secretion from activated microglial cells. The inhibitory activities were not a result of any cytotoxic effect. Achillolide A also inhibited the induced secretion of inflammatory cytokines from LPS-activated splenocytes. Achillolide A also induced the expression of glial derived neurotrophic factors (GDNF) in primary cultures of brain astrocytes, and protected these cells from oxidative stress induced cell death. Achillolide A also prevented the $H_2O_2$-induced ROS levels in primary cultures of brain astrocytes and prevented the $H_2O_2$-induced phosphorylation of MEK1, ERK1/2, p38 and SAPK/JNK in these cells. Studies with neuronal cells showed that achillolide A prevented the $A\beta_{25\text{-}35}$-induced cytotoxic effect, the $A\beta_{25\text{-}35}$-induced ROS elevation, and the $A\beta_{25\text{-}35}$-induced SAPK/JNK, ERK1/2 phosphorylation at nanomolar concentrations.

Effect of TTF and AcA on several factors that are outlined hereinbelow is a major part of this invention. Oxidative stress has emerged as a major mechanism that underlies the etiology of a variety of neuropathological disorders, including ischemic stroke, traumatic brain injury (TBI), depression, schizophrenia, ALS, glaucoma, epilepsy, multiple sclerosis, Huntington's disease, Alzheimer's disease and Parkinson's disease. Oxidative stress, caused by reactive oxygen species (ROS), is a major contributor to inflammatory bowel disease (IBD)-associated neoplasia. According to J Infect Dis. 2003 May 1; 187(9):1411-5, in experimental bacterial meningitis, matrix metalloproteinases (MMPs) and reactive oxygen species (ROS) contribute to brain damage. MMP-9 increases in cerebrospinal fluid (CSF) during bacterial meningitis and is associated with the brain damage that is a consequence of the disease. In experimental bacterial meningitis, matrix metalloproteinases (MMPs) and reactive oxygen species (ROS) contribute to brain damage. MMP-9 increases in cerebrospinal fluid (CSF) during bacterial meningitis and is associated with the brain damage that is a consequence of the disease. In bacterial meningitis, matrix metalloproteinases (MMPs) and reactive oxygen species (ROS), which are both produced as part of the host's immune response to bacteria, contribute to the pathogenesis of brain damage MMP-9 is released in an inactive proform (proMMP-9) and must be processed to become biologically active. The catalytic zinc molecule in proMMP-9 is sterically blocked in the prodomain by a cysteine residue (i.e., cysteine switch), a process that renders the enzyme inactive. Activation of proMMP-9 occurs when the prodomain is cleaved by other proteases or when the cysteine switch is disrupted. Disruption can occur, at physiological concentrations of ROS, as a result of oxidation of the cysteine thiol group. MMPs and ROS both have been shown to be involved in BBB breakdown and in brain damage in bacterial meningitis.

IL-6 is a multifunctional cytokine produced mainly by monocytes, macrophages and activated T cells. Although IL-6 expression has been implicated in the pathogenesis of a variety of diseases including glomerulonephritis, multiple myeloma, rheumatoid arthritis, and cardiac myxoma, IL-6 was predominantly detected in ulcerative colitis and Crohn's disease specimens of the inflammatory samples. Serum IL-6 level correlates with the disease state as the level decrease upon improvement of the disease condition, and returns to the control level when inflammation in the gut subsides. Moreover, in colitis-associated cancer, IL-6 plays a critical tumor promoter during early tumorigenesis by enhancing proliferation and survival of normal and premalignant intestinal epithelial cells.

It is known that ROS causes IL-1beta release and that ROS acts as second messengers whose signaling drives inflammasome activation. Activation of IL-1beta is ROS-dependent (Science. 2008; 320(5876):674-7; Nat Immunol. 2009; 10(3):241-7. In a positive feedback loop, IL-1beta promotes intracellular accumulation of ROS. Furthermore, inhibitors of ROS production inhibit secretion of IL-1beta (PLoS One. 2012; 7(9):e45186.)

Glutamate-evoked excitotoxicity has been implicated in the etiology of many neurodegenerative diseases including Alzheimer's disease, Parkinson's disease, and ischemic stroke. ROS provoked by glutamate-linked oxidative stress plays crucial role in the pathogenesis of these disorders.

Amyloid beta induces ERK1/2, MEK1, SAPK/JNK and CREB phosphorylation. CREB is a prominent transcription factor in the nervous system, and activates transcription of target genes in response to diverse array of stimuli, including oxidative stress. It is also well known that hydrogenperoxide (H2O2) induces ERK1/2, MEK1, SAPK/JNK and CREB phosphorylation.

Compounds of the invention may also be applied on Huntingtons disease (HD). Oxidative damage plays an important role in HD pathogenesis (Mitochondrial dysfunction, metabolic deficits, and increased oxidative stress in Huntington's disease. Chen C M. Chang Gung Med J. 2011 34(2):135-52) as well as (Antioxidants in Huntington's disease. Johri A, Beal M F. Biochim Biophys Acta. 2012; 1822(5):664-74).

Abbreviations used in this invention are as follows:

Aβ—amyloid beta; ABAP—2,2'-Azobis(amidinopropane); AcA—achillolide A Af—*Achillea fragrantissima*; CAA—Cellular antioxidant activity; CNS—Central nervous system; COSY—Correlation spectroscopy; CREB—Cyclic AMP response element-binding protein; DCF-DA—27'-dichlorofluorescein diacetate; DPPH-2,2-diphenyl-1-pieryhydrazyl; ERK—Extracellular signal regulated kinase; GDNF—Glial derived neurotrophic factor. $H_2O_2$—Hydrogen peroxide; HMBC—Heteronuclear multiple-bond correlation spectroscopy; HSQC—Heteronuclear single quantum coherence spectroscopy; MAPK—Mitogen-activated protein kinase; MEK—Mitogen activated protein kinase kinase; NMR—Nuclear magnetic resonance; ROS—Reactive oxygen species; SAPK/JNK—Stress-activated protein kinase/c-Jun N-terminal kinase; TTF-3,5,4'-trihydroxy-6,7,3'-trimethoxyflavone; COX-2-Cyclooxygenase-2; IL-2/6/10/12—Interleukin 2/6/10/12; IL-1β—Interleukin 1β; α—alpha; β—beta; iNOS—Induced nitric oxide synthase; LPS—Lipopolysaccharide; MMP-9—Matrix metalloproteinase-9; NO—Nitric oxide; SL—sesquiterpene lactone; TNFα—Tumor necrosis factor-α; SNP—Sodium nitroprusside; INF-γ—Interferon-Gamma.

In the present invention, inventors have purified and evaluated the effectiveness of the flavonoid TTF for counteracting oxidative damage in cultured astrocytes. Inventors have found that TTF protected astrocytes from $H_2O_2$-induced cell death and attenuated the intracellular accumulation of ROS following treatment with $H_2O_2$ or ABAP.

Interestingly, although quercetin, which was used as a control flavonoid, had both free radical and $H_2O_2$ scavenging abilities, its protective effect on brain astrocytes was significantly less than that of TTF. These observations emphasize the importance of interference with cell signaling events as part of the protective mechanism of TTF.

In the cellular anti-oxidant activity (CAA) assay, the efficiency of cellular uptake and/or membrane binding combined with that of the radical-scavenging activity dictate the efficacy of the tested compound in reducing ROS levels. The results of the cellular anti-oxidant assay indicate that TTF (or its metabolite) can penetrate the plasma membrane and react with ROS inside the cells. Thus, it should be further studied whether TTF, which is characterized by a relatively low polarity and low molecular weight (MWt 360.3), might traverse the blood brain barrier and affect brain functions as was shown for other flavonoids.

According to the results presented in this invention, the maximal protective activity of TTF against oxidative stress was higher than that of memantine. Moreover, while memantine could scavenge neither $H_2O_2$ nor free radicals, TTF had free radical scavenging ability. Thus, TTF has complementary activities to those of memantine.

Some of the chemicals and Reagents used in this invention are specified herewith:

Dulbecco's modified Eagle's medium (DMEM), Leibovitz-15 medium, glutamine, antibiotics (10,000 IU/mL penicillin and 10,000 µg/mL streptomycin), soybean trypsin inhibitor, fetal bovine serum (FBS) and Dulbecco's phosphate buffered saline (PBS) (without calcium and magnesium) were purchased from Biological Industries (Beit Haemek, Israel); 2-mercaptoethanol, crystal violet, 2,2-Diphenyl-1-pierylhydrazyl (DPPH), Quercetin (3,3',4',5,7-Pentahydroxyflavone), Memantine, and 2'7'-dichlorofluorescein diacetate (DCF-DA) were purchased from Sigma Chemical Co. (St Louis, Mo., USA). 2,2'-Azobis(amidinopropane) (ABAP) was obtained from Wako chemicals (Richmond, Va.). Dimethyl sulfoxide (DMSO) was obtained from Applichem (Darmstadt, Germany); and hydrogen peroxide ($H_2O_2$) was obtained from MP Biomedicals (Ohio, USA).

Plant Material:

*Achillea fragrantissima* were collected in the Arava Valley, and the voucher specimens have been kept and authenticated as part of the Arava Rift Valley Plant Collection; VPC (Dead Sea & Arava Science Center, Central Arava Branch, Israel, under the accession code AVPC0040).

Extraction and Isolation.

Sun/freeze dried Af (1 kg) was homogenized and extracted with petrol ether (3×500 mL, 24 hrs), followed by ethyl acetate (3×500 mL, 24 hrs). After evaporation of the latter solvent the residual gum was chromatographed on a Sephadex LH-20 column, eluting with MeOH/CH2Cl2 (1:1). The fractions containing the TTF, according to a TLC plate, were chromatographed again, twice on Sephadex LH-20 columns and silica gel, using hexane with increasing proportions of ethyl acetate as fluent. TTF was afforded by elution with 40% ethyl acetate in hexane. Infra red (IR) spectra were obtained with a Bruker Fourier transform infra red spectra (FTIR) Vector 22 spectrometer. $^1$H and $^{13}$C NMR spectra were recorded on Bruker Avance-500 spectrometer. Correlation spectroscopy (COSY), heteronuclear single quantum coherence spectroscopy (HSQC) and heteronuclear multiple-bond correlation spectroscopy (HMBC) experiments were recorded using standard Bruker pulse sequences. High resolution electrospray mass spectroscopy (HRES-IMS) measurements were performed using the instrument Waters Micromass SYNAPT HDMS mass spectrometer, time of flight (TOF).

The compound (MWt 360.3) was determined by proton and carbon NMR and mainly 2D NMR experiments to be 3,5,4'-trihydroxy-6,7,3'-trimethoxyflavone (TTF). The structure of the pure molecule is presented in Formula I.

Preparation of Primary Cultures of Glial Cells.

Primary cultures of astrocytes were prepared from cerebral cortices of 1-2 day-old neonatal Wistar rats as described (Elmann et al., 2011b). Fourteen days old astrocytes were used in the experiments. The research was conducted in accordance with the NIH guide for the care and use of laboratory animals, and was approved by the Institutional Animal Care and Use Committee of The Volcani Center, Agricultural Research Organization (IL-135/07, approval date Apr. 11, 2007). All efforts were made to minimize animal suffering and to reduce the number of animals used.

Determination of Cell Viability.

Astrocytes were re-plated at 24-well poly-D-lysine-coated plastic plates at a density of $1\times10^5$/well, in DMEM w/o Phenol Red containing 2% FBS, 2 mM glutamine, 100 U/mL penicillin, and 100 µg/mL streptomycin. $H_2O_2$ in the presence or absence of TTF were added, and cell viability was determined using a commercial colorimetric assay (Roche Applied Science, Germany) according to the manufacturer's instructions. This assay is based on the measurement of lactate dehydrogenase (LDH) activity released from the cytosol of damaged cells into the incubation medium. The absorbance was measured at 492 nm in a plate reader. The percentage of cytotoxicity was calculated according to the following equation, where the "$A_{Triton-x\ treated\ cells}$" is the maximum releasable LDH in the cells:

$$\text{Cytotoxicity (\%)} = \frac{A_{treated\ cells} - A_{untreated\ cells}}{A_{Triton-x\ treated\ cells} - A_{untreated\ cells}} \times 100$$

In the cellular antioxidant activity (CAA) assay, cell viability was determined by a modification of the crystal violet assay (Kueng et al., 1989) as follows. At the end of cell treatments, cells were fixed with 150 µL of 5% (v/v) formaldehyde (in PBS) for 15 min at room temperature. Plates were washed by submersion in de-ionized water, dried and stained for 15 min with 150 µL of a 1% crystal violet solution. After careful aspiration of the crystal violet solution the plates were washed with de-ionized water, and dried prior to the solubilization of the bound dye with 150 µL of a 33% aqueous glacial acetic acid solution. The optical density of the plates was measured at 540 nm (with a 690 nm reference filter) in a microplate spectrophotometer.

Evaluation of Intracellular ROS Levels.

Intracellular ROS levels were detected using the non-fluorescent cell permeating compound, 2'7'-dichlorofluorescein diacetate (DCF-DA). DCF-DA is hydrolyzed by intracellular esterases and then oxidized by ROS to a fluorescent compound 2'-7'-DCF. Astrocytes were plated onto 24 wells plates (300,000 cells/well) and treated with DCF-DA (20 µM) for 30 min at 37° C. Following incubation with DCF-DA, cultures were rinsed twice with PBS and then re-suspended in DMEM containing 10% FBS, 8.4 mM HEPES, 2 mM glutamine, 100 U/ml penicillin, and 100 µg/mL streptomycin. ROS levels (fluorescence) at time zero were measured in a plate reader with excitation at 485 nm and emission at 520 nm. Astrocytes were then treated with TTF for 2 h before the addition of $H_2O_2$ and ROS levels (fluorescence) were measured in a plate reader with excitation at 485 nm and emission at 520 nm every hour for 4 h.

The percentage of ROS levels was calculated according to the following equation (where F is the fluorescence):

$$\text{ROS levels (\%)} = \frac{F_{TTF\ and\ H_2O_2\ treated\ cells} - F_{untreated\ cells}}{F_{H_2O_2\ treated\ cells} - F_{untreated\ cells}} \times 100$$

Cellular Antioxidant Activity (CAA) of the flavonoid TTF.

Intracellular ROS production was detected using the non-fluorescent cell permeating compound, 2'7'-dichlorofluorescein diacetate (DCF-DA). DCF-DA is hydrolyzed by intracellular esterases and then oxidized by ROS to a fluorescent compound 2'-7'-DCF. Peroxyl radicals are generated by thermolysis of 2,2'-Azobis(amidinopropane) (ABAP) at physiological temperature. ABAP decomposes at approximately $1.36\times10^{-6}s^{-1}$ at 37° C., producing at most $1\times10^{12}$ radicals/mL/s (Bowry and Stocker, 1993; Niki et al., 1986; Thomas et al., 1997). Astrocytes (300,000 cells/well) were plated in DMEM containing 2% FBS, 8.4 mM HEPES, 2 mM glutamine, 100 U/mL penicillin and 100 µg/mL streptomycin, onto 24 well plates. In order to measure the ability of TTF to enter the cells and prevent the formation of dichlorofluorescein (DCF) by ABAP-generated peroxyl radicals, cells were incubated for 1 h with TTF. Then the cells were preloaded with DCF-DA for 30 min, washed twice with PBS, and ABAP (0.6 mM final concentration) was then added. The fluorescence, which indicates ROS levels, was measured in a plate reader with excitation at 485 nm and emission at 520 nm.

Treatment of Astrocytes.

The original medium of the cells was aspirated off and fresh medium was added to the cells. Dilutions of TTF first in DMSO and then in the growth medium were made freshly from stock solution just prior to each experiment and were used immediately. The final concentration of DMSO in the medium was 0.2%. Dilutions of $H_2O_2$ in the growth medium were made freshly from 30% stock solution just prior to each experiment and were used immediately. Each treatment was performed in replicates.

Enzyme-Linked Immunosorbent Assays (ELISA) for Total and Phospho-SAPK/JNK, Total and Phospho-ERK (Phospho-p44/42 MAPK), Total and Phospho-MEK1, and Total and Phospho CREB.

Astrocytes were treated with TTF 2 h before the addition of $H_2O_2$. Cells were lysed 40 minutes after the addition of $H_2O_2$ in lysis buffer supplied by PathScan sandwich ELISA kit (Cell Signaling TECHNOLOGY) according to the manufacturer's protocol. Protein concentrations in cell lysates were determined by Bradford reagent (Bio-Rad, Hercules, Calif.), and equal amounts of proteins were subjected to ELISA. To measure the amount of total and phosphoSAPK/JNK in cell lysates of astrocytes, ELISA was performed according to the manufacturer's protocol using the PathScan total SAPK/JNK sandwich ELISA kit (Cell Signaling TECHNOLOGY) and the PathScan phospho-SAPK/JNK (Thr183/Tyr185) sandwich ELISA kit (Cell Signaling TECHNOLOGY), respectively. To measure the amount of total and phospho-ERK 1/2 (i.e. phospho-p44/42 MAPK) in cell lysates of astrocytes, ELISA was performed according to the manufacturer's protocol using the PathScan total p44/42 MAPK (ERK 1/2) sandwich ELISA kit (Cell Signaling TECHNOLOGY) and the PathScan phospho-p44/42 MAPK (Thr202/Tyr204) sandwich ELISA kit (Cell Signaling TECHNOLOGY), respectively. To measure the amount of total and phospho-MEK1 in cell lysates of astrocytes, ELISA was performed according to the manufacturer's protocol using the PathScan total MEK1 sandwich ELISA kit (Cell Signaling TECHNOLOGY) and the PathScan phospho-MEK1 (Ser217/221) sandwich ELISA kit (Cell Signaling TECHNOLOGY), respectively. To measure the amount of total and phospho-CREB in cell lysates of astrocytes, ELISA was performed according to the manufacturer's protocol using the PathScan total CREB sandwich ELISA kit (Cell Signaling TECHNOLOGY) and the PathScan phospho-CREB (Ser133) sandwich ELISA kit (Cell Signaling TECHNOLOGY), respectively. The optical density was determined at 450 nm using a microplate reader.

Determination of the Free Radical Scavenging Activity in the DPPH Assay.

Antioxidant activity was measured using the 2,2-diphenyl-1-pieryhydrazyl (DPPH) radical scavenging assay. Different dilutions of TTF (or control drugs) were added to 1 mL of DPPH (3.9 mg/100 mL methanol) in test tubes wrapped in aluminum foil. Absorbance (A) was measured at 517 nm after 8 min incubation in the dark. The scavenging ability (%) of the samples was calculated as $(A_{control} - A_{sample})/A_{control} \times 100)$.

Determination of $H_2O_2$ Scavenging Activity.

The scavenging of $H_2O_2$ was determined by the method of Ruch et al. *Carcinogenesis.* 1989 June; 10(6):1003-8, using 1 mM instead of 4 mM $H_2O_2$. A 1 mM solution of $H_2O_2$ was prepared in PBS and was incubated with different concentrations of TTF, quercetin or memantine. Absorbance (A230) was determined spectrophotometrically 10 min later against blank solutions containing TTF, quercetin or memantine in PBS without $H_2O_2$.

Data Analysis.

Statistical analyses were performed with one-way ANOVA followed by Tukey-Kramer multiple comparison tests using Graph Pad InStat 3 for windows (GraphPad Software, San Diego, Calif., USA).

Results.

TTF Protected Astrocytes Against $H_2O_2$-Induced Cell Death.

Figure 2A:
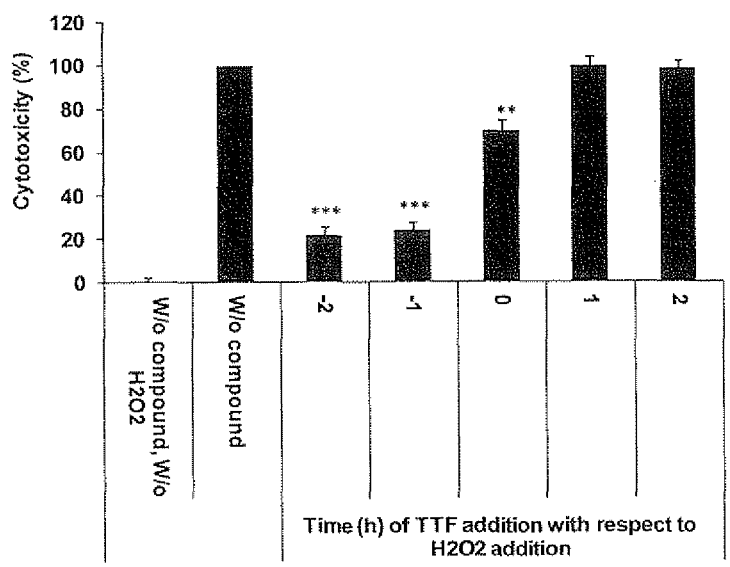
FIG. 2A-C show protection of astrocytes from $H_2O_2$-induced cell death by TTF.
Figure 2B:
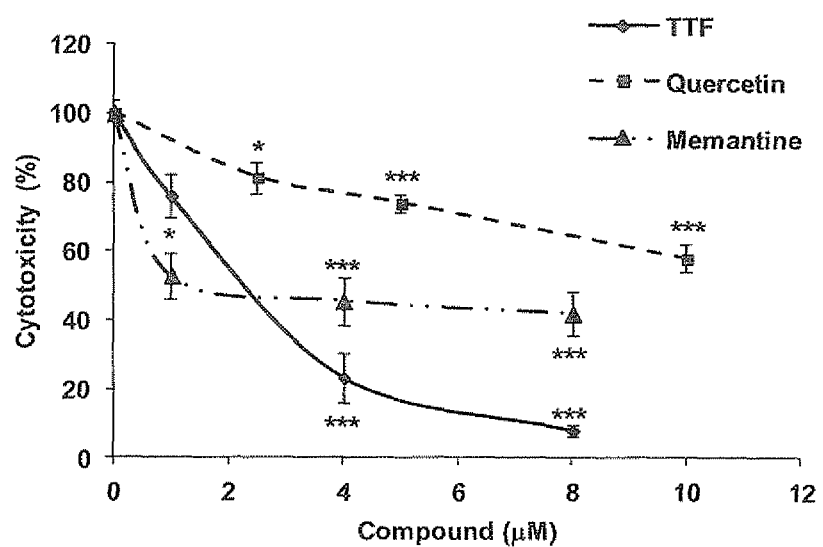
Figure 2C:
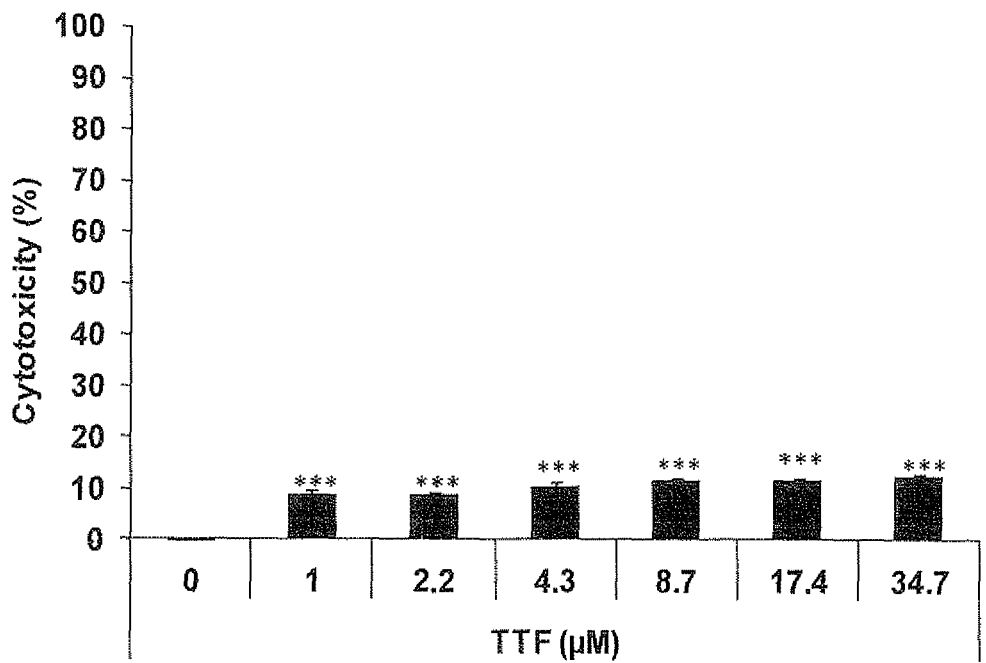

In order to characterize the ability of TTF to protect against $H_2O_2$-induced astrocytic cell death, inventors assessed changes in cell viability using a model in which oxidative stress was induced by the addition of $H_2O_2$ to cultures of primary astrocytes. The concentration of $H_2O_2$ used in experiments (175-200 µM) resembles the concentration reported in rat striatum under ischemic conditions (Hyslop et al., 1995). Exposure of normal primary astrocytes to $H_2O_2$ resulted in the time and concentration-dependent death of astrocytes at 20 h after exposure (Elmann et al., 2011b). Since preincubation of astrocytes with TTF was found to be a prerequisite for the protective effect against $H_2O_2$ cytotoxicity (FIG. 2A), astrocytes were preincubated with different concentrations of this molecule, and the optimal concentration of TTF needed for a protective effect was determined. Following preincubation, $H_2O_2$ was added, and cytotoxicity was determined 20 h later using the LDH assay. Results show that TTF exhibited a protective effect against $H_2O_2$-induced cell death, and was fully effective (92% protection) at 8 µM (FIG. 2B). It should be noted that at all concentrations tested, the cytotoxicity of this flavonoid by itself to astrocytes was very low (<11%) as was determined by the LDH method (FIG. 2C). As a positive control, inventors have used the flavonoid quercetin, a known antioxidant, which was studied in primary astrocytes and was found to be nontoxic up to 100 µM (Nones et al., 2012). Quercetin was significantly less effective (p<0.01) than TTF and at 10 µM provided only 36% protection (FIG. 2B). The protective activity of TTF was also compared to that of memantine, which is used as a drug for the treatment of Alzheimer's disease. At the maximal effective concentration of TTF (8 µM), memantine was significantly less effective (p<0.005) than TTF (that provided 92% protection) and provided only 58% protection (FIG. 2B). However, at 1 µM (the lowest concentration that was tested), memantine provided 48% protection against $H_2O_2$ toxicity and was more effective than similar concentrations of TTF (24% protection) and quercetin. These results indicate that at low concentrations (1 µM), memantine seems to be more effective than TTF and quercetin; however, its effect reaches a plateau and at 8 µM (the effective dose of TTF), memantine is less effective than TTF.

Treatment of Astrocytes with TTF Inhibited $H_2O_2$-Induced Phosphorylation of SAPK/JNK, MEK1 and ERK 1/2.

Figure 3A:
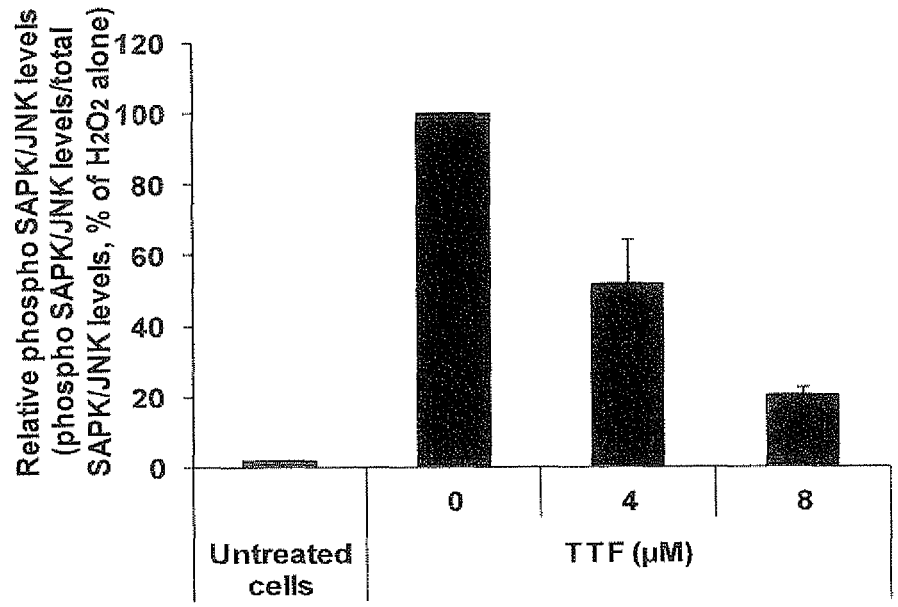
FIGS. 3A-C show suppression of $H_2O_2$-induced SAPK/JNK, ERK 1/2 and MEK1 phosphorylation in astrocytes by TTF.
Figure 3B:
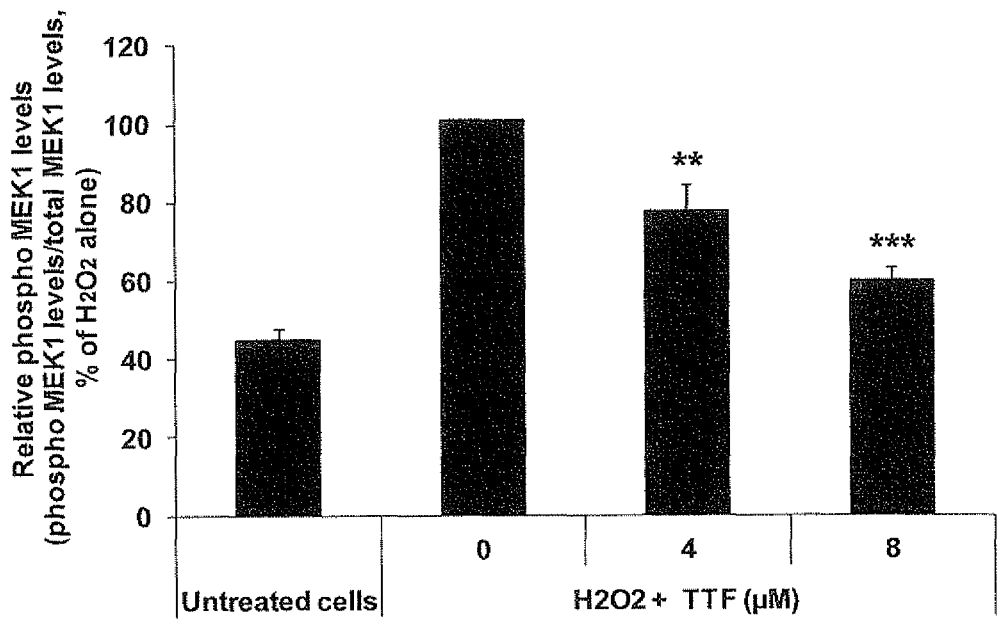
Figure 3C:
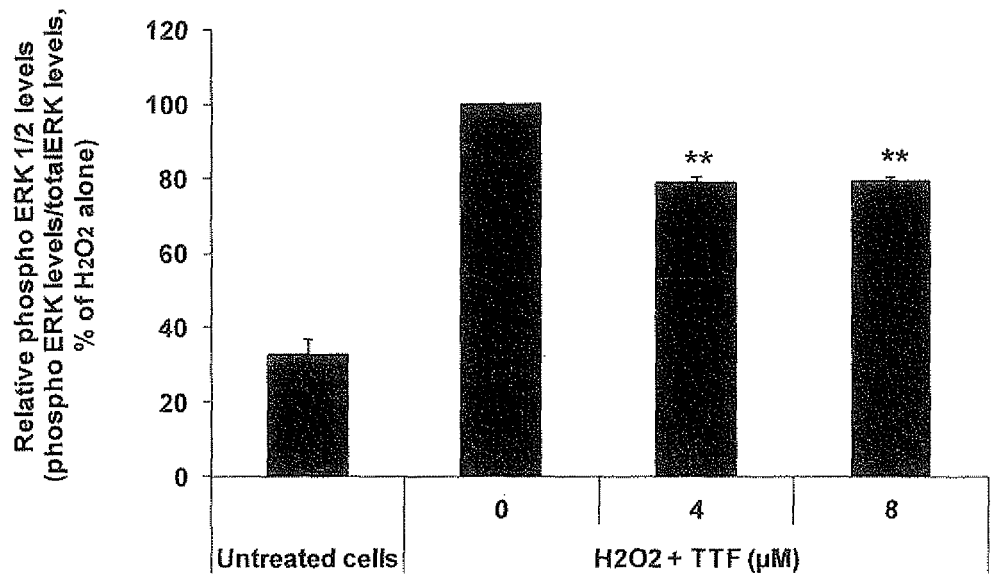

The mitogen-activated protein kinases (MAPKs) are a family of secondary messengers that convey signals from the cell surface to the nucleus in response to a wide range of stimuli, including stress. $H_2O_2$ has been reported to stimulate the activity of the MAPK extracellular signal regulated kinase (ERK) and stress-activated protein kinase/c-Jun N-terminal kinase (SAPK/JNK) in primary cultured astrocytes (Tournier et al., 1997). Moreover, antioxidants have been shown to attenuate the activation of MAPK signaling, indicating that the MAPK signaling pathway is a target of ROS (Mantena and Katiyar, 2006). Therefore, inventors attempted to determine whether the protective effect of TTF against $H_2O_2$-induced cell death is mediated through the inhibition of $H_2O_2$-induced SAPK/JNK, MEK1 and/or ERK 1/2 phosphorylation. As in the protection experiments described above, astrocytes were pretreated with different concentrations of TTF 2 h prior to their exposure to $H_2O_2$. Treatment of astrocytes with $H_2O_2$ markedly increased the phosphorylation of SAPK/JNK, MEK1 and ERK 1/2, as was determined using specific ELISA kits (FIG. 3). TTF inhibited 80% of the $H_2O_2$-induced phosphorylation of SAPK/JNK in astrocytes, without affecting the total amount of SAPK/JNK in the cells (FIG. 3A). TTF also inhibited 27% and 30% of the $H_2O_2$-induced phosphorylation of MEK1 (FIG. 3B) and ERK 1/2 (FIG. 3C), respectively, without affecting the total amounts of these proteins in the cells. In light of this correlation, inventors suggest that the protective effects of TTF on brain astrocytes under oxidative stress might be partially attributed to the inhibition of SAPK/JNK, MEK1 and ERK 1/2 phosphorylation.

Treatment of Astrocytes with TTF Inhibited $H_2O_2$-Induced Phosphorylation of the Transcription Factor CREB.

Figure 4:
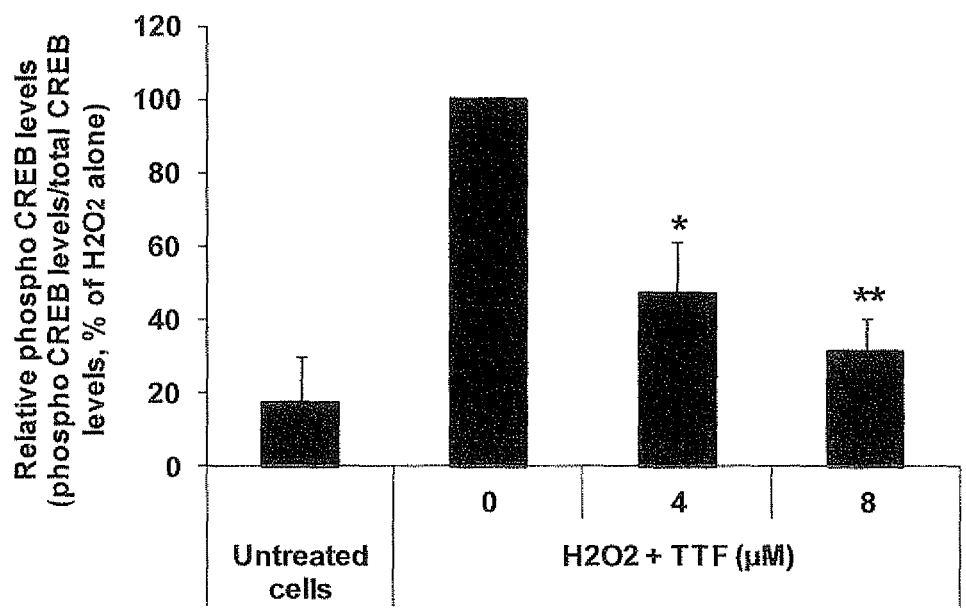
FIG. 4 shows the effect of TTF on $H_2O_2$-elevated phosphorylation of CREB in astrocytes.

$H_2O_2$ was shown to modulate the activity of transcription factors in mammalian cells and to induce the phosphorylation of cAMP response element-binding protein (CREB) in astrocytes. CREB is a prominent transcription factor in the nervous system, and activates transcription of target genes in response to diverse array of stimuli, including oxidative stress. Therefore it was of interest to determine the effect of TTF on CREB phosphorylation in astrocytes under oxidative stress. For this purpose, as in the previous experiments described above, astrocytes were pretreated with different concentrations of TTF 2 h prior to their exposure to $H_2O_2$. As can be seen in FIG. 4, CREB is strongly phosphorylated in response to $H_2O_2$, and TTF inhibited 80% of the $H_2O_2$-induced phosphorylation of CREB in astrocytes, without affecting the total amount of CREB in the cells (FIG. 4). In light of the correlation between the protective effect of TTF and the inhibition of CREB phosphorylation, inventors suggest that inhibition of CREB phosphorylation is involved in the protective effects of TTF against $H_2O_2$-induced astrocytic cell death.

TTF Inhibited the $H_2O_2$-Induced Generation of ROS.

Figure 5A:
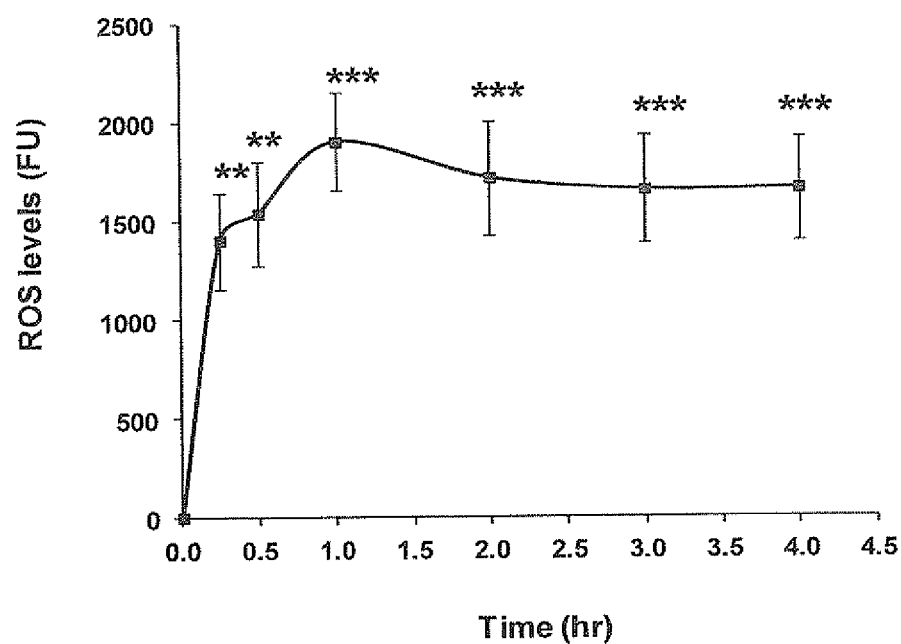
FIGS. 5A-C show the TTF attenuation of $H_2O_2$-induced ROS levels in astrocytes.
Figure 5B:
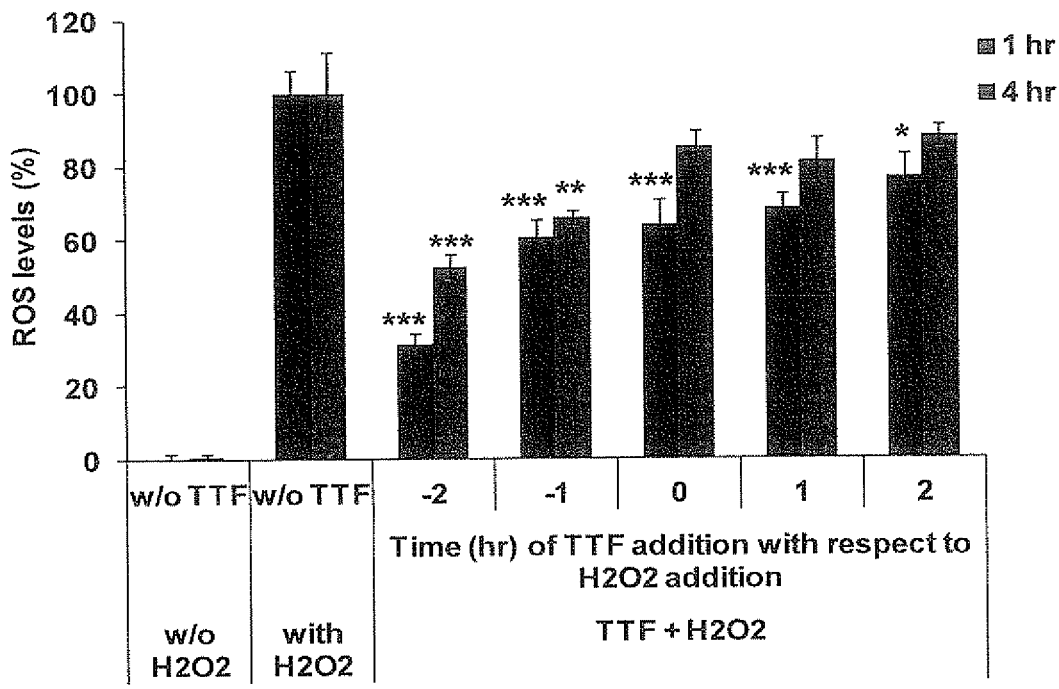
Figure 5C:
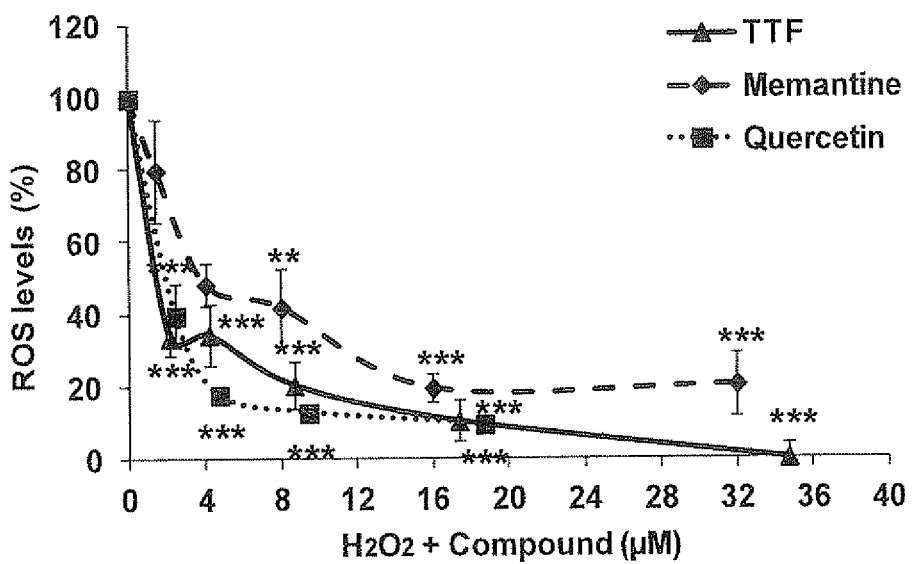

$H_2O_2$-induced cell death is accompanied by an increase in ROS levels. Thus inventors raised the possibility that in addition to the interference in signaling events, TTF could protect astrocytes from $H_2O_2$-induced cell death by inhibiting the production of ROS that are induced by $H_2O_2$. To assess the intracellular levels of ROS, astrocytes were preloaded with the ROS indicator DCF-DA and were pretreated with various concentrations of TTF before the application of $H_2O_2$. ROS formation was determined by examining fluorescence every hour for 4 h. As shown in FIG. 5A, $H_2O_2$ induced production of ROS in astrocytes, with the maximum levels of ROS produced after 1 h. To test whether treatment of astrocytes with TTF affected the induced ROS levels, and to determine the time at which TTF best ameliorates $H_2O_2$-induced ROS levels, the cells were preincubated with TTF (8 μM) for 2 h or 1 h, co-treated with $H_2O_2$ and TTF, or post-treated (for 2 h or 1 h) with TTF. Results show that TTF inhibited the $H_2O_2$-induced elevation of intracellular ROS, and that TTF is more effective in attenuating ROS levels when applied 2 hr before the addition of $H_2O_2$ to astrocytes (FIG. 5B). Inventors have next compared the effect of TTF to those of quercetin and memantine. The experiments were conducted at the same experimental conditions as for the cytotoxicity and signaling experiments. As can be seen in FIG. 5C, TTF was more efficient than memantine in reducing the $H_2O_2$-induced ROS, and at concentrations that were higher than 16 μM, there was no significant difference ($p>0.05$) between the abilities of TTF, quercetin, and memantine to reduce the $H_2O_2$-induced ROS.

Hydrogen-Peroxide Scavenging Activity of TTF.

Figure 6:
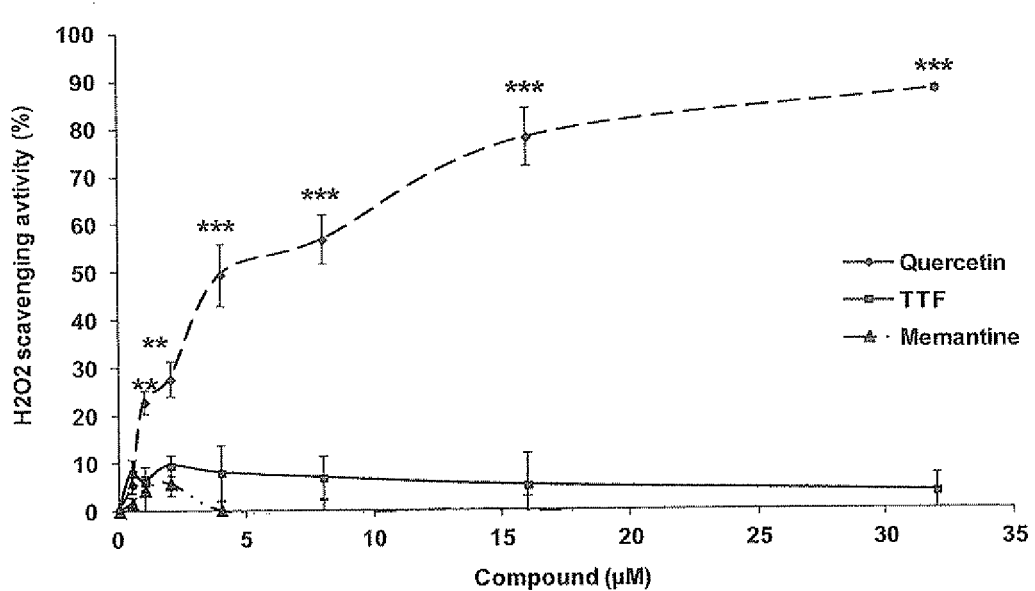
FIG. 6 shows hydrogen peroxide scavenging activity of TTF compared to memantine and to quercetin.

To determine whether the protective effect of TTF against $H_2O_2$ cytotoxicity might be the result of $H_2O_2$ scavenging by TTF, the ability of TTF to scavenge $H_2O_2$ was measured, and was compared to the scavenging ability of quercetin and memantine. For the invention of $H_2O_2$ scavenging, the compounds were incubated with 1 mM $H_2O_2$ solution for 10 min, following which, the concentration of $H_2O_2$ was determined spectrophotometrically by measuring its absorbance at 230 nm. The results presented in FIG. 6 demonstrate that at the protective concentration of TTF (8 μM), while the control flavonoid quercetin scavenged 57% of $H_2O_2$, TTF scavenged only 7% of $H_2O_2$ (FIG. 6). At higher concentrations (up to 32 μM) the scavenging ability of quercetin was increased to 88%, while the scavenging ability of TTF was not increased beyond 7%. Thus the protective effect of TTF cannot be attributed only to $H_2O_2$ scavenging. FIG. 6 also demonstrates that memantine did not have any scavenging ability towards $H_2O_2$.

Free-Radical Scavenging Activity of TTF.

Figure 7:
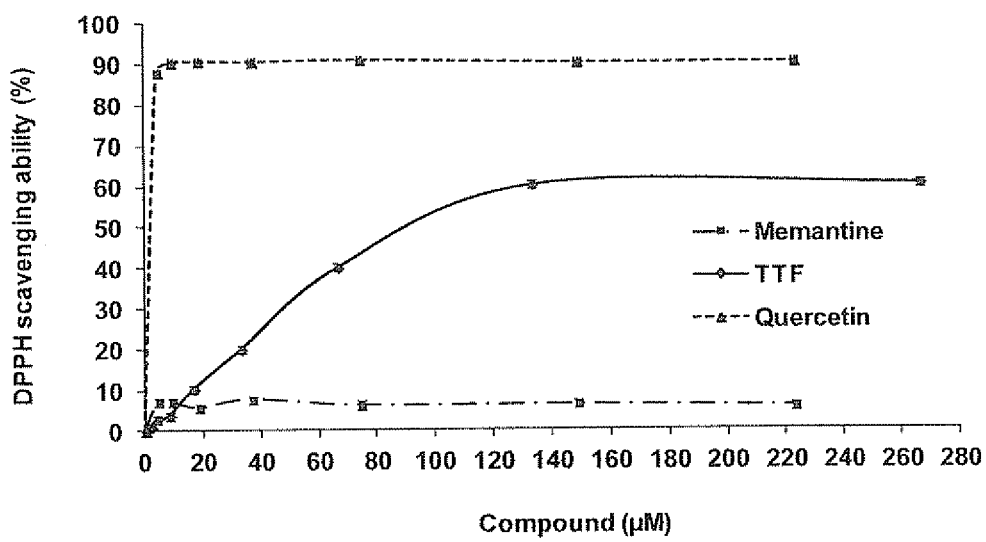
FIG. 7 shows DPPH radical scavenging activity of TTF compared to memantine and to quercetin.

The results of the previous experiments indicated that TTF protects brain astrocytes from oxidative stress (FIG. 2) and inhibits the $H_2O_2$-induced generation of ROS (FIG. 5). These effects were probably not due to the direct scavenging of $H_2O_2$ (FIG. 6) but might be related to a free-radical scavenging ability of TTF. In order to test this possibility, the free-radical scavenging activity of TTF, was determined in a cell free in vitro system using the 2,2-diphenyl-1-pieryhydrazyl (DPPH) radical. In this assay, TTF was found to be a free-radical scavenger with an $IC_{50}$ value of 45 μM and 60% inhibition of DPPH absorbance at 517 nm (FIG. 7). TTF was a better radical scavenger than memantine, which showed only 7% inhibition, and had a lower scavenging activity than quercetin, which was used as a control flavonoid (90% inhibition). Thus, it seems that the protective effect of TTF might be attributed in part to its radical scavenging ability rather to its $H_2O_2$-scavenging ability.

TTF Reduced Peroxyl Radical Levels Produced by 2,2'-Azobis(Amidinopropane) in Astrocytes.

Figure 8A:
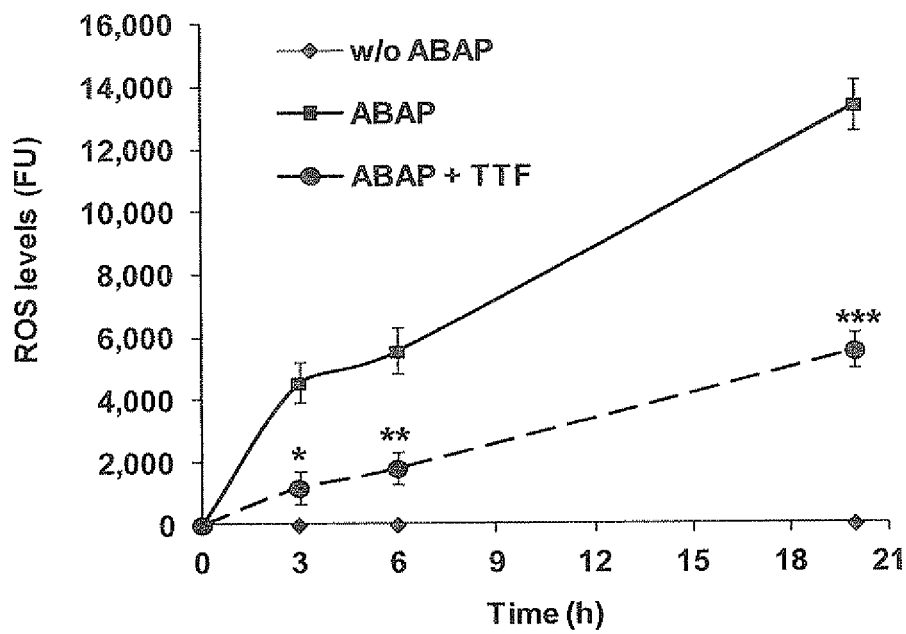
FIG. 8A-C show that TTF reduced peroxyl radical levels produced by 2,2'-Azobis(amidinopropane) in astrocytes.
Figure 8B:
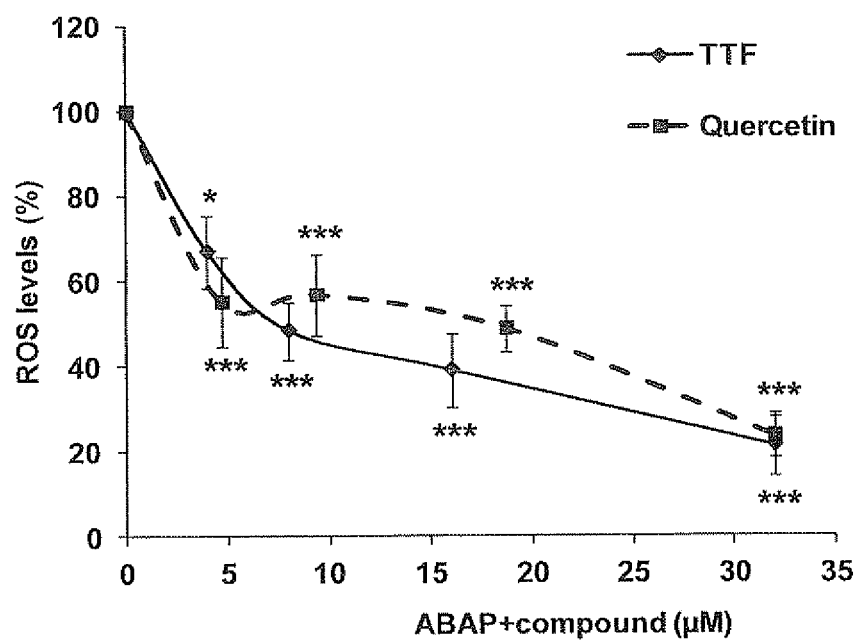
Figure 8C:
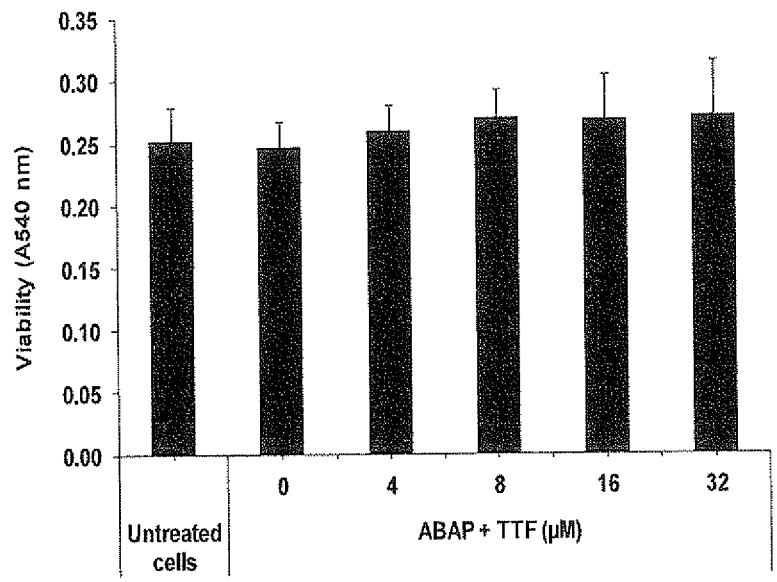

TTF might elicit its antioxidant effects by disrupting peroxyl radical chain reactions at the cell surface, or by penetrating the cell and reacting with ROS inside the cell. In order to discriminate between these possibilities, inventors used a cellular antioxidant activity assay and measured the ability of TTF to prevent the intracellular formation of DCF by peroxyl radicals generated intracellularly by ABAP. Astrocytes were pre-incubated with ABAP, which generates peroxyl radicals inside cells. The kinetics of DCF formation in astrocytes by peroxyl radicals generated from ABAP is shown in FIG. 8A. As shown in this figure (FIG. 8A, B), ABAP generated radicals in a time-dependent manner and treatment of cells with TTF moderated the increase in ROS-induced fluorescence. It should be noted that cell viability was not affected in this experimental system (FIG. 8C). At all concentrations tested quercetin, which was used as a control flavonoid, was similarly effective as TTF in reducing intracellular ROS levels in astrocytes ($p>0.05$; FIG. 8B).

In one embodiment, there is the use of TTF as a drug for the prevention or treatment of brain injuries and neurodegenerative diseases in which oxidative stress and astrocytic cell death play important roles.

In another embodiment, in primary cultures of microglial cells, TTF inhibits the LPS-elicited secretion of the proinflammatory cytokines Interleukin Interleukin 6 (IL-6) and IL-1beta.

Figure 22:
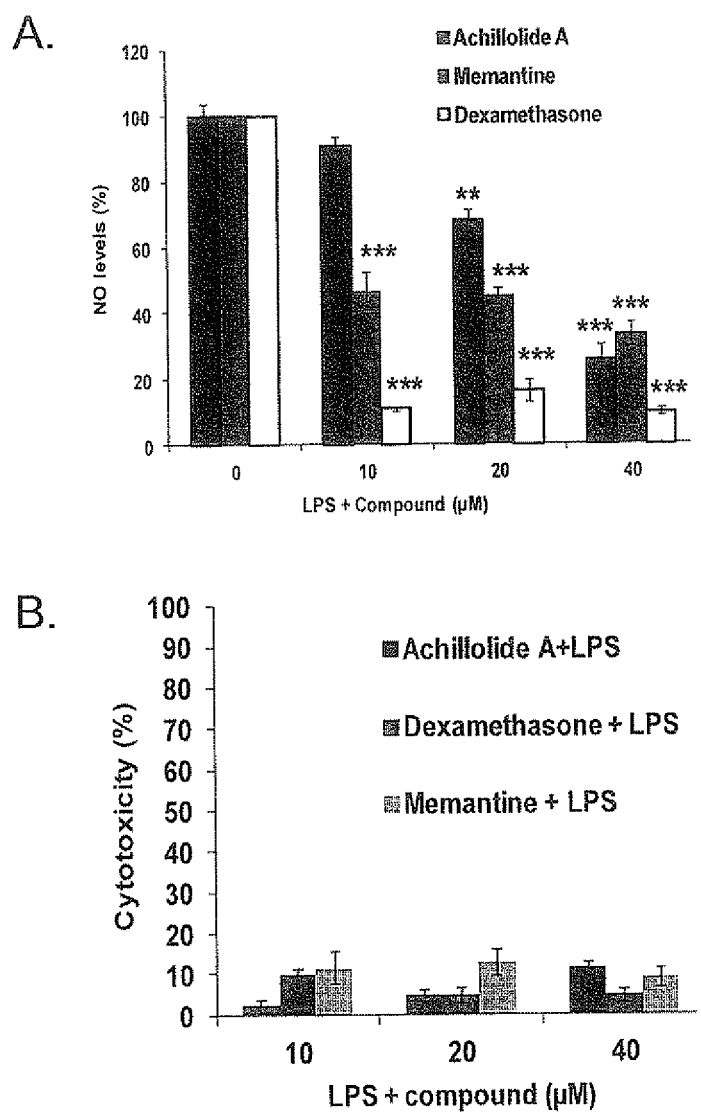
FIGS. 22A-B show inhibition of NO production and lack of cytotoxicity by activated microglial cells in response to different concentrations of achillolide A.

According to the present invention, TTF markedly inhibited the LPS-elicited IL-6 and IL-1β secretion from microglial cells (FIG. 9A-C and FIG. 1) without a significant cytotoxic effect (FIG. 22B).

The Effect of TTF on Cultured Neuronal Cells

Figure 10A:
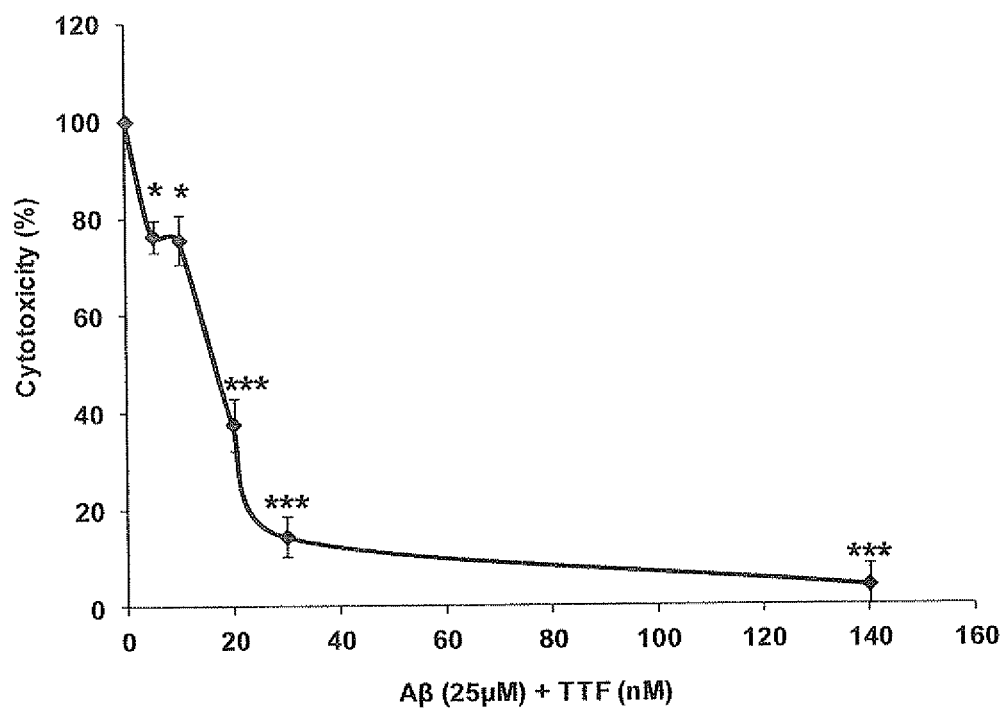
FIGS. 10A-B show that TTF prevents the $A\beta_{25-35}$-induced neuronal cell death.
Figure 10B:
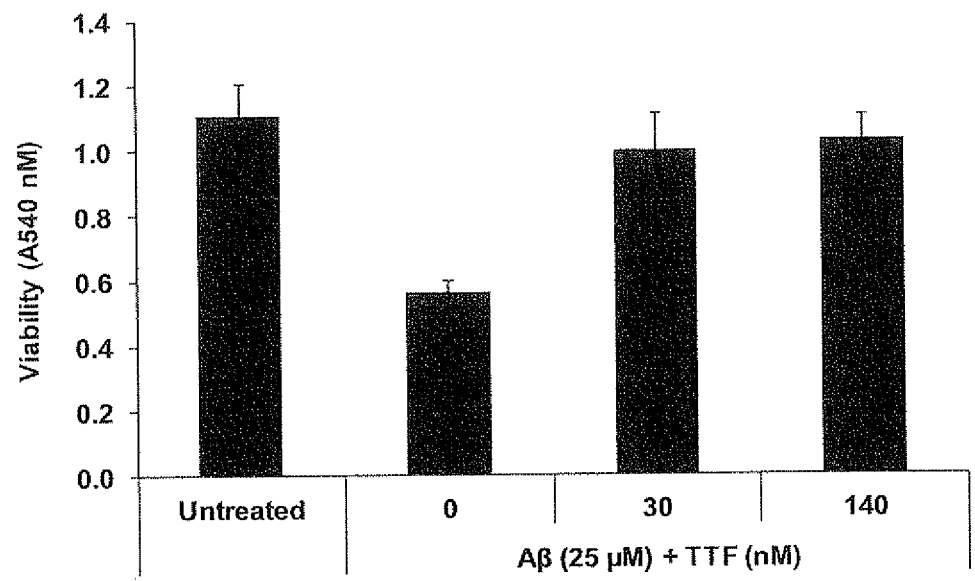

One embodiment of the invention refers to Amyloid beta$_{25-35}$ (Aβ$_{25-35}$)-induced neuronal cell death. Inventors have examined the effect of TTF on neuronal viability following cell treatment with the cytotoxic peptide Amyloid beta$_{25-35}$ (Aβ$_{25-35}$). Treatment of neuronal cells with Aβ$_{25-35}$ causes cytotoxicity [as was measured by the LDH method (FIG. 10A) and by the crystal violet staining (FIG. 10B)]. As demonstrated in FIG. 10, TTF prevents the cytotoxic effect at nanomolar concentrations.

Figure 11:
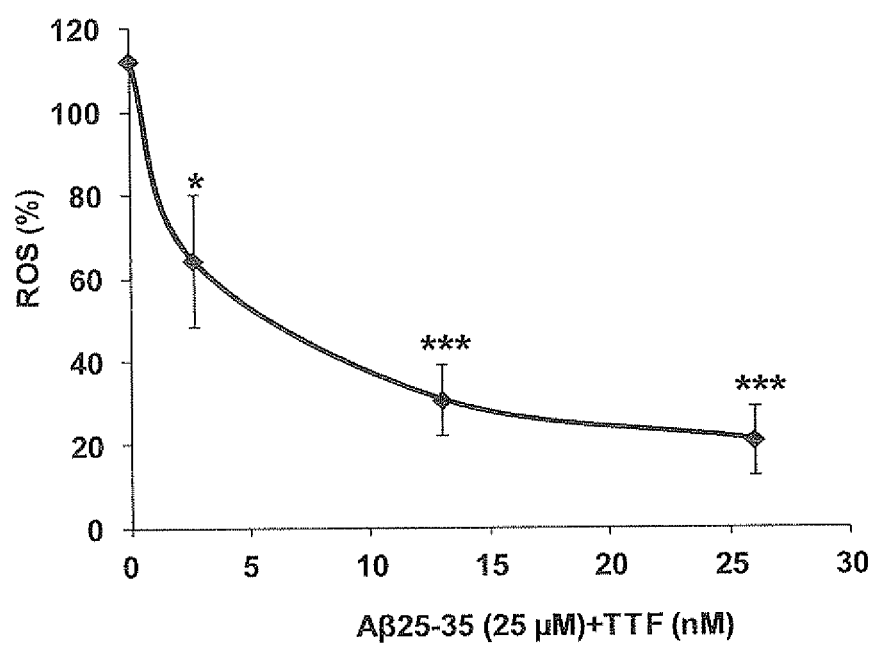
FIG. 11 shows that TTF prevents the $A\beta_{25-35}$-induced reactive oxygen species (ROS) elevation.

Another embodiment of the invention refers to Aβ$_{25-35}$-induced reactive oxygen species (ROS) elevation. Inventors next examined the effect of TTF on ROS levels induced by Aβ$_{25-35}$. Treatment of neuronal cells with Aβ$_{25-35}$ causes elevation in ROS levels, and treatment with TTF prevents the elevation in ROS levels (FIG. 11)

Figure 12A:
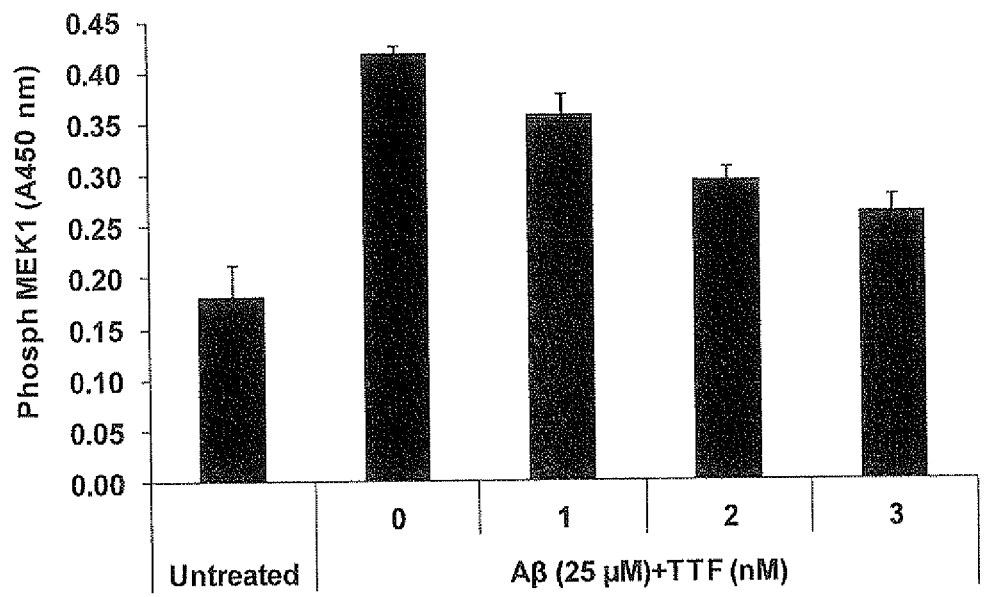
FIG. 12A-B shows that TTF down-regulates the $A\beta_{25-35}$-induced phosphorylation of MEK1 in N2a neuronal cells without affecting the levels of total MEK1.
Figure 12B:
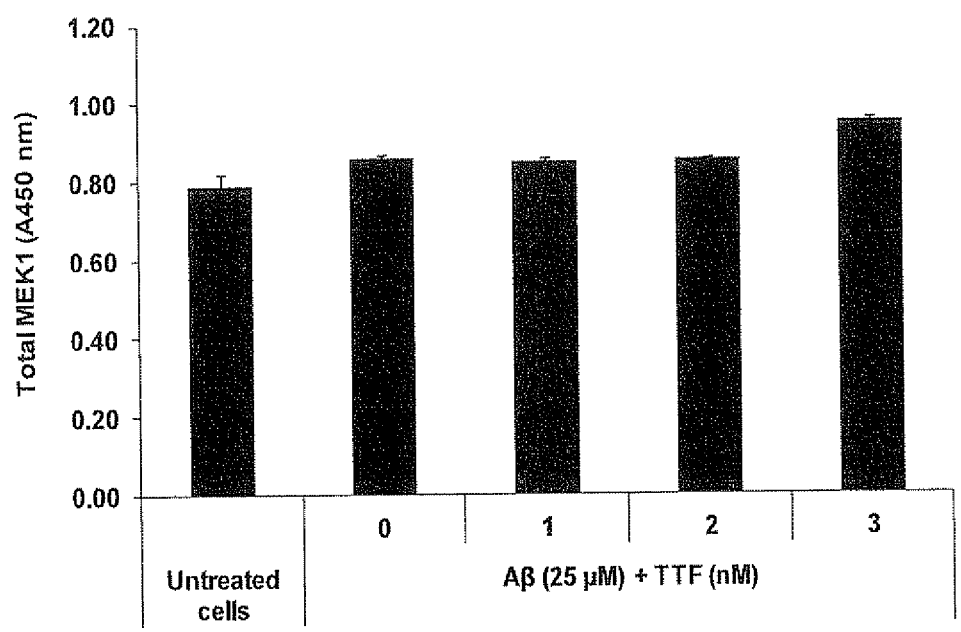
Figure 13:
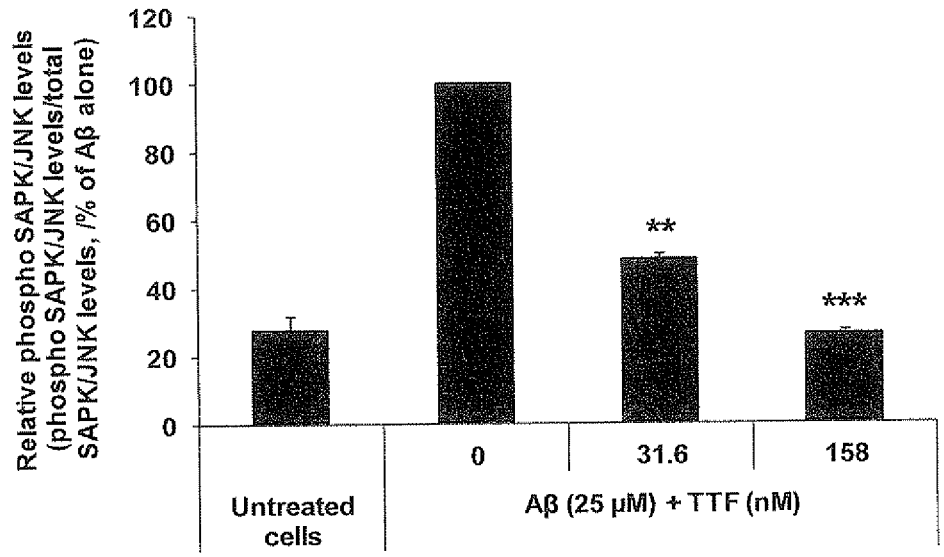
FIG. 13 shows that TTF down-regulates the $A\beta_{25-35}$-induced phosphorylation of SAPK/JNK in N2a neuronal cells without affecting the levels of total SAPK/JNK.
Figure 14:
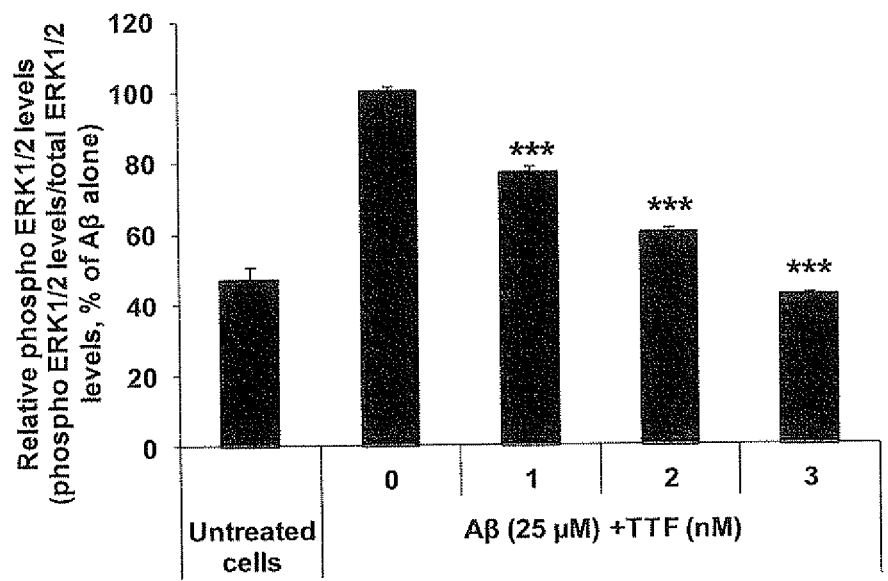
FIG. 14 shows that TTF down-regulates the $A\beta_{25-35}$-induced phosphorylation of ERK1/2 in N2a neuronal cells without affecting the levels of total ERK1/2.

Another embodiment of the invention refers to Aβ$_{25-35}$-induced phosphorylation of mitogen-activated protein kinases (MAPK) proteins. Inventors also examined the effect of TTF on signaling pathways induced by Aβ$_{25-35}$. As can be seen in FIGS. 12-14, treatment of neuronal cells with Aβ$_{25-35}$ causes the phosphorylation of mitogen activated protein kinase kinase (MEK1), extracellular signal regulated kinase (ERK1/2) and stress-activated protein kinase/Jun-amino-terminal kinase (SAPK/JNK). FIGS. 12-14 also demonstrate that TTF significantly inhibited the $A_{25\text{-}35}$-induced phosphorylation of these proteins in N2a neuronal cells, without affecting the total amount of each of those proteins. Thus, the protective effects of TTF on N2a cells might be partially attributed to the inhibition of the $A\beta_{25\text{-}35}$-induced phosphorylation of these proteins which belong to the mitogen-activated protein kinases (MAPK) family.

Figure 15A:
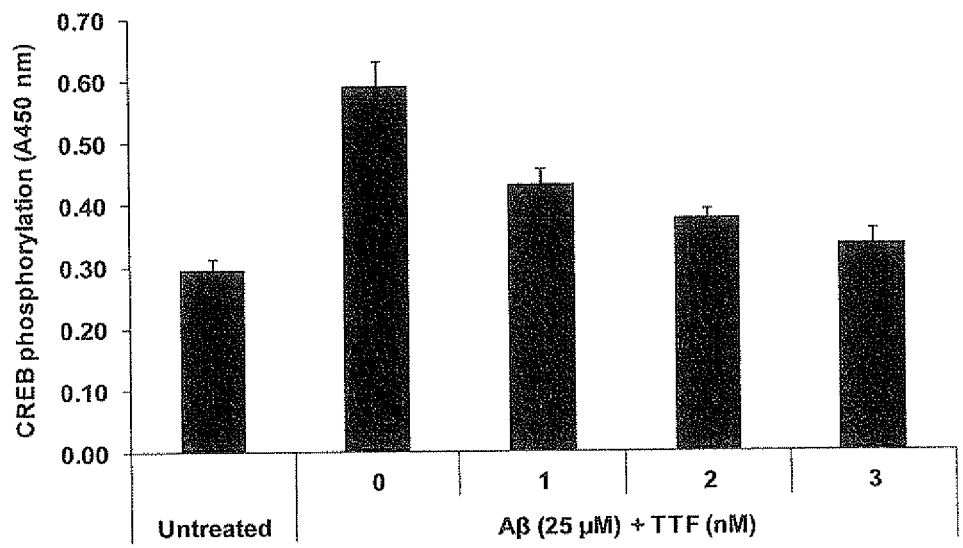
FIGS. 15A-B show that TTF down-regulates the $A\beta_{25-35}$-induced phosphorylation of CREB in N2a neuronal cells without affecting the levels of total CREB.
Figure 15B:
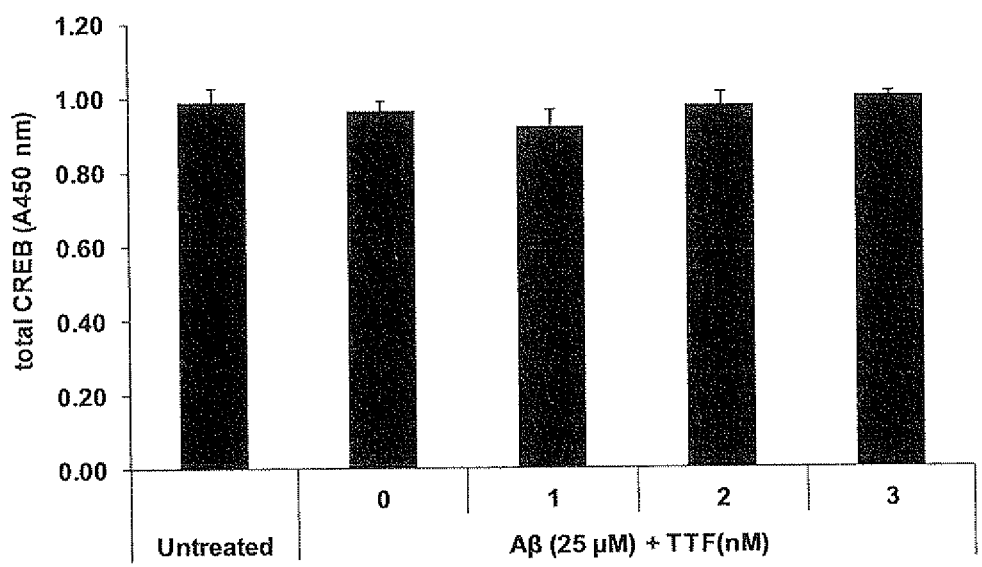

Another embodiment of the invention refers to $A\beta_{25\text{-}35}$-induced phosphorylation of the transcription factor cyclic AMP response element-binding protein (CREB). Inventors also examined the effect of TTF on the $A\gamma_{25\text{-}35}$-induced phosphorylation of cyclic AMP response element-binding protein (CREB). As can be seen in FIG. 15, treatment of neuronal cells with $A\beta_{25\text{-}35}$ caused the phosphorylation of CREB, and TTF significantly inhibited the $A\beta_{25\text{-}35}$-induced phosphorylation of CREB in N2a neuronal cells, without affecting the total amount of this protein. Thus, the protective effects of TTF on N2a cells might be partially attributed to the inhibition of the $A\beta_{25\text{-}35}$-induced phosphorylation of this transcription factor.

Figure 16:
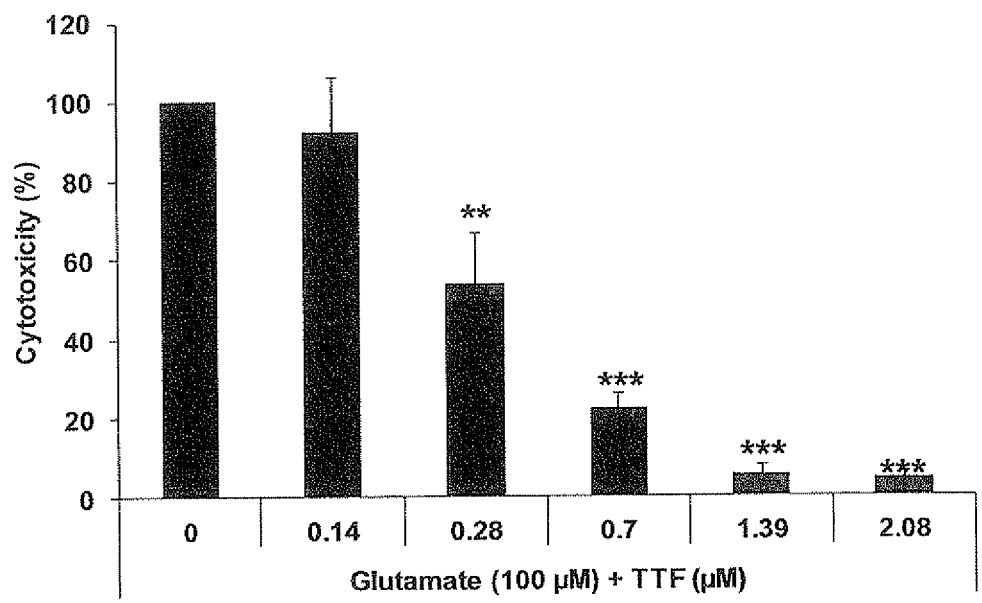
FIG. 16 shows that TTF prevents the glutamate-induced neuronal cell death.

Another embodiment of the invention refers to Glutamate-induced neuronal cell death. Inventors have examined the effect of TTF on neuronal viability following cell treatment with glutamate. Treatment of neuronal cells with glutamate causes cytotoxicity as was measured by the LDH method (FIG. 16). As demonstrated in FIG. 16, TTF prevents the cytotoxic effect at nanomolar concentrations.

Figure 17:
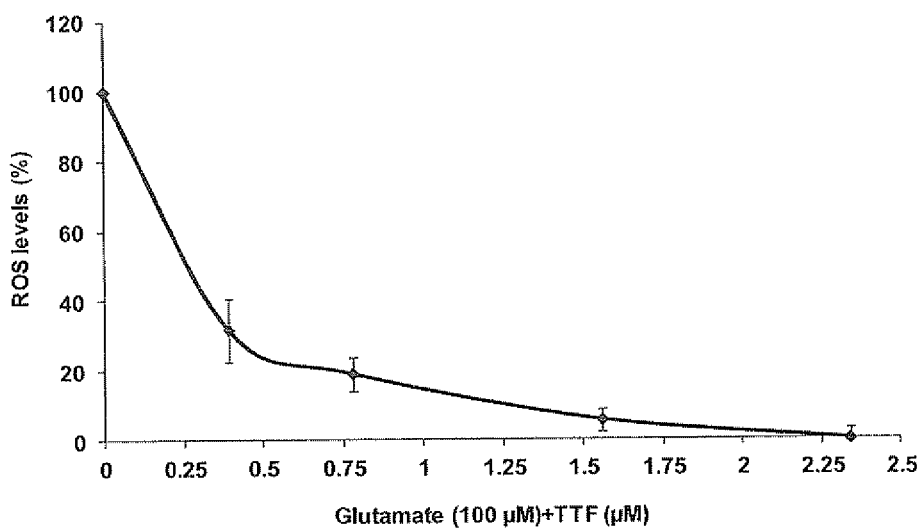
FIG. 17 shows that TTF prevents the glutamate-induced reactive oxygen species (ROS) elevation.

Another embodiment of the invention refers to Glutamate-induced reactive oxygen species (ROS) elevation. Inventors have examined the effect of TTF on ROS levels induced by glutamate. Treatment of neuronal cells with glutamate causes elevation in ROS levels, and treatment with TTF prevents the elevation in ROS levels (FIG. 17)

Figure 18:
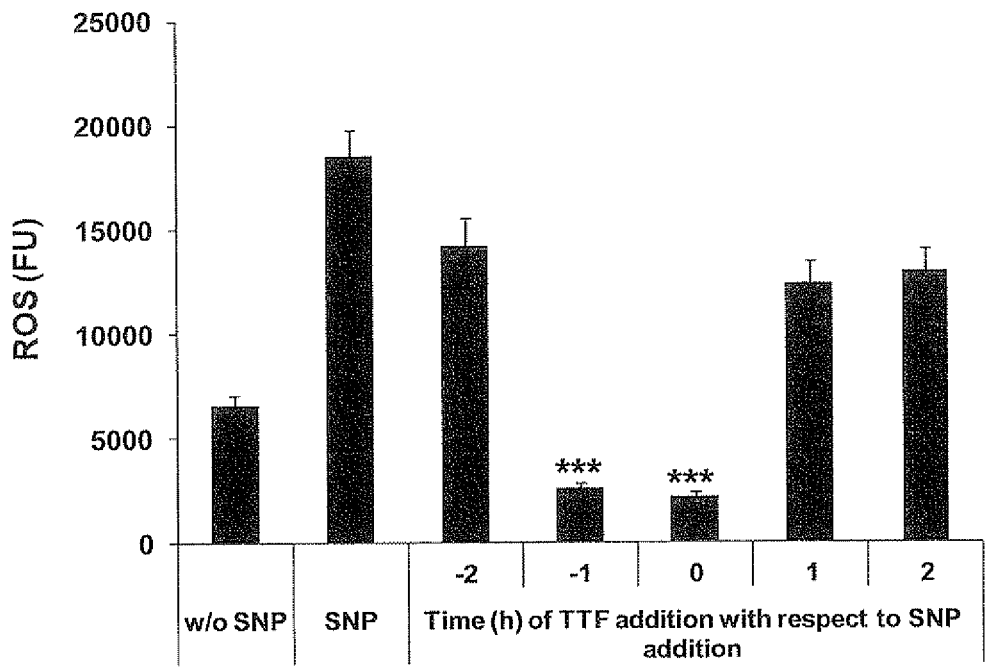
FIG. 18 shows that TTF prevents the sodium nitroprusside (SNP)-induced reactive oxygen species (ROS) elevation.

Another embodiment of the invention refers to SNP-induced reactive oxygen species (ROS) elevation. Treatment of neuronal cells with SNP causes elevation in ROS levels, and treatment with TTF attenuates the elevation in ROS levels (FIG. 18).

Figure 19:
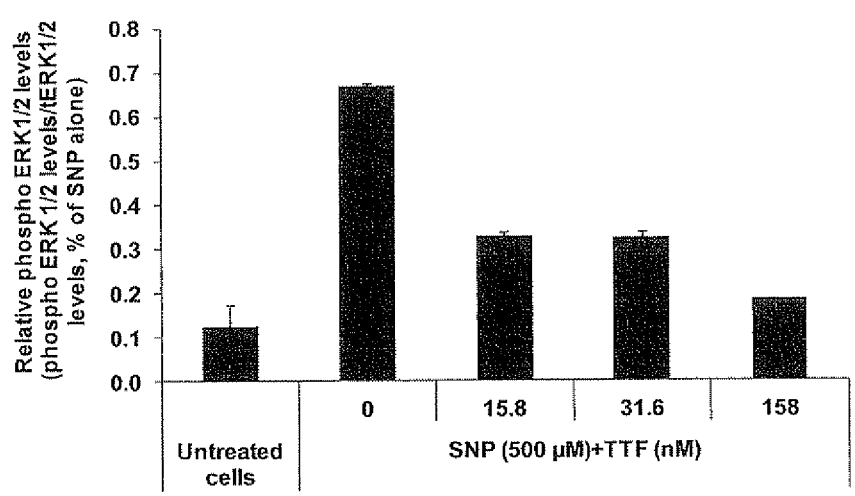
FIG. 19 shows that TTF down-regulates the SNP-induced phosphorylation of ERK1/2 in N2a neuronal cells without affecting the levels of total ERK 1/2.
Figure 20:
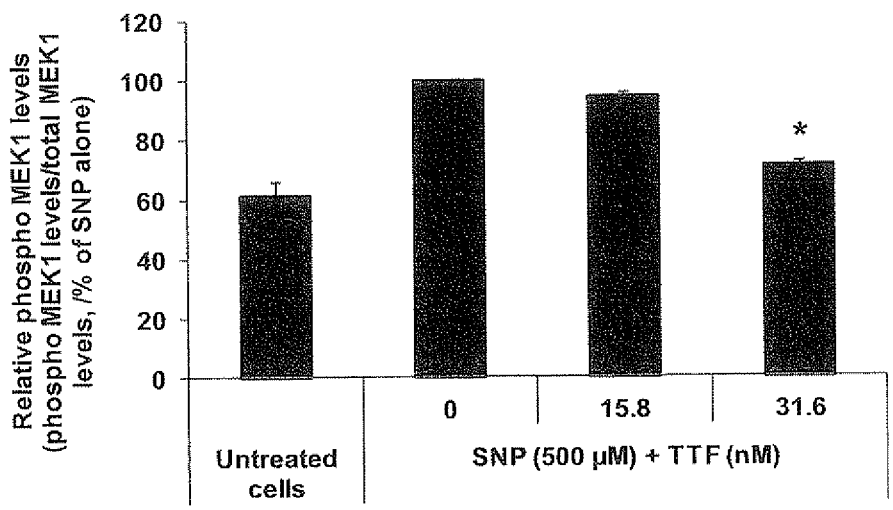
FIG. 20 shows that TTF down-regulates the SNP-induced phosphorylation of MEK1 in N2a neuronal cells without affecting the levels of total MEK1.

Another embodiment of the invention refers to SNP-induced phosphorylation of mitogen-activated protein kinases (MAPK) proteins. Inventors also examined the effect of TTF on signaling pathways induced by sodium nitroprusside (SNP). As can be seen in FIGS. 19-20, treatment of neuronal cells with SNP causes the phosphorylation of mitogen activated protein kinase kinase (MEK1) and extracellular signal regulated kinase (ERK1/2). FIGS. 19-20 also demonstrate that TTF significantly inhibited the SNP-induced phosphorylation of these proteins in N2a neuronal cells, without affecting the total amount of each of those proteins.

Achillolid A

In the present invention inventors have isolated from Af a sesquiterpene lactone named achillolide A. The effects of achillolide A have not been studied previously in any biological system. Moreover, there are only few evidence regarding the effects of sesquiterpene lactones on microglial cells, and these studies were performed using the BV2 cell line and not primary microglial cells as was used in this invention. Results show that the maximal effect of achillolide A and memantine are similar, although memantine is active at lower concentrations. Alzheimer's diseases patients are usually treated with memantine alone or a combination of acetylcholinesterase inhibitors and memantine until late in the course of the disease. Therefore combination therapy might also work for achillolide A if it will fulfill all the requirements in human clinical trials.

The results of the anti-oxidant intracellular assay indicate that achillolide A penetrates the plasma membrane and react with ROS inside those cells. This observation, combined with the relatively low molecular weight of achillolide A (MWt 320), supports the hypothesis that achillolide A might traverse also the blood brain barrier and beneficially affect brain functions.

The inflammatory mediators that were tested in this invention have become accepted markers and therapeutic targets in neurodegenerative diseases, as specific inhibitors and knockout strategies of the relevant genes could protect against brain damage in various models of brain pathologies. Therefore, substances like achillolide A that can reduce microglial activation and can protect brain cells from oxidative stress might become potential tools for treatment of neurodegenerative diseases.

Although the molecular mechanisms that underlie the anti-inflammatory effects of achillolide A require further studies, results suggest that achillolide A deserves further evaluation of its potential to be developed as a drug for the prevention or treatment of brain injuries and neurodegenerative diseases, in which inflammation and oxidative stress are part of the pathophysiology.

Down-Regulation of Microglial Activation by Achillolide A.

According to the present invention, Achillolide A markedly inhibited the LPS-elicited nitrite accumulation (FIG. 22A) without a significant cytotoxic effect (FIG. 22B). The inhibitory effect of achillolide A was compared to the inhibitory effect of the anti-inflammatory drug dexamethasone, and to memantine, which is used as a drug for the treatment of Alzheimer's disease. At low concentrations—memantine inhibited NO secretion more effectively than achillolide A. However, at the highest concentration tested (40 µM), achillolide A and memantine were similarly effective (66% and 64% inhibition, respectively), and there was not a significant difference ($P > 0.05$) between their inhibitory activities as well as their cytotoxicity. At all concentrations tested, dexamethasone was more effective than memantine and achillolide A and inhibited 90% of the NO produced by the activated cells (FIG. 22A).

Figure 21:
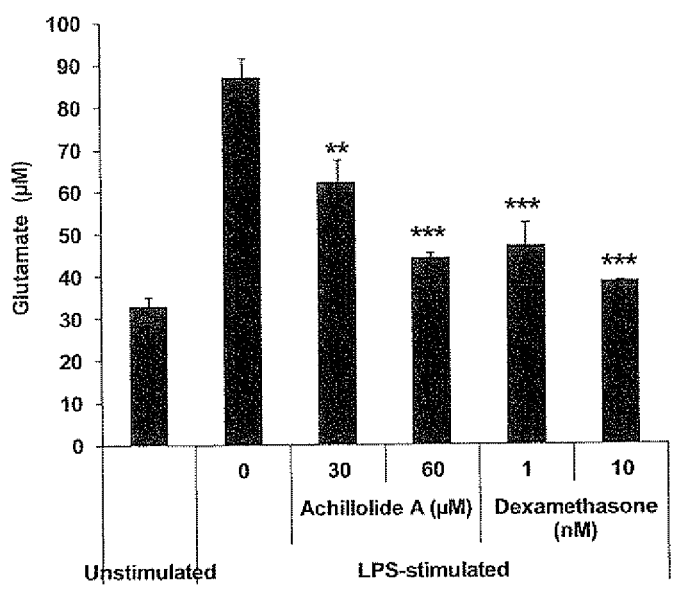
FIG. 21 shows the down-regulation of glutamate secretion from activated microglial cells by achillolide A.

When activated by pro-inflammatory stimuli, microglial cells secrete substantial levels of glutamate. The consequences could range from interference with normal neurotransmission to excitotoxicity for neurons in the vicinity. Treatment of microglial cells with LPS is known to increase glutamate secretion from microglial cells. The effect of sesquiterpenes on glutamate secretion from microglial cells was never studies before. Therefore, to test whether achillolide A affects the release of glutamate from microglial cells, LPS was added to the culture media of the cells in the presence or absence of achillolide A. Stimulation of the cells with LPS resulted in a 2.6 fold increase in glutamate secretion. Achillolide A inhibited 80% of the induced levels of secreted glutamate while dexamethasone, which was used as a control drug, inhibited 90% of the induced levels of glutamate (FIG. 21).

Pathological activation of MMPs, in particular MMP-9, has been shown to cause a number of detrimental outcomes, including blood-brain-barrier (BBB) disruption, hemorrhage, neuronal apoptosis and brain damage. To invention the effect of achillolide A on the activity of matrix metalloproteinase-9 (MMP-9) in LPS-activated microglial cells, LPS was added to the culture media of microglial cells in the presence or absence of achillolide A, and the media conditioned by the cells was collected after 24 h. As MMP-9 degrades denatured collagen (gelatin) in addition to collagen, MMP-9 activity was measured using gelatin zymography. As shown in FIG. 23A, MMP-9 activity in un-stimulated microglial cells is very low. However, stimulation of the cells with LPS resulted in a remarkable increase in MMP-9 activity compared to control cells, and this activity was markedly inhibited by achillolide A (FIG. 23A). The inhibitory effect was probably the result of inhibition of MMP-9 transcription, as was indicated by quantitative real time PCR (FIG. 23B). The inhibitory effect was not a result of cell death as no toxicity was observed using the crystal violet assay for cell viability (FIG. 23C).

Figure 24:
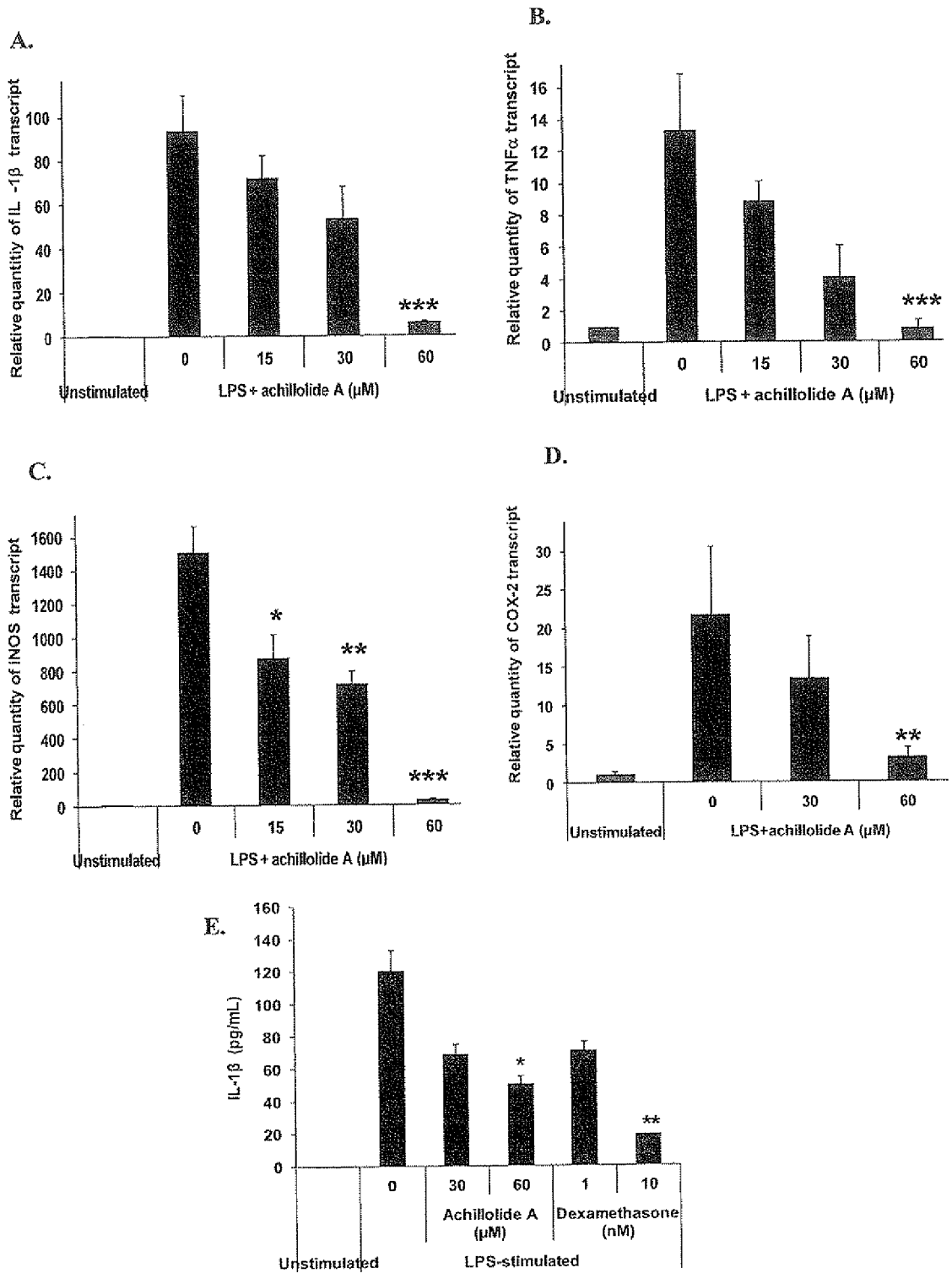
FIG. 24 shows that achillolide A attenuates the transcription of COX-2, iNOS, IL-1δ and TNFα in, and the secretion of IL-10 from LPS-stimulated microglial cells.

Achillolide A also attenuated the LPS-induced transcription of cytokines and inflammatory enzymes. While in un-stimulated microglial cells, only a small amount of induced nitric oxide synthase (iNOS), cyclooxygenase-2 (COX-2), tumor necrosis factor-α (TNFα) and interleukin 1β (IL-1β) could be detected, stimulation of the cells with LPS resulted in a remarkable increase in the levels of these transcripts compared to control cells. The induced levels of each of these inflammatory mediators were significantly inhibited by achillolide A (FIG. 24A). The inhibitory effect of achillolide A on IL-1β levels was verified by measuring the levels of IL-1β protein secreted from LPS-activated microglial cells. As demonstrated in FIG. 24B, achillolide A inhibited by 59% the secretion of IL-1β from the activated cells, and dexamethasone inhibited the secretion of this cytokine by 85%.

Figure 25:
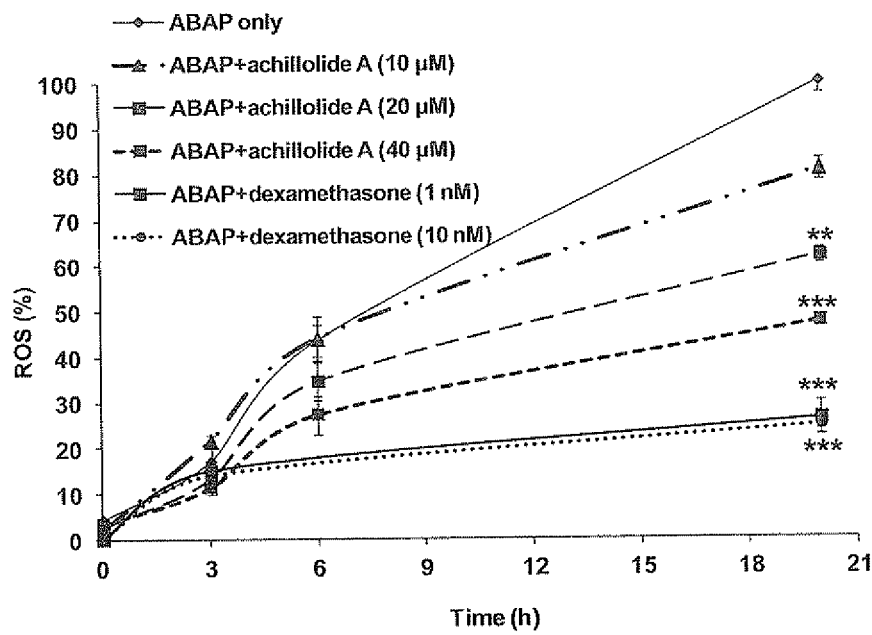
FIG. 25 shows that achillolide A inhibits the peroxyl radical-induced oxidation of DCFH in microglial cells.
Figure 26:
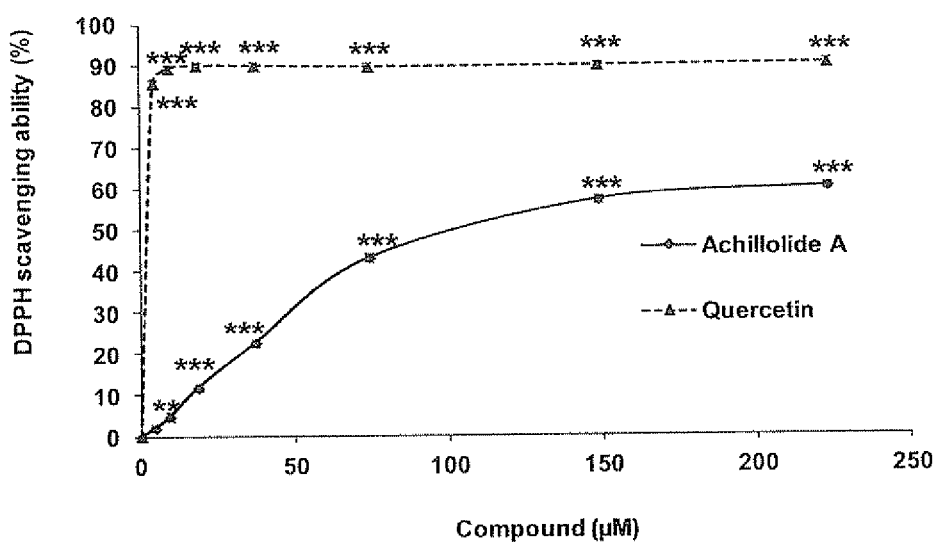
FIG. 26 shows DPPH radical scavenging activity of achillolide A.

In order to measure the ability of achillolide A to penetrate the cell membrane and prevent the formation of DCF by 2,2'-Azobis(amidinopropane) (ABAP)-generated peroxyl radicals, the cellular antioxidant activity assay was used. In this assay, the efficiency of cellular uptake, combined with the radical-scavenging activity of the compound dictates the efficacy of the tested compound in reducing the levels of intracellular radicals. The kinetics of DCFH oxidation by peroxyl radicals generated from ABAP was studied in microglial cells and the results are presented in FIG. 25. As shown in this Figure, ABAP generated radicals in a time-dependent manner, and treatment of cells with achillolide A moderated (54% inhibition) the increase in reactive oxygen species (ROS)-induced fluorescence. As a control drug inventors have tested the effect of dexamethasone on ROS levels produced by ABAP. FIG. 25 shows that dexamethasone was more effective (75% inhibition at nanomolar concentrations) than achillolide A. The ability of achillolide A to scavenge free radicals was also determined in a cell free system using the 2,2-diphenyl-1-pieryhydrazyl (DPPH) radical. In this assay, achillolide A was found to be a free-radical scavenger with an $IC_{50}$ value of 45 µM and 60% maximal scavenging ability (FIG. 26). Quercetin was used as a positive control for radical scavenging ability (90% scavenging activity).

Reagents.

Dulbecco's modified Eagle's medium (DMEM), RPMI-1640 (with or without phenol red), Leibovitz-15 medium, glutamine, antibiotics (10,000 IU/mL penicillin and 10,000 g/mL streptomycin), soybean trypsin inhibitor, fetal bovine serum (FBS) and Dulbecco's phosphate buffered saline (PBS) (without calcium and magnesium) were purchased from Biological Industries (Beit Haemek, Israel); Griess reagent and rabbit anti COX-2 polyclonal antibody were obtained from Cayman chemical, Ml, USA; iNOS polyclonal antibody was purchased from AbD Serotec, Ox, UK; Horseradish peroxidase (HRP)-conjugated anti-rabbit IgG was obtained from Jackson ImmunoResearch Laboratories Inc. Baltimore, USA; Monoclonal mouse anti-β-actin was purchased from MP Biomedicals, Ohio, USA; LPS (*Escherichia coli* 0127 B:8), 2-mercaptoethanol, L-NMMA ($N^G$-Methyl-L-arginine acetate salt), 2,2-Diphenyl-1-pieryl-hydrazyl (DPPH), memantine (≥298%, GC), dexamethasone (≥98%, HPLC), quercetin (≥98%, HPLC), gelatin and crystal violet were purchased from Sigma Chemical Co. (St Louis, Mo., USA). The following kits were used for the assaying gene expression: RNeasy Plus Mini Kit (Qiagen, Hilden, Germany), Thermo Scientific Verso cDNA (Thermo Fisher Scientific Inc), TaqMan Gene Expression Assay from Applied Biosystems.

Plant Material

The aerial parts of Af were collected in the Arava Valley. The plant was authenticated by the botanist Mrs Mimi Ron, The Mount Scopus Botanical Garden in The Hebrew University of Jerusalem, and the voucher specimen has been kept as part of the Arava Rift Valley Plant Collection; VPC (Dead Sea & Arava Science Center, Central Arava Branch, Israel) under the accession code AVPC0040.

Purification of Achillolide A

The dry aerial parts of *Achillea fragrantissima* (37 g) were homogenized and extracted with ethyl acetate (EA; 3×100 mL). Evaporation of the EA gave a brown gum (2.5 g) that was chromatographed on Sephdex LH-20 (2.5 cm×30 cm) eluted with petrol ether/$CH_2Cl_2$/MeOH (2:1:1), 300 mL; ten fractions of 30 mL. Fractions containing achillolide A (TLC, silica, eluted with EA/petrol ether 1:1, $R_f$ 0.5) were combined and evaporated (under vacuum on a rotavapor) to give crude achillolide A, 290 mg. The latter was re-chromatographed by vacuum liquid chromatography (VLC) on silica gel (2 cm×5 cm column bed) eluted with petrol ether EA of increasing polarity (The ethyl acetate percentages was raised by 5% at a time); Fifteen fractions of 25 mL. Achillolide A (90 mg) was obtained from fraction eluted with 30% EA by evaporation of the solvent. Twice crystallization from petrol ether/acetone mixture (prepared by volume), gave pure (98%) achillolide A (40 mg), as was determined by NMR and according to the melting point and optical activity. The structure of the pure molecule is presented in Formula II.

Preparation of Primary Cultures of Microglial Cells.

Cultures of primary rat microglial cells were prepared from cerebral cortices of 1-2 day-old neonatal Wistar rats as described. Microglial cells were seeded at 24-well plastic plates at $1 \times 10^5$/well in RPMI-1640 containing 2% FBS, 2 mM glutamine, 100 U/mL penicillin, 100 g/mL streptomycin, 1 mM sodium pyruvate, and 50 µM β-mercaptoethanol. Cells were cultured for 36 h before treatments. The research was conducted in accordance with the NIH guide for the care and use of laboratory animals, and was approved by the Institutional Animal Care and Use Committee of The Volcani Center, Agricultural Research Organization (IL-135/07, approval date Apr. 11, 2007). All efforts were made to minimize animal suffering, and to reduce the number of animals used.

Quantitative Real-Time PCR Analysis

RNA was extracted by the RNeasy Plus Mini Kit (Qiagen, Hilden, Germany) according to the manufacturer's instructions. Genomic DNA was removed from the RNA samples by using 50 units of RNase-free DNaseI at 37° C. for 1 h. RNA (20 g) was converted to cDNA using the Thermo Scientific Verso cDNA kit (Thermo Fisher Scientific Inc) following the manufacturer's protocol. The cDNA was used for quantitative real-time PCR amplification with TaqMan chemistry (Applied Biosystems) using Rat MMP9, TNFα, IL1β, iNOS, COX2 pre-designed TaqMan Gene Expression Assay from Applied Biosystems (Rn00579162_m1, Rn00562055_m1, Rn00580432_m1, Rn00561646_m1, Rn01483828_m1, respectively). Real time PCR was performed according to the protocol for "assay-on demand" primers (Applied Biosystems). All results from three technical replicates were normalized relative to α-Tubulin (Rn01532518.g1) and GAPDH (Rn01775763.g1), respectively, and expressed as relative expression ratios calculated (relative quantity, RQ) using the comparative method and based on the data that were created by the ABI PRISM 7700 Sequence Detection System (using version 1.6 software).

Nitrite Quantification.

For NO measurements, $1 \times 10^5$ microglial cells/well were plated in a 24-well tissue culture plate. Cells were stimulated with LPS (4.5 ng/mL) and concomitantly treated with achillolide A or a reference drug. NO levels in the culture medium were estimated with Griess reagent.

Measurement of Glutamate Levels in Conditioned Media.

For glutamate measurements, $3.5 \times 10^4$ cells/well were plated on a 24-well tissue culture plate. After 24 h of incubation in DMEM containing 10% FBS, cells were stimulated with LPS (100 ng/mL) and treated with different concentrations of achillolide A. Conditioned media were collected twenty hours later, and were tested for glutamate levels using a colorimetric enzymatic assay kit (glutamate assay kit, BioVision, CA, USA) according to the manufacturer's instructions.

Measurement of IL-1β Levels in Conditioned Media.

For IL-1β measurements, $3.5 \times 10^4$ cells/well were plated on a 24-well tissue culture plate. After 24 h of incubation in DMEM containing 10% FBS, cells were stimulated with LPS (100 ng/mL) and treated with different concentrations of achillolide A. Conditioned media were collected twenty four hours later, and were tested with a rat IL1β ELISA kit (Novus Biologicals; CO, USA), according to the manufacturer's instructions.

Determination of MMP Activities in Conditioned Media of Microglial Cells. MMP-9 activity was quantified by gelatin zymography.

Determination of Cell Viability

Cell viability was determined using a commercial colorimetric assay (Roche Applied Science, Germany) which measures Lactate Dehydrogenase (LDH) activity released from the cytosol of damaged cells into the incubation medium. The absorbance was measured at 492 nm in a plate reader. The percentage of cytotoxicity was calculated according to the following equation, where the LDH activity released from the untreated cells is the spontaneous LDH release, and the maximum releasable LDH in the cells is the:

$$\text{Cytotoxicity (\%)} = \frac{A_{treated\ cells} - A_{untreated\ cells}}{A_{Triton-x\ treated\ cells} - A_{untreated\ cells}} \times 100$$

In MMP-9 experiments and in the cellular antioxidant activity (CAA) assays, cell viability was determined by a modification of the crystal violet assay.

Determination of Cellular Antioxidant Activity (CAA).

Intracellular ROS production was detected using the non-fluorescent cell permeating compound, 2'7'-dichlorofluorescein diacetate (DCF-DA). DCF-DA is hydrolyzed by intracellular esterases and then oxidized by ROS to a fluorescent compound 2'-7'-DCF. Peroxyl radicals are generated by thermolysis of 2,2'-Azobis(amidinopropane) (ABAP) at physiological temperature. ABAP decomposes at approximately $1.36 \times 10^{-6} s^{-1}$ at 37° C., producing at most $1 \times 10^{12}$ radicals/mL/s. Microglial cells (130,000 cells/well) were plated in DMEM containing 2% FBS, 8.4 mM HEPES, 2 mM glutamine, 100 U/mL penicillin and 100 µg/mL streptomycin, onto 24 wells plates. In order to measure the ability of achillolide A to enter the cells and prevent the formation of DCF by ABAP-generated peroxyl radicals, cells were incubated for 1 h with achillolide A. Then cells were preloaded with DCF-DA for 30 min, washed twice with PBS, and ABAP (0.6 mM final concentration) was then added. The fluorescence, which indicates ROS levels, was measured in a plate reader with excitation at 485 nm and emission at 520 nm.

Determination of the Free Radical Scavenging Activity in the DPPH Assay.

Antioxidant activity was measured using the 2,2-diphenyl-1-pieryhydrazyl (DPPH) radical scavenging assay. Different dilutions of achillolide A or quercetin were added to 1 mL of DPPH (3.9 mg/100 mL methanol) in test tubes wrapped in aluminum foil. Absorbance (A) was measured at 517 nm after 8 min incubation in the dark. The scavenging ability (%) of the samples was calculated as $(A_{control} - A_{sample})/A_{control} \times 100)$.

Data Analysis.

Statistical analyses of replicates from pooling of several comparable experiments were performed with one-way ANOVA followed by Tukey-Kramer multiple comparison tests using Graph Pad InStat 3 for windows (GraphPad Software, San Diego, Calif., USA). For PCR experiments—statistical analysis was performed by Student's t-test.

According to the present invention, achillolide A exhibits effects of on cultured neuronal cell.

Figure 27A:
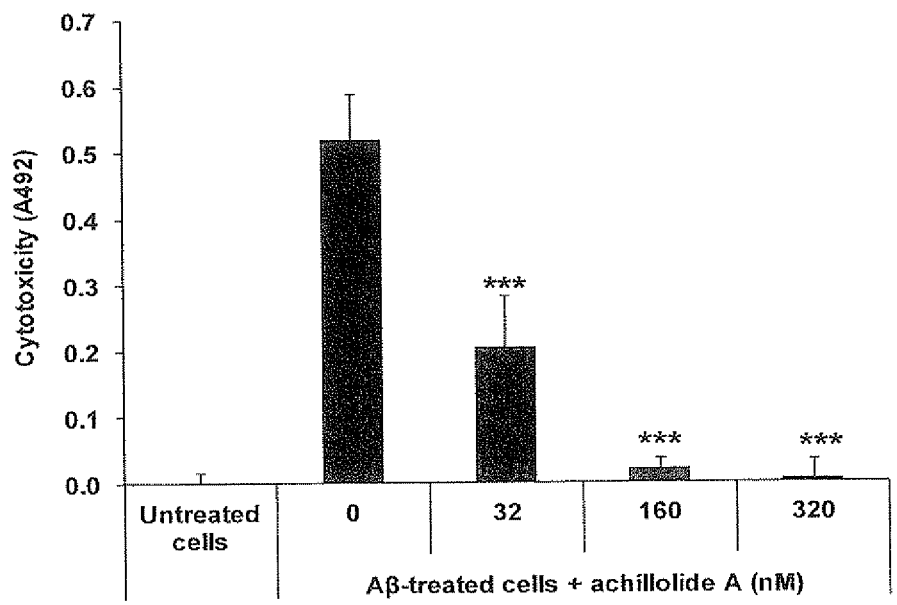
FIGS. 27A-C show that achillolide A (AcA) prevents the $A\beta_{25-35}$-induced neuronal cell death and reactive oxygen species (ROS) elevation.
Figure 27B:
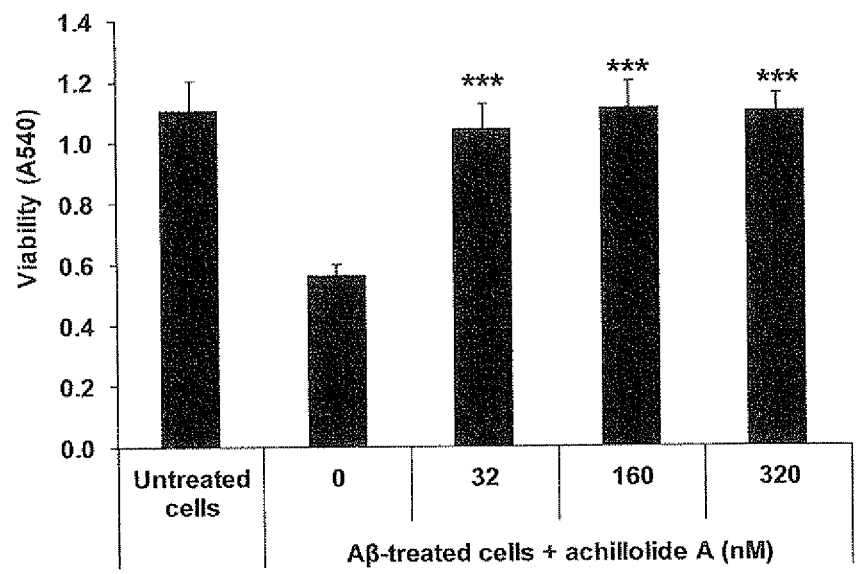

In one embodiment, Amyloid beta$_{25-35}$ (Aβ$_{25-35}$)-induced neuronal cell death. Inventors have examined the effect of achillolide A on neuronal viability following cell treatment with the cytotoxic peptide amyloid beta$_{25-35}$ (Aβ$_{25-35}$). Treatment of neuronal cells with Aβ$_{25-35}$ causes cytotoxicity [as was measured by the LDH method (FIG. 27A) and by the crystal violet staining (FIG. 27B)]. As demonstrated in FIG. 27, achillolide A prevents the cytotoxic effect at nanomolar concentrations.

In another embodiment, this invention relates to Aβ$_{25-35}$-induced reactive oxygen species (ROS) elevation.

Figure 27C:
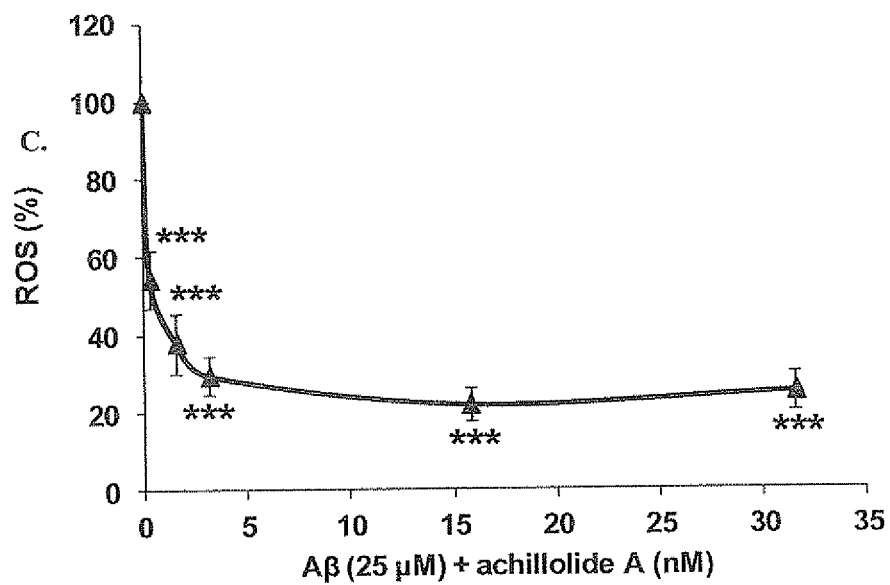

In another embodiment, there is the effect of achillolide A on ROS levels induced by Aβ$_{25-35}$. Treatment of neuronal cells with Aβ$_{25-35}$ causes elevation in ROS levels, and treatment with achillolide A prevents the elevation in ROS levels (FIG. 27C).

This invention further relates to Aβ$_{25-35}$-induced SAPK/JNK phosphorylation. There is an effect of achillolide A on signaling pathways induced by Aβ$_{25-35}$. Treatment of neuronal cells with Aβ$_{25-35}$ causes the phosphorylation of stress-activated protein kinase/Jun-amino-terminal kinase (SAPK/JNK). Achillolide A significantly decreased Aβ$_{25-35}$-induced phosphorylation of SAPK/JNK (FIG. 28) and ERK1/2 (FIG. 29) but not of MEK1 (FIG. 30) in N2a neuronal cells, without affecting the total amount of each of these proteins. Thus, the protective effects of achillolide A on N2a cells might be partially attributed to the inhibition of SAPK/JNK and ERK1/2 phosphorylation.

Figure 31:
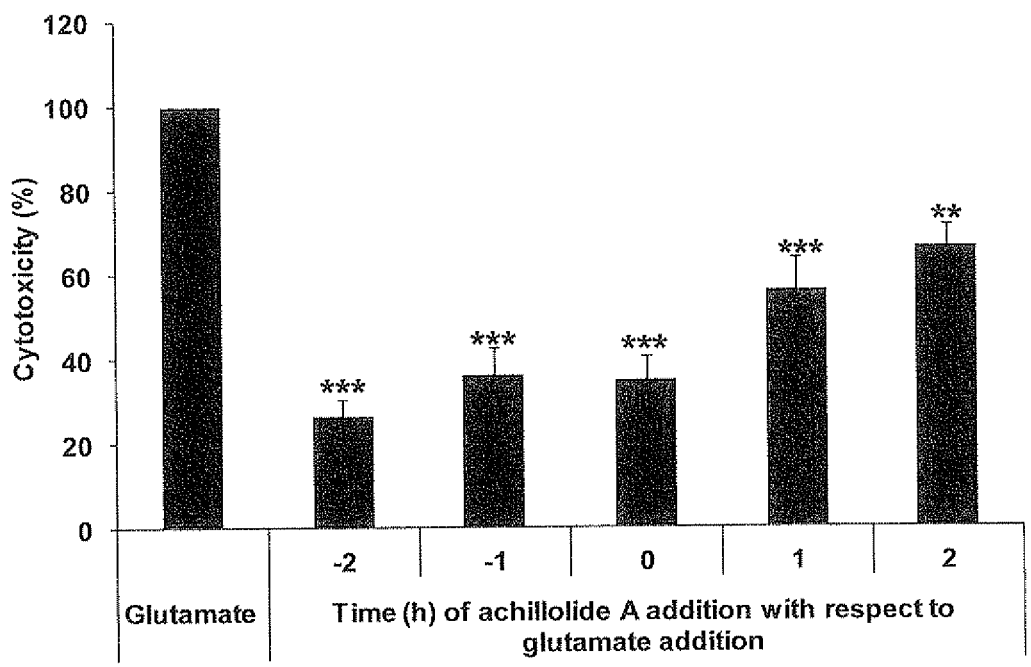
FIG. 31 shows that achillolide A prevents N2a neuronal cells from glutamate-induced cell death.
Figure 32:
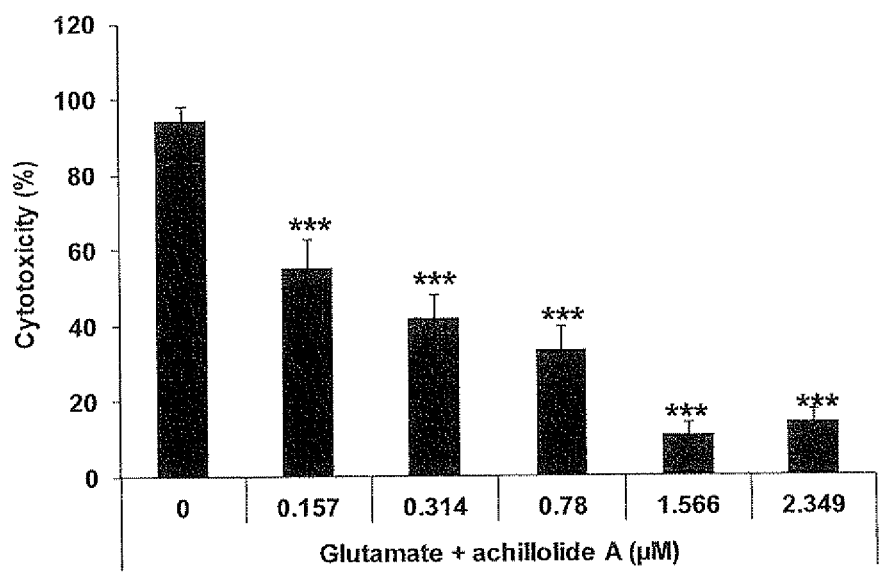
FIG. 32 shows that achillolide A protects the glutamate-induced neuronal cell death.
Figure 33:
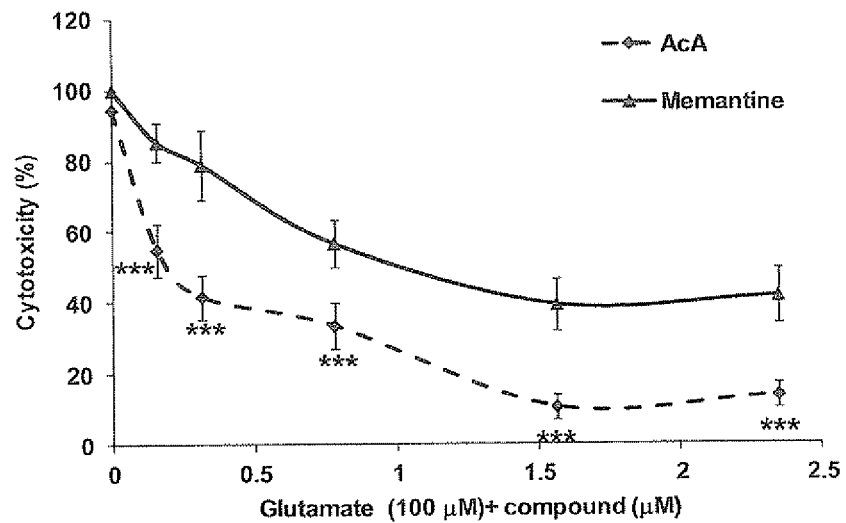
FIG. 33 shows that achillolide A protects the glutamate-induced neuronal cell death.

This invention further relates to Glutamate-induced neuronal cell death. Inventors have examined the effect of achillolide A on neuronal viability following cell treatment with glutamate. Treatment of neuronal cells with glutamate causes cytotoxicity as was measured by the LDH method (FIG. 31-33), and achillolide A prevents the cytotoxic effect at nanomolar concentrations (FIGS. 32, 33).

Figure 34:
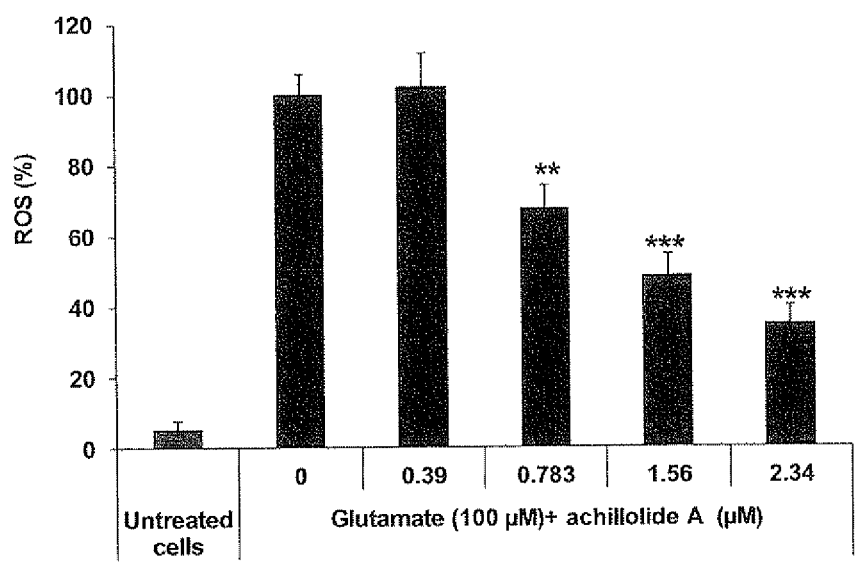
FIG. 34 shows that Achillolide A prevents the glutamate-induced reactive oxygen species (ROS) elevation in N2a cells.
Figure 35:
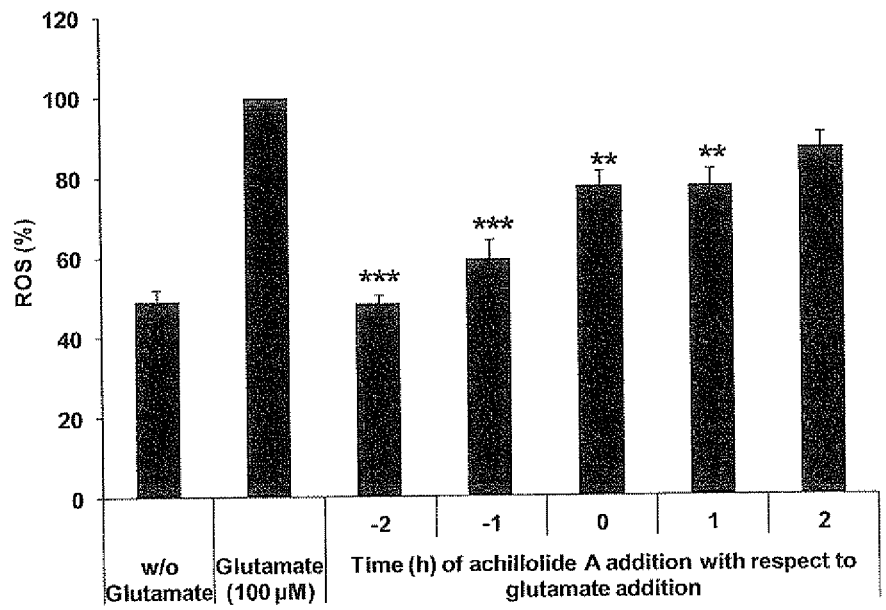
FIG. 35 shows that achillolide A prevents glutamate-induced ROS elevation in N2a neuronal cells.

This invention further relates to Glutamate-induced reactive oxygen species (ROS) elevation. Inventors next examined the effect of achillolide A on ROS levels induced by glutamate. Treatment of neuronal cells with glutamate causes elevation in ROS levels, and treatment with achillolide A prevents the elevation in ROS levels (FIGS. 34, 35).

Enabling Procedures

Procedure 1. Inhibitory Activity Against $H_2O_2$-Induced SAPK/JNK Activation in Cultured Astrocytes In order to determine whether TTF or AcA of the invention gains an inhibitory activity against $H_2O_2$-induced SAPK/JNK activation in cultured astrocytes, a person skilled in the art should follow the following steps:

1. Produce a primary culture of rat brain glial cells according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Incubate the cultured astrocytes (37° C., 5% CO2) for 2 hours with freshly diluted TTF or AcA of the invention;
4. Add 175 micromolars of freshly diluted $H_2O_2$;
5. Incubate the culture for 40 min (37° C., 5% CO2);
6. Prepare cell homogenates and measure protein levels.
7. Measure the amount of total and phosphorylated SAPK/JNK in cell lysates (7-9 micrograms of protein) of astrocytes, by ELISA using the PathScan total SAPK/JNK sandwich ELISA kit (Cell Signaling TECHNOLOGY) and the PathScan phosoho-SAPK/JNK (Thr183/Tyr185) sandwich ELISA kit (Cell Signaling TECHNOLOGY), respectively, according to the manufacturer's instructions.
8. Determine the optical density at 450 nm using a microplate reader.

Procedure 2. Inhibitory Activity Against $H_2O_2$-Induced ERK 1/2 Activation in Cultured Astrocytes In order to determine whether a TTF or AcA of the invention gains an inhibitory activity against $H_2O_2$-induced ERK 1/2 activation in cultured astrocytes, a person skilled in the art should follow the following steps:

1. Produce a primary culture of rat brain glial cells according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Incubate the cultured astrocytes (37° C., 5% CO2) for 2 hours with freshly diluted TTF or AcA of the invention;
4. Add 175 micromolars of freshly diluted $H_2O_2$;
5. Incubate the culture for 40 min (37° C., 5% CO2);
6. Prepare cell homogenates and measure protein levels.
7. Measure the amount of total and phosphorylated ERK 1/2 in cell lysates (9 micrograms) of astrocytes, by ELISA using the PathScan total p44/42 MAPK (ERK 1/2) sandwich ELISA kit (Cell Signaling TECHNOLOGY) or the PathScan phosoho-p44/42 MAPK (Thr202/Tyr204) sandwich ELISA kit (Cell Signaling TECHNOLOGY), respectively.
8. Determine the optical density at 450 nm using a microplate reader.

Procedure 3. Inhibitory Activity Against $H_2O_2$-Induced MEK1 Activation in Cultured Astrocytes In order to determine whether a TTF or AcA of the invention gains an inhibitory activity against $H_2O_2$-induced MEK1 activation in cultured astrocytes, a person skilled in the art should follow the following steps:

1. Produce a primary culture of rat brain glial cells according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Incubate the cultured astrocytes (37° C., 5% CO2) for 2 hours with freshly diluted TTF or AcA of the invention;
4. Add 175 micromolars of freshly diluted $H_2O_2$;
5. Incubate the culture for 40 min (37° C., 5% CO2);
6. Prepare cell homogenates and measure protein levels.
7. Measure the amount of total and phosphorylated MEK1 in cell lysates (8.3-11.7 micrograms) of astrocytes, by ELISA using the PathScan total MEK1 sandwich ELISA kit (Cell Signaling TECHNOLOGY) or the PathScan phosoho-MEK1 (Ser217/221) sandwich ELISA kit (Cell Signaling TECHNOLOGY), respectively.
8. Determine the optical density at 450 nm using a microplate reader.

Procedure 4. Inhibitory Activity Against $H_2O_2$-Induced CREB Activation in Cultured Astrocytes In order to determine whether a TTF or AcA of the invention gains an inhibitory activity against $H_2O_2$-induced CREB activation in cultured astrocytes, a person skilled in the art should follow the following steps:

1. Produce a primary culture of rat brain glial cells according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Incubate the cultured astrocytes (37° C., 5% CO2) for 2 hours with freshly diluted TTF or AcA of the invention;
4. Add 175 micromolars of freshly diluted $H_2O_2$;
5. Incubate the culture for 40 min (37° C., 5% CO2);
6. Prepare cell homogenates and measure protein levels.

7. Measure the amount of total and phosphorylated CREB in cell lysates (14 micrograms) of astrocytes, by ELISA using the PathScan total CREB sandwich ELISA kit (Cell Signaling TECHNOLOGY) or the PathScan phosoho-CREB (Ser133) sandwich ELISA kit (Cell Signaling TECHNOLOGY), respectively.

8. Determine the optical density at 450 nm using a microplate reader.

Procedure 5. Protective Activity Against $H_2O_2$-Induced Cell Death in Cultured Astrocytes.

In order to determine whether a TTF or AcA of the invention gains a protective activity against $H_2O_2$-induced cell death in cultured astrocytes, a person skilled in the art should follow the following steps:

1. Produce a primary culture of rat brain glial cells according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Incubate the cultured astrocytes (37° C., 5% CO2) for 2 hours with freshly diluted TTF or AcA of the invention;
4. Add 175-200 micromolars of freshly diluted $H_2O_2$;
5. Incubate the culture for 20-24 hr (37° C., 5% CO2);
6. Measure cell cytotoxicity and viability by the colorimetric lactate dehydrogenase (LDH) assay (Roche Applied science) according to the manufacturer's instructions, and the crystal violet cell staining as follows:
7. Gently draw out medium from plate;
8. Transfer plate to a chemical hood;
9. Dispense 150 µl 5% formaldehyde (in PBS) to each well and incubate 15 min at RT;
10. Pour out formaldehyde to chemical waste and gently rinse under running tap water;
11. Remove excess water by tapping plate on a tissue paper;
12. Dispense 150 µl crystal violet solution (10 gr/liter, in water) to each well;
13. Incubate 15 min at RT (in the chemical hood);
14. Pour out crystal violet to chemical waste and gently rinse under running tap water until all residual dye is removed;
15. Tap plate on a tissue paper to remove remaining water;
16. Dispense 150 µl 33% aqueous glacial acetic acid to each well;
17. Measure absorbance using a microplate reader at 540 nm with 690 nm reference filter;
18. A reduction of 90% of cytotoxicity levels are indication for a protective activity in this assay.

Procedure 6. Intracellular ROS Reducing Activity.

In order to determine whether a TTF or AcA of the invention reduces ROS levels in $H_2O_2$-treated cultured astrocytes, a person skilled in the art may take the following steps:

1. Produce a primary culture of rat brain glial cells according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Plate astrocytes (300,000 cells/0.5 ml/well of 24 wells plate) and incubate (37° C., 5% CO2) for 24 hr as described in: Elmann, A., et al., (2011). Extract of *Achillea fragrantissima* downregulates ROS production and protects astrocytes from oxidative-stress-induced cell death. In: "Neurodegenerative Diseases—Processes, Prevention, Protection and Monitoring", ISBN 978-953-307-485-6, (Raymond Chuen-Chung Chang, ed). InTech Publisher. http://www.intechopen.com/articles/show/title/extract-of-achillea-fragrantissima-downregulates-ros-production-and-protects-astrocytes-from-oxidati;
4. Replace growth medium with a fresh one containing 20 micromolars 2'7'-dichlorofluorescein diacetate (DCF-DA);
5. Incubate 30 min (37° C., 5% CO2);
6. Wash twice with PBS;
7. Replace with fresh medium;
8. Read fluorescence of "time 0" at 485 nm (Extinction) and 528 nm (Emmision).
9. Incubate the cultured cells for 2 hours with freshly diluted TTF or AcA of the invention;
10. Add freshly diluted $H_2O_2$ (175 micromolars);
11. Read fluorescence at 1, 2, 3, 4 hr after the addition of $H_2O_2$ (Ex: 485 nm and Em: 528 nm).
12. A reduction of 90% of ROS levels are indication for an anti-oxidant activity in this assay.

Procedure 7. Anti-Oxidant Activity in Cultured Astrocytes Containing the Peroxyl Radical Generating Molecule ABAP.

In order to determine whether a TTF or AcA gains an intracellular anti-oxidant activity in cultured astrocytes containing the peroxyl radical generating molecule ABAP, a person skilled in the art may take the following steps:

1. Plate cells in 24 wells plates (300,000 cells/well).
2. The day after replace medium with fresh medium as described in: Elmann, A., Telerman, A., Mordechay, S., Erlank, H., Rindner, M., Ofir, R. and Beit-Yannai, E. (2011). Extract of *Achillea fragrantissima* downregulates ROS production and protects astrocytes from oxidative-stress-induced cell death. In: "Neurodegenerative Diseases—Processes, Prevention, Protection and Monitoring", ISBN 978-953-307-485-6, (Raymond Chuen-Chung Chang, ed). InTech Publisher:
21
http://www.intechopen.com/articles/show/title/extract-of-achillea-fragrantissima-downregulates-ros-production-and-protects-astrocytes-from-oxidati;
3. Incubate cells with freshly diluted TTF or AcA of the invention (1 hr, 5% CO2, 370 C);
4. Add DCF-DA and incubate cells for additional 30 min (37° C., 5% CO2);
5. Wash twice with PBS;
6. Read "time 0" fluorescence (Ex: 485 nm and Em: 528 nm);
7. Add to cells freshly diluted 2'2'-azobis(2-amidinopropane) dihydrochloride (ABAP, generate peroxyl radicals) to a final concentration of 600 microM, except of "blank" cells (cells w/o antioxidants and w/o ABAP);
8. Read fluorescence at 3, 6, and 24 hr Ex: 485 nm and Em: 528 nm;
9. Measure cell viability 20 hr later using the crystal violet cell staining as described above;

10. A reduction of at least 60% of ROS levels are indication for anti-oxidant activity in the cellular anti-oxidant assay (See Wolfe, K. L., & Liu R. H. (2007) Cellular antioxidant activity (CAA) assay for assessing antioxidants, foods, and dietary supplements. *Journal of Agriculture and Food Chemistry*, Vol. 55, No. 22, pp. 8896-8907.).

Procedure 8. Anti-Inflammatory Activity in LPS-Activated Microglial Cells.

In order to determine whether a TTF or AcA of the invention gains an anti-inflammatory activity in LPS-activated microglial cells, a person skilled in the art may take the following steps:
1. Prepare a primary culture of microglial cells as described in "Anti-neuroinflammatory effects of geranium oil in microglial cells" 2010. A. Elmann, S. Mordechay, M. Rindner, U. Ravid. Journal of functional foods. 2:17-22;
2. Plate microglial cells ($3.5 \times 10^4$ cells/well) on a 24-well tissue culture plate, in DMEM containing 10% FBS, 2 mM glutamine, 100 U/ml penicillin and 100 micrograms/mL streptomycin;
4. Treat cells with freshly diluted TTF or AcA of the invention;
5. Activate microglial cells with lipopolysaccharide (LPS, 100 nanograms/mL);
6. Collect conditioned media after 24 hr for the measurement of IL-1β and IL-6 levels;
7. Measure the levels of cytokines by ELISA;
8. Inhibition higher than 45% of the induced IL-6 and of 85% of the induced IL-1β□ are indications for anti-inflammatory activity in this model.

Procedure 9. Viability of Microglial Cells.
In order to determine whether a TTF or AcA of the invention is not toxic to LPS-activated microglial cells, a person skilled in the art may take the following steps:
1. Prepare a primary culture of microglial cells as described in "Anti-neuroinflammatory effects of geranium oil in microglial cells" 2010. A. Elmann, S. Mordechay, M. Rindner, U. Ravid. Journal of functional foods. 2:17-22;
2. Plate microglial cells ($3.5 \times 10^4$ cells/well) on a 24-well tissue culture plate, in DMEM containing 10% FBS, 2 mM glutamine, 100 U/ml penicillin and 100 micrograms/ml streptomycin;
4. Treat cells with freshly diluted TTF or AcA of the invention;
5. Activate microglial cells with lipopolysaccharide (LPS, 100 nanograms/ml);
6. Collect conditioned media after 24 hr for different assays (e.g. cytokines or glutamate levels)
and measure cell viability by the crystal violet cell staining as follows:
7. Transfer plate to a chemical hood;
8. Dispense 150 μl 5% formaldehyde (in PBS) to each well and incubate 15 min at RT;
9. Pour out formaldehyde to chemical waste and gently rinse under running tap water;
10. Remove excess water by tapping plate on a tissue paper;
11. Dispense 150 μl crystal violet solution (10 gr/liter, in water) to each well;
12. Incubate 15 min at RT (in the chemical hood);
13. Pour out crystal violet to chemical waste and gently rinse under running tap water until all residual dye is removed;
14. Tap plate on a tissue paper to remove remaining water;
15. Dispense 150 μl 33% aqueous glacial acetic acid to each well;
16. Measure absorbance using a microplate reader at 540 nm with 690 nm reference filter;
17. Viability which is not lower than the viability of untreated cells is considered as not toxic in this assay.

Procedure 10. Inhibitory Activity Against Aβ25-35-Induced SAPK/JNK Activation in Cultured N2a Cells.

In order to determine whether a TTF or AcA of the invention gains an inhibitory activity against Aβ25-35-induced SAPK/JNK activation in cultured N2a cells, a person skilled in the art should follow the following steps:
1. Solubilize $A\beta_{25-35}$ in sterile double distilled water to a final concentration of 2 millimolars, and incubate for 24 hours at 37° C. in a water bath.
2. Grow N2a cells in DMEM (high glucose, 225 ml), Opti-MEM (250 ml) containing 5% Fetal Bovine Serum, 2 mM L-Glutamine, 100 U/ml penicillin and 100 micrograms/mL streptomycin
3. Incubate the cultured N2a cells (37° C., 5% CO2) for 2 hours with freshly diluted TTF or AcA of the invention;
4. Add 25 micromolars of freshly diluted Aβ25-35;
5. Incubate the culture for 40 min (37° C., 5% CO2);
6. Prepare cell homogenates and measure protein levels.
7. Measure the amount of total and phosphorylated SAPK/JNK in cell lysates) of N2a cells, by ELISA using the PathScan total SAPK/JNK sandwich ELISA kit (Cell Signaling TECHNOLOGY) and the PathScan phosoho-SAPK/JNK (Thr183/Tyr185) sandwich ELISA kit (Cell Signaling TECHNOLOGY), respectively, according to the manufacturer's instructions.
8. Determine the optical density at 450 nm using a microplate reader.

Procedure 11. Inhibitory Activity Against Aβ25-35-Induced ERK 1/2 Activation in Cultured N2a Cells.

In order to determine whether a TTF or AcA of the invention gains an inhibitory activity against Aβ25-35-induced ERK 1/2 activation in cultured N2a cells, a person skilled in the art should follow the following steps:
1. Solubilize $A\beta_{25-35}$ in sterile double distilled water to a final concentration of 2 millimolars, and incubate for 24 hours at 37° C. in a water bath.
2. Grow N2a cells in DMEM (high glucose, 225 ml), Opti-MEM (250 ml) containing 5% Fetal Bovine Serum, 2 mM L-Glutamine, 100 U/ml penicillin and 100 micrograms/mL streptomycin
3. Incubate the cultured N2a cells (37° C., 5% CO2) for 2 hours with freshly diluted TTF or AcA of the invention;
4. Add 25 micromolars of freshly diluted Aβ25-35;
5. Incubate the culture for 40 min (37° C., 5% CO2);
6. Prepare cell homogenates and measure protein levels.
7. Measure the amount of total and phosphorylated ERK 1/2 in cell lysates of N2a cells, by ELISA using the PathScan total p44/42 MAPK (ERK 1/2) sandwich ELISA kit (Cell Signaling TECHNOLOGY) or the PathScan phosoho-p44/42 MAPK (Thr202/Tyr204) sandwich ELISA kit (Cell Signaling TECHNOLOGY), respectively.
8. Determine the optical density at 450 nm using a microplate reader.

Procedure 12. Inhibitory Activity Against Aβ25-35-Induced MEK1 Activation in Cultured N2a Cells.

In order to determine whether a TTF or AcA of the invention gains an inhibitory activity against Aβ25-35-induced MEK1 activation in cultured N2a cells, a person skilled in the art should follow the following steps:
1. Solubilize $A\beta_{25-35}$ in sterile double distilled water to a final concentration of 2 millimolars, and incubate for 24 hours at 37° C. in a water bath.

2. Grow N2a cells in DMEM (high glucose, 225 ml), Opti-MEM (250 ml) containing 5% Fetal Bovine Serum, 2 mM L-Glutamine, 100 U/ml penicillin and 100 micrograms/mL streptomycin
3. Incubate the cultured N2a cells (37° C., 5% CO2) for 2 hours with freshly diluted TTF or AcA of the invention;
4. Add 25 micromolars of freshly diluted Aβ25-35;
5. Incubate the culture for 40 min (37° C., 5% CO2);
6. Prepare cell homogenates and measure protein levels.
7. Measure the amount of total and phosphorylated MEK1 in cell lysates of N2a cells, by ELISA using the PathScan total MEK1 sandwich ELISA kit (Cell Signaling TECHNOLOGY) or the PathScan phosoho-MEK1 (Ser217/221) sandwich ELISA kit (Cell Signaling TECHNOLOGY), respectively.
8. Determine the optical density at 450 nm using a microplate reader.

Procedure 13. Inhibitory Activity Against Aβ25-35-Induced CREB Activation in Cultured N2a Cells.

In order to determine whether a TTF or AcA of the invention gains an inhibitory activity against Aβ25-35-induced CREB activation in cultured N2a cells, a person skilled in the art should follow the following steps:
1. Solubilize $Aβ_{25-35}$ in sterile double distilled water to a final concentration of 2 millimolars, and incubate for 24 hours at 37° C. in a water bath.
2. Grow N2a cells in DMEM (high glucose, 225 ml), Opti-MEM (250 ml) containing 5% Fetal Bovine Serum, 2 mM L-Glutamine, 100 U/ml penicillin and 100 micrograms/mL streptomycin
3. Incubate the cultured N2a cells (37° C., 5% CO2) for 2 hours with freshly diluted TTF or AcA of the invention;
4. Add 25 micromolars of freshly diluted Aβ25-35;
5. Incubate the culture for 40 min (37° C., 5% CO2);
6. Prepare cell homogenates and measure protein levels.
7. Measure the amount of total and phosphorylated CREB in cell lysates of N2a cells, by ELISA using the PathScan total CREB sandwich ELISA kit (Cell Signaling TECHNOLOGY) or the PathScan phosoho-CREB (Ser133) sandwich ELISA kit (Cell Signaling TECHNOLOGY), respectively.
8. Determine the optical density at 450 nm using a microplate reader.

Procedure 14. Inhibitory Activity Against Glutamate-Induced Neuronal Cell Death.

In order to determine whether a TTF or AcA of the invention gains an inhibitory activity against glutamate-induced cell death in cultured neuronal cells, a person skilled in the art should follow the following steps:
Grow N2a cells in DMEM (high glucose, 225 ml), Opti-MEM (250 ml) containing 1% Fetal Bovine Serum, 2 mM L-Glutamine, 100 U/ml penicillin and 100 micrograms/mL streptomycin.
Treat N2a neuronal cells with AcA or TTF.
Two hr later add 100 micromolars of freshly diluted glutamate;
Incubate the culture for 20 hr (37° C., 5% CO2);
Measure cytotoxicity by the LDH method
Measure viability by the crystal violet staining.

Procedure 15. Intracellular $Aβ_{25-35}$-Induced ROS Reducing Activity.

In order to determine whether a TTF or AcA of the invention reduces $Aβ_{25-35}$-induced ROS levels in N2a cells, a person skilled in the art may take the following steps:
1. Solubilize $Aβ_{25-35}$ in sterile double distilled water to a final concentration of 2 millimolars, and incubate for 24 hours at 37° C. in a water bath.
2. Plate N2a cells (10,000 cells/0.2 ml/well of 96 wells plate) in DMEM (high glucose, 225 ml), Opti-MEM (250 mil) containing 5% Fetal Bovine Serum, 2 mM L-Glutamine, 100 U/ml penicillin and 100 micrograms/mL streptomycin and incubate (37° C., 5% CO2) for 24 hr.
3. Replace the medium with a fresh one containing 20 micromolars 2'7'-dichlorofluorescein diacetate (DCF-DA);
4. Incubate 30 min (37° C., 5% CO2);
5. Wash twice with PBS;
6. Replace with fresh medium;
7. Read fluorescence of "time 0" at 485 nm (Extinction) and 528 nm (Emmision).
8. Incubate the cultured cells for 2 hours with freshly diluted TTF or AcA of the invention;
9. Add freshly diluted Aβ25-35 (25 micromolars);
10. Read fluorescence at 20 hr after the addition of Aβ25-35 (25 micromolars) (Ex: 485 nm and Em: 528 nm).
11. A reduction of 70% of ROS levels are indication for an anti-oxidant activity in this assay.

Procedure 16. Intracellular glutamate-induced ROS reducing activity.

In Order to Determine Whether a TTF or AcA of the Invention Reduces Glutamate-Induced ROS levels in N2a cells, a person skilled in the art may take the following steps:
1. Plate N2a cells (10,000 cells/0.2 ml/well of 96 wells plate) in DMEM (high glucose, 225 ml), Opti-MEM (250 ml) containing 1% Fetal Bovine Serum, 2 mM L-Glutamine, 100 U/ml penicillin and 100 micrograms/mL streptomycin and incubate (37° C., 5% CO2) for 24 hr.
2. Replace growth medium with a fresh one containing 20 micromolars 2'7'-dichlorofluorescein diacetate (DCF-DA);
3. Incubate 30 min (37° C., 5% CO2);
4. Wash twice with PBS;
5. Replace with fresh medium;
6. Read fluorescence of "time 0" at 485 nm (Extinction) and 528 nm (Emmision).
7. Incubate the cultured cells for 2 hours with freshly diluted TTF or AcA of the invention;
8. Add freshly diluted glutamate (100 micromolars);
9. Read fluorescence at 20 hr after the addition of glutamate (100 micromolars) (Ex: 485 nm and Em: 528 nm).
10. A reduction of 55% of ROS levels are indication for an anti-oxidant activity in this assay.

Procedure 17. Inhibitory Activity Against Aβ25-35-Induced Neuronal Cell Death.

In order to determine whether a TTF or AcA of the invention gains an inhibitory activity against $Aβ_{25-35}$-induced cell death in cultured neuronal cells, a person skilled in the art should follow the following steps:
Solubilize $Aβ_{25-35}$ in sterile double distilled water to a final concentration of 2 millimolars, and incubate for 24 hours at 37° C. in a water bath.
Grow N2a cells in DMEM (high glucose, 225 ml), Opti-MEM (250 ml) containing 5% Fetal Bovine Serum, 2 mM L-Glutamine, 100 U/ml penicillin and 100 micrograms/mL streptomycin.
Treat N2a neuronal cells with 25 micromolars of freshly diluted Aβ25-35 in the presence or absence of AcA or TTF.
Incubate the culture for 20 hr (37° C., 5% CO2);
Measure cytotoxicity by the LDH method
Measure viability by the crystal violet staining.

Procedure 18. Measurement of NO Levels in LPS-Activated Microglial Cells.

In order to determine whether AcA of the invention inhibits NO secretion from LPS-activated microglial cells, a person skilled in the art may take the following steps:

1. Prepare a primary culture of microglial cells and plate cells as described in "Anti-neuroinflammatory effects of geranium oil in microglial cells" 2010. A. Elmann, S. Mordechay, M. Rindner, U. Ravid. Journal of functional foods. 2:17-22;
2. Treat cells with freshly diluted AcA of the invention;
3. Activate microglial cells with lipopolysaccharide (LPS, 4.5 nanograms/mL);
4. Collect 100 microliters of conditioned media after 20 hr for the measurement of NO levels;
5. Measure the levels of NO by mixing with 100 microliters of Griess reagent;
6. Incubate at room temperature for 10 min.
7. Read the absorbance at 550 nm in a microplate reader.
8. Use culture medium as blank.
9. Inhibition higher than 66% of the induced NO □are indications for anti-inflammatory activity in this model;

Procedure 19. Measurement of Glutamate Levels in Conditioned Media of LPS-Activated Microglial Cells.

In order to determine whether AcA of the invention can reduce glutamate secretion from LPS-activated microglial cells, a person skilled in the art may take the following steps:
1. Prepare a primary culture of microglial cells as described in "Anti-neuroinflammatory effects of geranium oil in microglial cells" 2010. A. Elmann, S. Mordechay, M. Rindner, U. Ravid. Journal of functional foods. 2:17-22;
2. Plate microglial cells ($3.5 \times 10^4$ cells/well) on a 24-well tissue culture plate, in DMEM containing 10% FBS, 2 mM glutamine, 100 U/ml penicillin and 100 micrograms/mL streptomycin;
4. Treat cells with freshly diluted AcA of the invention;
5. Activate microglial cells with lipopolysaccharide (LPS, 100 nanograms/mL);
6. Collect conditioned media after 20 hr for the measurement of glutamate levels;
7. Measure the levels of glutamate using a colorimetric enzymatic assay kit (glutamate assay kit, BioVision, CA, USA) according to the manufacturer's instructions.
9. Inhibition higher than 80% of the induced glutamate are indications for anti-inflammatory activity in this model.

Procedure 20. Measurement of MMP-9 Activity in LPS-Activated Microglial Cells.

In order to determine whether AcA of the invention inhibits the levels of active MMP-9 secreted from LPS-activated microglial cells, a person skilled in the art may take the following steps:
1. Prepare a primary culture of microglial cells and plate cells as described in "Anti-neuroinflammatory effects of the extract of *achillea fragrantissima*" 2011. A. Elmann, S. Mordechay, H. Erlank, A. Telerman, M. Rindner, R. Ofir. BMC Complementary and Alternative Medicine. 11:98;
2. Treat cells with freshly diluted AcA of the invention;
3. Activate microglial cells with lipopolysaccharide (LPS, 4.5 nanograms/mL);
4. Measure the levels of MMP-9 by gel zymography as described in "Anti-neuroinflammatory effects of the extract of *achillea fragrantissima*" 2011. A. Elmann, S. Mordechay, H. Erlank, A. Telerman, M. Rindner, R. Ofir. BMC Complementary and Alternative Medicine. 11:98.
5. Inhibition higher than 90% of the induced MMP-9 activity □is an indication for anti-inflammatory activity in this model.

Procedure 21. Anti-Inflammatory Activity in LPS-Activated Splenocytes.

In order to determine whether AcA of the invention gains an anti-inflammatory activity in LPS-activated splenocytes, a person skilled in the art may take the following steps:

1. Sacrifice Balb/c mice by decapitation.
2. Remove spleens from mice, pool, and squeeze to single cell suspension
3. Lyse red blood cells using lysis buffer, and wash cells several times.
4. Plate splenocytes ($5 \times 10^6$ cells/well) on a 24-well tissue culture plate, in DMEM containing 10% FBS, 2 mM glutamine, 100 U/ml penicillin and 100 micrograms/mL streptomycin;
5. Treat cells with freshly diluted AcA of the invention;
6. Activate microglial cells with lipopolysaccharide (LPS, 5 micrograms/mL);
7. Collect conditioned media for the measurement of cytokine levels; IL-2, after 24 h; IFNγ, TNF-α, IL-10, IL-12 and IL-6 after 48 hr.
8. Measure the levels of cytokines by ELISA;
9. Inhibition higher than 50% of the induced cytokines TNF-alpha, Interferon gamma, IL-2, IL-6, IL-10, IL-12 are indications for anti-inflammatory activity in this model.

Procedure 22. Elevation of GDNF Levels in Astrocytes.

In order to determine whether AcA of the invention gains a GDNF-inducing activity in cultured astrocytes, a person skilled in the art should follow the following steps:
1. Produce a primary culture of rat brain glial cells according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Plate astrocytes in 6-wells PDL-coated plastic plates at a density of $2 \times 10^6$ cells/well, in DMEM/F12 containing 5% FBS, 2 millimolar glutamine, 100 U/ml penicillin, and 100 micrograms/ml streptomycin.
4. Incubate the culture for 24 hr (37° C., 5% CO2);
5. Aspirate medium and add fresh medium to the cells.
6. Incubate the cultured astrocytes (37° C., 5% CO2) for 24 hours with freshly diluted AcA of the invention;
7. Lyse cells using RLT buffer (Qiagen, Hilden, Germany) containing 1% beta-mercaptoethanol.
8. Extract RNA and perform real time PCR analysis as described in Elmann, A., Telerman, A., Erlank, H., Mordechay, S., Rindner, M., Ofir, R. and Kashman, Y. (2013) "Protective and antioxidant effects of a chalconoid from *Pulicaria incisa* on brain astrocytes". *Oxidative Medicine and Cellular Longevity:* 2013, Article ID 694398.
9. A two fold induction in GDNF levels are indicative for a GDNF-inducing activity in this assay.

Procedure 23. Measurement of IL-1Beta, TNFalpha, iNOS, COX-2 and MMP-9 Transcripts in LPS-Activated Microglial Cells by Quantitative Real-Time PCR Analysis.
 1. Prepare cultures of primary rat microglial cells as described in "Anti-neuroinflammatory effects of geranium oil in microglial cells" 2010. A. Elmann, S. Mordechay, M. Rindner, U. Ravid. Journal of functional foods. 2:17-22;
 2. Plate microglial cells in RPMI-1640 containing 2% FBS, 2 mM glutamine, 100 U/mL penicilin, 100 μg/mL streptomycin, 1 mM sodium pyruvate, and 50 μM β-mercaptoethanol.

3. Culture cells for 36 h before treatments.
4. Treat microglial cells with achillolide A.
5. Stimulate with LPS (4.5 ng/mL) for 5 hr.
6. Extract RNA by the RNeasy Plus Mini Kit (Oiagen, Hilden, Germany) according to the manufacturer's instructions.
7. Remove genomic DNA from the RNA samples by using 50 units of RNase-free DNaseI at 37° C. for 1 h.
8. Convert RNA (20 µg) to cDNA using the Thermo Scientific Verso cDNA kit (Thermo Fisher Scientific Inc) following the manufacturer's protocol.
9. Use cDNA for quantitative real-time PCR amplification with TaqMan chemistry (Applied Biosystems) using Rat MMP9, TNFα, IL1β, iNOS, COX2 pre-designed TaqMan Gene Expression Assay from Applied Biosystems (Rn00579162_m1, Rn00562055_m1, Rn00580432_m1, Rn00561646_m1, Rn01483828_m1, respectively).
10. Perform real time PCR according to the protocol for "assay-on demand" primers (Applied Biosystems).
11. Normalize results relative to α-Tubulin (Rn01532518.g1) or GAPDH (Rn01775763.g1), and express as relative expression ratios calculated (relative quantity, RQ) using the comparative method and based on the data that were created by the ABI PRISM 7700 Sequence Detection System (using version 1.6 software).

Testable Criteria for Neurodegenerative Conditions

Provided are testable criteria regarding several factors in order to assist the skilled person in assessing whether or not a neurodegenerative condition shown to be improved or prevented by TTF or AcA, indeed involves the affecting of these factors.

In order to show that in case of improvement in a neurodegenerative condition, such improvement is connected to reduction in iNOS, COX-2, IL-1beta, IL-2 and TNFalpha levels by achillolide A, analysis in brains from vehicle or LPS-injected mice should be made in mice after treatment with achillolide A and in mice not treated with achillolide A. Intraperitoneal injection of LPS to mice is followed by a significant increase in the protein levels of iNOS, COX-2, IL-1beta, IL-2 and TNFalpha in mice brains as compared with vehicle controls. Inject LPS, treat with achillolide A, sacrifice mice, remove brains, prepare brain homogenates, and test iNOS, COX-2, IL-1beta, IL-2 and TNFalpha levels by Western blot analysis as described in *Neurobiol Learn Mem.* 2011; 96(2):156-65. Reduction in iNOS, COX-2, IL-1beta, IL-2 and TNFalpha levels in brain homogenates of mice treated with achillolide A indicates that achillolide A administration is the cause for reduction in iNOS, COX-2, IL-1beta, IL-2 and TNFalpha levels.

In order to show that in case of improvement in a neurodegenerative condition, such improvement is connected to reduction in IL-1beta and IL-6 levels by TTF, analysis in brains from vehicle or LPS-injected mice should be made in mice after treatment with TTF and in mice not treated with TTF. Intraperitoneal injection of LPS to mice is followed by a significant increase in the protein levels of IL-1beta in mice brains as compared with vehicle controls. Inject LPS, treat with TTF, sacrifice mice, remove brains, prepare brain homogenates, and test IL-1beta and IL-6 levels by Western blot analysis as described in *Neurobiol Learn Mem.* 2011; 96(2):156-65. Reduction in IL-1beta and IL-6 levels in brain homogenates of mice treated with TTF indicates that TTF administration is the cause for reduction in IL-1beta and IL-6 levels.

In order to show that in case of improvement in a neurodegenerative condition, such improvement is connected to reduction in the levels of ERK1/2, MEK1, CREB and SAPK/JNK phosphorylation by TTF/achillolide A, analysis in brains from vehicle or LPS-injected mice should be made in mice after treatment with TTF/achillolide A and in mice not treated with TTF/achillolide A. Intraperitoneal injection of LPS to mice is followed by a significant increase in the phosphorylation of ERK and JNK in mice brains as compared with vehicle controls. Inject LPS, treat with achillolide A/TTF sacrifice mice, remove brains, prepare brain homogenates, and test the levels of unphosphorylated and phosphorylated levels of ERK1/2, MEK1, CREB and SAPK/JNK by Western blot analysis as described in "Ursolic acid attenuates lipopolysaccharide-induced cognitive deficits in mouse brain through suppressing p38/NF-kB mediated inflammatory pathways. Wang Y J, Lu J, Wu D M, Zheng Z H, Zheng Y L, Wang X H, Ruan J, Sun X, Shan Q, Zhang Z F. Neurobiol Learn Mem. 2011; 96(2):156-65". Reduction in ERK1/2, MEK1, CREB and SAPK/JNK phosphorylation levels in brain homogenates of mice treated with TTF/Achillolide A indicates that TTF/Achillolide A administration is the cause for reduction in ERK and SAPK/JNK phosphorylation levels.

In order to show that in case of improvement in a neurodegenerative condition, such improvement connected to reduction in nitrite (NO) levels by achillolide A, analysis in brains from vehicle or LPS-injected C57BL/6 mice should be made in mice after treatment with achillolide A and in brains of mice not treated with achillolide A. Intraperitoneal injection of LPS to mice is followed by a significant increase in brain nitrite. Inject LPS, treat with achillolide A, sacrifice mice by decapitation, remove brains, wash with ice cold saline solution, weight, homogenize and measure nitrite (NO metabolite) by Griess reagent as described in Abdel-Salam et al. Neurotox Res. 2012; 21(3):245-55. Reduction in nitrite (NO) levels in brain homogenates of mice treated with achillolide A indicates that achillolide A administration is the cause for reduction in nitrite (NO) levels.

In order to show that in case of improvement in neurodegenerative condition, such improvement is connected to reduction in oxidative stress levels by achillolide A/TTF, analysis in brains from 1-methyl-4-phenyl-1,2,3,6-tetrahydropyridine (MPTP)-injected male Swiss albino mice should be made after treatment with achillolide A/TTF and in mice not treated with achillolide A/TTF. Intraperitoneal injection of MPTP to mice is followed by a significant increase in the levels of malondialdehyde (MDA) in the nigrostriatal region of mice brains as compared with vehicle controls. Inject MPTP Intraperitonealy, treat with achillolide A/TTF, sacrifice mice, remove brains, prepare homogenates of nigrostriatal tissue, and test lipid peroxidation levels in the brain nigrostriatal tissues as an indication for oxidative stress using the method described in "Comparison of the neuroprotective potential of *Mucuna pruriens* seed extract with estrogen in 1-methyl-4-phenyl-1,2,3,6-tetrahydropyridine (MPTP)-induced PD mice model. Neurochem Int. 2014; 65:1-13. Yadav S K, Prakash J, Chouhan S, Westfall S, Verma M, Singh T D, Singh S P". Reduction in MDA levels in brain homogenates of mice treated with achillolide A/TTF indicates that achillolide A/TTF administration is the cause for reduction in oxidative stress levels.

In animal models of Parkinson's disease, the experimental results using GDNF have consistently demonstrated neuroprotective effects on dopaminergic neurons.

In order to show that improvement in a neurodegenerative condition is connected to elevation in GDNF levels by achillolide A, analysis of GDNF levels in brains from 1-methyl-4-phenylpyridinium (MPP+)-injected female Sprague Dawley (SD) rats should be made after treatment with achillolide A and in brains of rats not treated with TTF/achillolide A. Unilateral injection of MPP+ into the right median forebrain bundle of rats is followed by a significant decrease in the levels of GDNF in the substantia nigra of rat brains as compared with vehicle controls. Inject MPP+ unilaterally, treat with AcA, sacrifice rat, remove brains, prepare homogenates or brain sections, and test GDNF levels by Western blot analysis and/or by immunofluorescence, respectively, as described in *J Nutr Biochem.* 2014; 25(7):801-6. Elevation in GDNF levels in brain homogenates/sections of MPP+-injected rats treated with achillolide A compared to vehicle-treated MPP+-injected rats indicates that achillolide A administration is the cause for elevation in GDNF levels.

In order to show that in case of improvement in a neurodegenerative condition, such improvement is connected to reduction in MMP-9 levels by achillolide A, analysis in brains from vehicle or 6-hydroxydopamine (6-OHDA)-injected rats should be made in rats after treatment with achillolide A and in rats that were not treated with achillolide A. Injection of 6-OHDA into the medial forebrain bundle results in a significant increase in the number of MMP-9-positive cells in the substantia nigra zona compacta on the lesioned side of the brain compared to unlesioned side at 9 days after administration of 6-OHDA. Inject 6-OHDA to Sprague-Dawley rats, treat with achillolide A, sacrifice rats, remove brains, prepare free-floating sections from the brain and test MMP-9 levels by immunohistochemistry as described in "Broom L, Marinova-Mutafchieva L, Sadeghian M, Davis J B, Medhurst A D, Dexter D T. Free Radic Biol Med. 2011; 50(5):633-40. Neuroprotection by the selective iNOS inhibitor GW274150 in a model of Parkinson disease". Reduction in the number of MMP-9 positive cells in 6-OHDA-lesioned rats treated with achillolide A compared to the vehicle-treated 6-OHDA-lesioned rats indicates that achillolide A administration is the cause for reduction in MMP-9 levels.

In order to show that in case of improvement in a neurodegenerative condition, such improvement is connected to protection of neuronal cells from glutamate toxicity by achillolide A/TTF, analysis in retinal ganglion cells (RGC) from vehicle or glutamate-injected mice should be made in mice after treatment with achillolide A/TTF and in mice not treated with achillolide A/TTF. Injection of glutamate to mice eyes is followed by a significant decrease in RGC survival as compared with vehicle controls. Inject FluoroGold to the superior colliculus of mice. Inject glutamate into the eye, treat with achillolide A/TTF, sacrifice mice after 1 week, enucleate eyes, detach retinas and prepare for microscopic evaluation. Calculate the average number of RGCs perfield in each retina as described in Schori H, Kipnis J, Yoles E, WoldeMussie E, Ruiz G, Wheeler L A, Schwartz M (2001) "Vaccination for protection of retinal ganglion cells against death from glutamate cytotoxicity and ocular hypertension: Implications for glaucoma." PROCEEDINGS OF THE NATIONAL ACADEMY OF SCIENCES OF THE UNITED STATES OF AMERICA 98:3398-3403. Elevation in RGC survival in the eyes of mice treated with achillolide A/TTF indicates that achillolide A/TTF administration is the cause for elevation in RGC survival levels.

More amyloid beta plaques and less neuronal cells are observed in brains of Tg-AD (Alzheimer's disease double transgenic (APP/PS 1) mice compared to brains of non-Tg littermates.

In order to show that in case of improvement in a neurodegenerative condition, such improvement is connected to protection of neuronal cells from amyloid beta toxicity by achillolide A/TTF, analysis in brain cryosections from Tg-AD mice and non-Tg littermates should be made in mice after treatment with achillolide A/TTF and in mice not treated with achillolide A/TTF, as compared with non-Tg littermates. Inject TTF/AcA to Tg-AD mice, sacrifice mice, prepare brain cryosections and following immunostaining and microscopic observation, calculate the number of neurons, as described in Butovsky O, Koronyo-Hamaoui M, Kunis G, Ophir E, Landa G, Cohen H, Schwartz M, (2006) Glatiramer acetate fights against Alzheimer's disease by inducing dendritic-like microglia expressing insulin-like growth factor 1. PROCEEDINGS OF THE NATIONAL ACADEMY OF SCIENCES OF THE UNITED STATES OF AMERICA 103:11784-11789. Elevation in the number of neurons in the brains of Tg-AD mice treated with achillolide A/TTF indicates that achillolide A/TTF administration is the cause for elevation in the number of neurons.

In order to show that in case of improvement in a neurodegenerative condition, such improvement is connected to reduction in glutamate levels by AcA, analysis in brains from vehicle or LPS-injected mice should be made in mice after treatment with AcA and in mice not treated with AcA. Intraperitoneal injection of LPS to mice is followed by a significant increase in neuroinflammation in mice brains as compared with vehicle controls. Implant glutamate sensor that measure glutamate levels into mice brains, inject LPS, treat with achillolide A, and monitor glutamate levels as described in *Molecules* 2014, 19(6), 7341-7355; Fabrication of Implantable, Enzyme-Immobilized Glutamate Sensors for the Monitoring of Glutamate Concentration Changes in Vitro and in Vivo Tina T.-C. Tseng, Cheng-Fu Chang and Wen-Chin Chan. Reduction in glutamate levels in brains of mice treated with AcA indicates that AcA administration is the cause for reduction in glutamate levels.

EXAMPLES

In order to illustrate the invention, the following examples are included. However, it is to be understood that these examples do not limit the invention and are only meant to suggest a method of practicing the invention.

Example 1

3,5,4'-trihydroxy-6,7,3'-trimethoxyflavone is not Cytotoxic to Microglial Cells

Microglial cells were activated with LPS in the presence or absence of different concentrations of 3,5,4'-trihydroxy-6,7,3'-trimethoxyflavone. Cell viability was determined (using MTT) 20 hr later. Results show that 3,5,4'-trihydroxy-6,7,3'-trimethoxyflavone is not cytotoxic to microglial cells.

Example 2

TTF Protects Astrocytes from $H_2O_2$-Induced Cell Death

TTF (8 µM) was added to astrocytes before (−2 h, −1 h) concomitant (0) or after (1 h, 2 h) the addition of $H_2O_2$ (175

μM). Cytotoxicity was measured 20 h later by the levels of LDH in the conditioned media. "W/o" means without. Results are means±SEM of two experiments (n=8) and are shown in FIG. 2A. P<0.01, *P<0.001, compared to cells that were treated with $H_2O_2$ only.

Astrocytes were treated with different concentrations of TTF, quercetin (as a control flavonoid) or memantine (as a control drug). $H_2O_2$ was added 2 h after the addition of compounds and cell death was determined 20 h later by the LDH method. The results are means±SEM of two experiments (n=7) and are shown in FIG. 2B. *P<0.05, ***P<0.001, compared to cells that were treated with $H_2O_2$ only.

Astrocytes were treated with different concentrations of TTF and cell death was determined 20 h later by the LDH method. The results are means±SEM of two experiments (n=10) and are shown in FIG. 2C. ***P<0.001, compared to untreated cells. Results show that TTF protects astrocytes from $H_2O_2$-induced cell death.

Example 3

TTF Suppresses $H_2O_2$-Induced SAPK/JNK, ERK 1/2 and MEK1 Phosphorylation in Astrocytes Astrocytes were treated with 175 μM of $H_2O_2$ for 40 min following preincubation with TTF for 2 h. The levels of phosphorylated and total SAPK/JNK (FIG. 3A), MEK1 (FIG. 3B) and ERK 1/2 (FIG. 3C) were measured by ELISA. The levels of each of the phosphorylated proteins were normalized to the levels of the total amount of the related proteins, and are presented as means±SEM of two experiments performed in duplicates (n=4). P<0.01, *P<0.001, compared to cells that were treated with $H_2O_2$ only. Results show that TTF suppresses $H_2O_2$-induced SAPK/JNK, ERK 1/2 and MEK1 phosphorylation in astrocytes.

Example 4

Effect of TTF on $H_2O_2$-Elevated Phosphorylation of CREB in Astrocytes

Astrocytes were treated with 175 μM of $H_2O_2$ for 30 min following preincubation with TTF for 2 h. The levels of phosphorylated and total CREB were measured by ELISA. The levels of pCREB were normalized to the levels of total CREB, and are presented as means±SEM of two experiments performed in duplicates (n=4). Results are shown in FIG. 4. **P<0.01, *P<0.05, compared to cells that were treated with $H_2O_2$ only. Results show that TTF inhibits $H_2O_2$-elevated phosphorylation of CREB in astrocytes.

Example 5

TIF Attenuates $H_2O_2$-Induced ROS Levels in Astrocytes

Astrocytes were pre-loaded with DCF-DA for 30 min and washed. FIG. 5A shows ROS levels (Fluorescence units, FU) of cells that had been treated with 175 μM $H_2O_2$ were measured at the indicated time points. Results of FIG. 5B obtained after TTF (8 μM) was added to astrocytes before (−2 h, −1 h), concomitant with (0) or after (1 h, 2 h) the addition of $H_2O_2$. ROS levels in astrocytes were measured 1 h and 4 h after the application of $H_2O_2$. The results represent the means±SEM of two experiments (n=8). Results of FIG. 5C obtained after astrocytes had been preincubated for 2 h with various concentrations of TTF, quercetin or memantine. $H_2O_2$ was added to the culture and the fluorescence intensity representing ROS levels was measured after 1 h. The results represent the means±SEM of three experiments (n=1). *P<0.05. P<0.01, *P<0.001, when compared to time zero (A) or when compared to cells that were treated with $H_2O_2$ only (B, C). Results show that TTF attenuates $H_2O_2$-induced ROS levels in astrocytes.

Example 6

Hydrogen Peroxide Scavenging

For assessment of $H_2O_2$ scavenging activity, 1 mM $H_2O_2$ and different concentrations of TTF, quercetin or memantine were co-incubated in PBS. Optical density was measured 10 min later. The results are shown in FIG. 6 and are means±SEM of two experiments performed in duplicates (n=4). P<0.01, *P<0.001, compared to $H_2O_2$ in the absence of TTF. Results show that TTF has hydrogen peroxide scavenging activity.

Example 7

DPPH Radical Scavenging Activity of TTF Compared to Memantine and to Quercetin

The DPPH scavenging ability of TTF, memantine and quercetin were compared for eight minutes. Results are shown in FIG. 7 and are the mean±SEM of two experiments performed in duplicates (n=4). Results show that DPPH radical scavenging activity of TTF compared to memantine and to quercetin.

Example 8

TTF Reduced Peroxyl Radical Levels Produced by 2,2'-Azobis(Amidinopropane) in Astrocytes Astrocytes were incubated with TTF or quercetin for 2 h. Then, the astrocytes were pre-loaded with DCF-DA for 30 min and washed. ABAP (0.6 mM) was added to the culture and the fluorescence intensity, representing ROS levels was measured. FIG. 8A shows fluorescence levels of cells that had been pre-incubated with 32 μM of TTF were measured at the indicated time points. FIG. 8B shows fluorescence levels of cells that had been pre-incubated with various concentrations of TTF or quercetin were measured 3 h after the addition of ABAP. FIG. 8C shows viability of the cells that was measured 20 h after the addition of ABAP by the crystal violet assay. The results are the mean±SEM of two experiments (n=8). *P<0.05, P<0.01, *P<0.001 compared to cells treated with ABAP only. Results show that TTF reduced peroxyl radical levels produced by 2,2'-Azobis (amidinopropane) in astrocytes.

Example 9

Figure 9A:
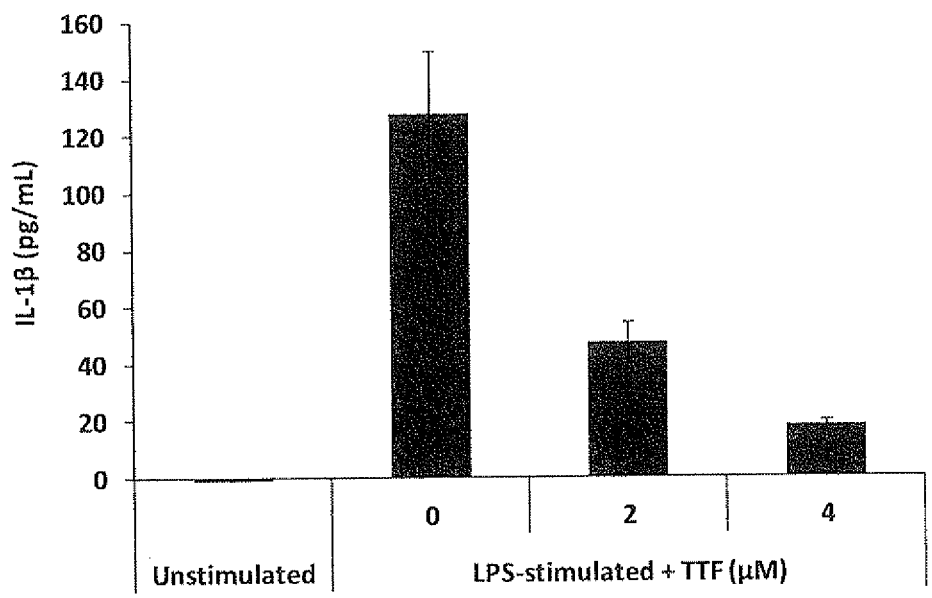
FIGS. 9A-C show that TTF attenuates the secretion of IL-1β and IL-6 in LPS-stimulated microglial cells.
Figure 9B:
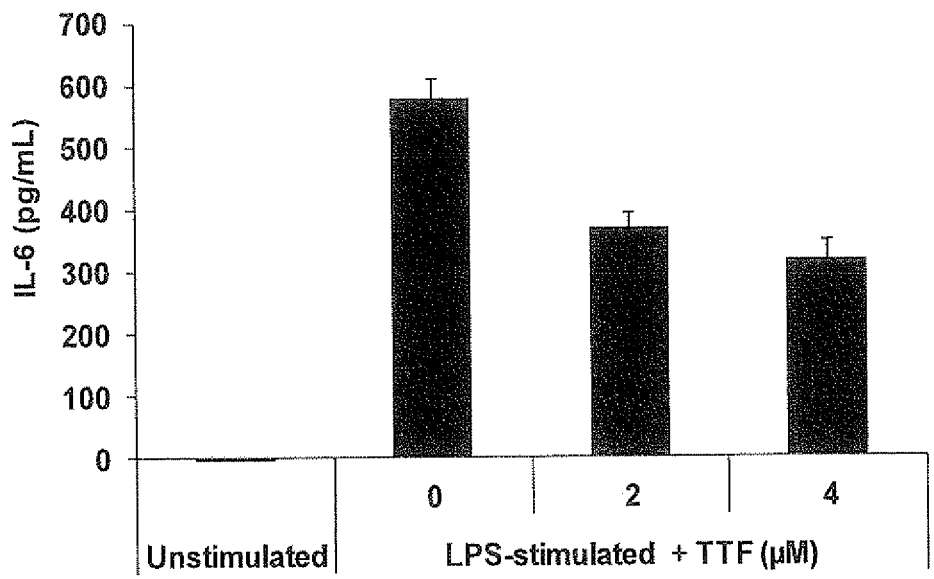
Figure 9C:
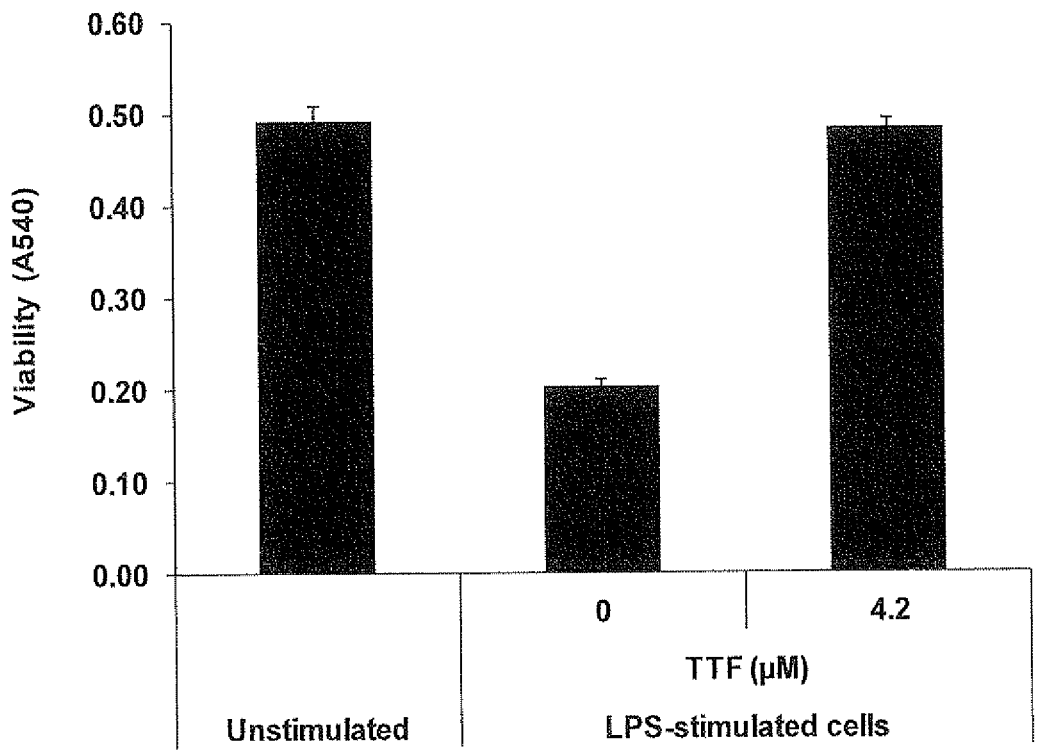

TTF Attenuates the Secretion of IL-1β and IL-6 in LPS-Stimulated Microglial Cells Microglial cells were treated with different concentrations of TTF, followed by stimulation with LPS (100 ng/mL). After 24 h, conditioned media were collected and tested for cytokine levels by ELISA. Results for IL-1β and IL-6 are shown in FIGS. 9A and 9B respectively. Cell viability was determined using the crystal violet assay (FIG. 9C). Values represent the means±SEM (n=4 for each treatment). Results show that TTF attenuates the secretion of IL-1β and IL-6 in LPS-stimulated microglial cells.

Example 10

TTF Prevents the Aβ$_{25-35}$-Induced Neuronal Cell Death

N2a neuronal cells were treated with Aβ$_{25-35}$ (25 μM) and TTF. Cytotoxicity (FIG. 10A) and viability (FIG. 10B) were obtained through LDH method and Crystal violet staining respectively and measured 20 hr later. The results are the mean±SEM of two different experiments (n=15). Results show that TTF prevents the Aβ$_{25-35}$-induced neuronal cell death.

Example 11

TTF Prevents the Aβ$_{25-35}$-Induced Reactive Oxygen Species (ROS) Elevation

N2a neuronal cells were treated with Aβ$_{25-35}$ (25 μM) and TTF. ROS levels were measured 20 hr later. The results are shown in FIG. 11 and are the mean±SEM of two different experiments (n=15). Results show that TTF prevents the Aβ$_{25-35}$-induced reactive oxygen species (ROS) elevation in N2a neuronal cells.

Example 12

TTF Down-Regulates the Aβ$_{25-35}$-Induced Phosphorylation of MEK1 in N2a Neuronal Cells without Affecting the Levels of Total MEK1

N2a cells were treated concomitantly with Aβ$_{25-35}$ and TTF for 30 min. Cells were extracted and the levels of phosphorylated or total MEK1 were determined by specific ELISA kits. The results are the mean±SEM of two different experiments for phosphoMEK1 (n=4) (see FIG. 12A) and of one experiment for total MEK1 (n=2) (see FIG. 12B). Results show that TTF down-regulates the Aβ$_{35}$s-induced phosphorylation of MEK1 in N2a neuronal cells without affecting the levels of total MEK1.

Example 13

TTF Down-Regulates the Aβ$_{25-35}$-Induced Phosphorylation of SAPK/JNK in N2a Neuronal Cells without Affecting the Levels of Total SAPK/JNK N2a cells were treated concomitantly with Aβ$_{25-35}$ and TIF for 40 min. Cells were extracted and the levels of phosphorylated or total SAPK/JNK were determined by specific ELISA kits. The results are the mean±SEM of two different experiments (n=4) for phosphorylated SAPK/JNK and three different experiments (n=6) for total SAPK/JNK. Results are shown in FIG. 13. Results show that TTF down-regulates the Aβ$_{25-35}$-induced phosphorylation of SAPK/JNK in N2a neuronal cells without affecting the levels of total SAPK/JNK.

Example 14

TTF Down-Regulates the Aβ$_{25-35}$-Induced Phosphorylation of ERK1/2 in N2a Neuronal Cells without Affecting the Levels of Total ERK1/2

N2a cells were treated concomitantly with Aβ$_{25-35}$ and TTF for 30 min. Cells were extracted and the levels of phosphorylated or total ERK1/2 were determined by specific ELISA kits. The results are shown in FIG. 14 and are the mean±SEM of two different experiments (n=4). Results show that TTF down-regulates the Aβ$_{25-35}$-induced phosphorylation of ERK1/2 in N2a neuronal cells without affecting the levels of total ERK1/2.

Example 15

TTF Down-Regulates the Aβ$_{25-35}$-Induced Phosphorylation of CREB in N2a Neuronal Cells without Affecting the Levels of Total CREB N2a cells were treated concomitantly with Aβ$_{25-35}$ and TTF for 30 min. Cells were extracted and the levels of phosphorylated (FIG. 15 A) or total (FIG. 15 B) CREB were determined by specific ELISA kits. The results are the mean±SEM of one experiment (n=2). Results show that TTF down-regulates the Aβ$_{25-35}$-induced phosphorylation of CREB in N2a neuronal cells without affecting the levels of total CREB.

Example 16

TTF Prevents the Glutamate-Induced Neuronal Cell Death

N2a neuronal cells were treated with glutamate (100 μM) and TTF. Cytotoxicity was measured 20 hr later. The results are shown in FIG. 16 and are the mean±SEM of one experiment (n=8). Results show that TTF prevents the glutamate-induced neuronal cell death.

Example 17

TTF Prevents the Glutamate-Induced Reactive Oxygen Species (ROS) Elevation

N2a neuronal cells were treated with glutamate (100 μM) and TTF. ROS levels were measured 20 hr later. The results are shown in FIG. 17 and are the mean±SEM of two different experiments (n=16). Results show that TTF prevents the glutamate-induced reactive oxygen species (ROS) elevation.

Example 18

TTF Prevents the SNP-Induced Reactive Oxygen Species (ROS) Elevation

N2a neuronal cells were pre-loaded with DCF-DA for 30 min and washed. TTF (2 μM) was added to cells before (−2 h, −1 h), concomitant with (0) or after (1 h, 2 h) the addition of SNP (250 μM). ROS levels in neuronal cells were measured 20 h after the application of SNP. The results are shown in FIG. 18 and are the mean±SEM of two different experiments (n=15). Results show that TTF prevents the SNP-induced reactive oxygen species (ROS) elevation in N2a cells.

Example 19

TTF Down-Regulates the SNP-Induced Phosphorylation of ERK1/2 in N2a Neuronal Cells without Affecting the Levels of Total ERK1/2

N2a cells were treated concomitantly with SNP and TTF for 40 min. Cells were extracted and the levels of phosphorylated or total ERK1/2 were determined by specific ELISA kits. The results are shown in FIG. 19 and are the mean±SEM of one experiment (n=2). Results show that TTF down-regulates the SNP-induced phosphorylation of ERK1/2 in N2a neuronal cells without affecting the levels of total ERK 1/2.

Example 20

TTF Down-Regulates the SNP-Induced Phosphorylation of MEK1 in N2a Neuronal Cells without Affecting the Levels of Total MEK1

N2a cells were treated concomitantly with SNP and TTF for 40 min. Cells were extracted and the levels of phosphorylated or total MEK1 were determined by specific ELISA kits. The results are shown in FIG. 20 are the mean±SEM of two different experiments (n=−4). Results show that TTF down-regulates the SNP-induced phosphorylation of MEK1 in N2a neuronal cells without affecting the levels of total MEK1.

Example 21

Down-Regulation of Glutamate Secretion from Activated Microglial Cells by Achillolide A Microglial cells were treated with the indicated concentrations of achillolide A, followed by stimulation with LPS (100 ng/mL). After 20 h, conditioned media were collected and tested for glutamate levels by a commercial kit. Values represent the means±SEM (n=4 for each treatment).  $p<0.01$; * $p<0.001$, compared to LPS-stimulated cells. Results show that achillolide A down-regulates glutamate secretion from activated microglial cells.

Example 22

Inhibition of NO Production and Reduction in Cytotoxicity by Activated Microglial Cells in Response to Different Concentrations of Achillolide A In FIG. 21 A, microglial cells were treated with different concentrations of achillolide A, dexamethasone or memantine (as reference drugs) and were concomitantly activated by LPS (4.5 ng/mL) for 20 h. Cell conditioned supernatants were collected, and the levels of NO were measured using Griess reaction. Cytotoxicity was measured using the LDH method (FIG. 21B). Values represent the mean±SEM (n=12 for each treatment).  $p<0.01$; * $p<0.001$ relative to cells that were treated to LPS only. Results show increasing inhibition of NO production by activated microglial cells in response to increasing concentrations of achillolide A.

Example 23

Figure 23:
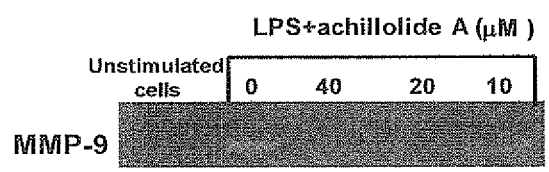
FIG. 23 shows down-regulation of MMP-9 activity and transcripts in activated microglial cells by achillolide A.
Figure 23:
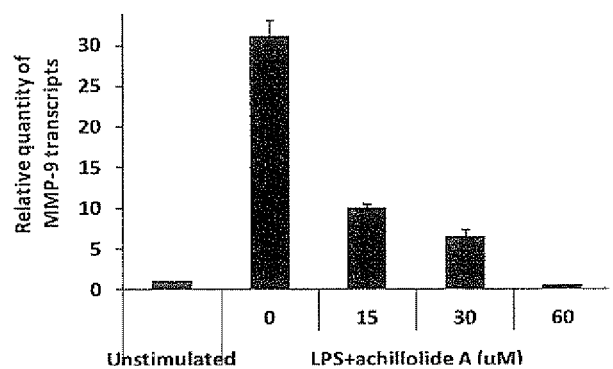
Figure 23:
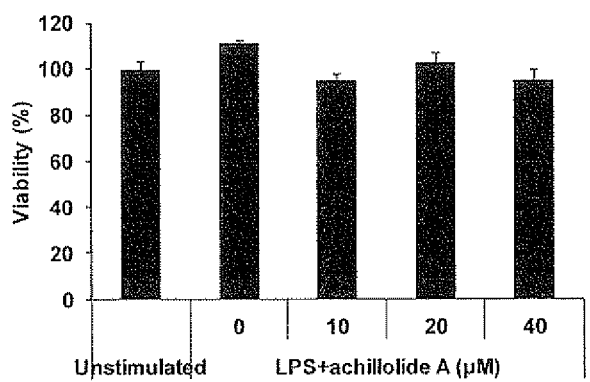

Down-Regulation of MMP-9 Activity and Transcripts in Activated Microglial Cells by Achillolide A Microglial cells were treated with the indicated concentrations of achillolide A, followed by stimulation with LPS (4.5 ng/mL). Conditioned media were collected 24 h later and tested for MMP-9 activity by gel zymography as shown in FIG. 23 A. The zymogram represents two independent experiments. The levels of MMP-9 transcripts were measured by quantitative real-time PCR. The results from three technical replicates were normalized to β-actin and are expressed as relative quantity of MMP-9 transcripts in FIG. 23 B. The results are means±SD of one representative experiment out of three experiments. Cell viability was determined 24 h later by the crystal violet assay. Values represent the means±SEM (n=4 for each treatment). Results are shown in FIG. 23C. The results show that AcA down-regulates MMP-9 activity and transcripts in activated microglial cells by.

Example 24

Achillolide A Attenuates the Transcription of COX-2, iNOS, IL-1β and TNFα in and Secretion of IL-1β from LPS-Stimulated Microglial Cells Microglial cells were treated with 20 µg/mL of achillolide A, followed by stimulation with LPS (4.5 ng/mL). After 5 h the levels of the indicated transcripts were measured by quantitative real-time PCR and the relative quantity (RQ) of the different transcripts were determined. Real time PCR was performed according to the protocol for "assay-on demand" primers (Applied Biosystems). The results from three technical replicates were normalized to Tubulin. The results are expressed as percentages relative to LPS-stimulated cells. The results are the means±SD of one experiment out of three identical experiments and are shown in FIGS. 24A-D. Microglial cells were treated with the indicated concentrations of achillolide A, followed by stimulation with LPS (100 ng/mL). After 24 h, conditioned media were collected and tested for cytokine levels by ELISA. IL-1β levels in the activated cells (designated as 100%) were 128 pg/mL. Values represent the means±SEM (n=4 for each treatment). * $p<0.05$;  $p<0.0/$; * $p<0.001$, compared to LPS-activated microglial cells. Results are shown in FIG. 24E. Results show that achillolide A attenuates the secretion of IL-1β from LPS-stimulated microglial cells.

Example 25

Achillolide A Inhibits the Peroxyl Radical-Induced Oxidation of DCFH in Microglial Cells Cells were incubated for 1 h with different concentrations of achillolide A. Then, the cells were pre-loaded with DCF-DA for 30 min and washed. ABAP (0.6 mM) was added to the culture and ROS levels were measured at the indicated time points. Microglial cells were treated with different concentrations of achillolide A or dexamethasone. Values represent the mean±SEM (n=8 for each treatment).  $p<0.0$; * $p<0.001$, compared to ROS levels at 20 h without compound. Results are shown in FIG. 25. Results show that achillolide A inhibits the peroxyl radical-induced oxidation of DCFH in microglial cells.

Example 26

DPPH Radical Scavenging Activity of Achillolide A

The DPPH scavenging ability of achillolide A and quercetin were tested for eight minutes. Values represent the mean±SEM (n=4 for each concentration). p<0.01; *p<0.001, compared to a mixture without achillolide A or quercetin. Results are shown in FIG. 26. Results show that AcA has DPPH scavenging ability.

Example 27

Achillolide A (AcA) Prevents the $A\beta_{25-35}$-Induced Neuronal Cell Death and Reactive Oxygen Species (ROS) Elevation N2a neuronal cells were treated with $A\beta_{25-35}$ (25 μM) and achillolide A. Cytotoxicity (FIG. 27A) viability (FIG. 27B) and ROS levels (FIG. 27C) were measured 20 hr later. The results are the mean±SEM of two different experiments (n=16). Results show that Achillolide A (AcA) prevents the $A\beta_{25-35}$-induced neuronal cell death and reactive oxygen species (ROS) elevation.

Example 28

Figure 28:
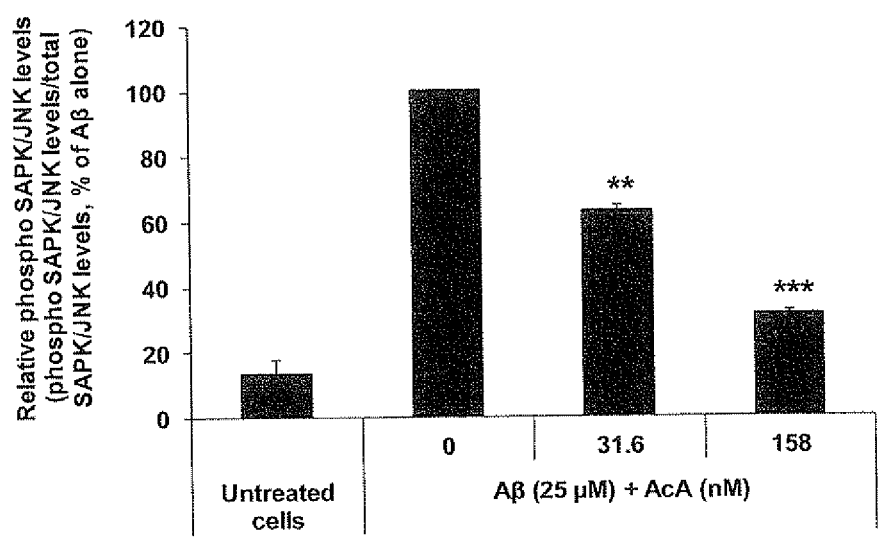
FIG. 28 shows that achillolide A (AcA) down-regulates the $A\beta_{25-35}$-induced phosphorylation of SAPK/JNK in N2a neuronal cells without affecting the levels of total SAPK/JNK.

Achillolide A (AcA) Down-Regulates the $A\beta_{25-35}$-Induced Phosphorylation of SAPK/JNK in N2a Neuronal Cells without Affecting the Levels of Total SAPK/JNK N2a cells were treated concomitantly with $A\beta_{25-35}$ and achillolide A for 40 min. Cells were extracted and the levels of phosphorylated or total SAPK/JNK were determined by specific ELISA kits. The results are the mean±SEM of two different experiments (n=4) for phosphorylated SAPK/JNK and three different experiments (n=6) for total SAPK/JNK. Results are shown in FIG. 28 Results show that Achillolide A (AcA) down-regulates the $A\beta_{25-35}$-induced phosphorylation of SAPK/JNK in N2a neuronal cells without affecting the levels of total SAPK/JNK.

Example 29

Achillolide A (AcA) Down-Regulates the $A\beta_{25-35}$-Induced Phosphorylation of ERK 1/2 in N2a Neuronal Cells without Affecting the Levels of Total ERK 1/2

Figure 29:
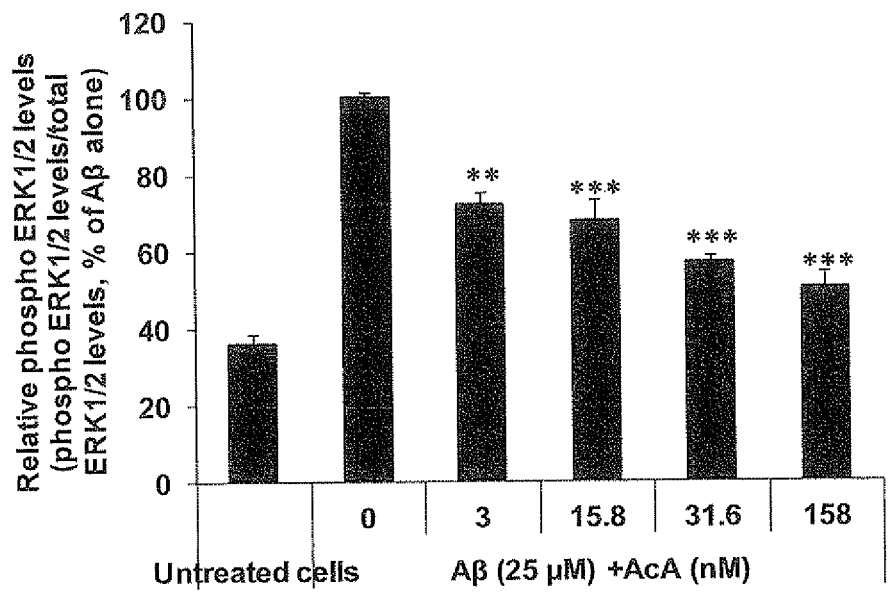
FIG. 29 shows that achillolide A (AcA) down-regulates the $A\beta_{25-35}$-induced phosphorylation of ERK 1/2 in N2a neuronal cells without affecting the levels of total ERK 1/2.

N2a cells were treated concomitantly with $A\beta_{25-35}$ and achillolide A for 40 min. Cells were extracted and the levels of phosphorylated or total ERK 1/2 were determined by specific ELISA kits. The results are the mean±SEM of two different experiments (n=4). Results are shown in FIG. 29. Results show that achillolide A (AcA) down-regulates the $A\beta_{25-35}$-induced phosphorylation of ERK 1/2 in N2a neuronal cells without affecting the levels of total ERK 1/2.

Example 30

Figure 30:
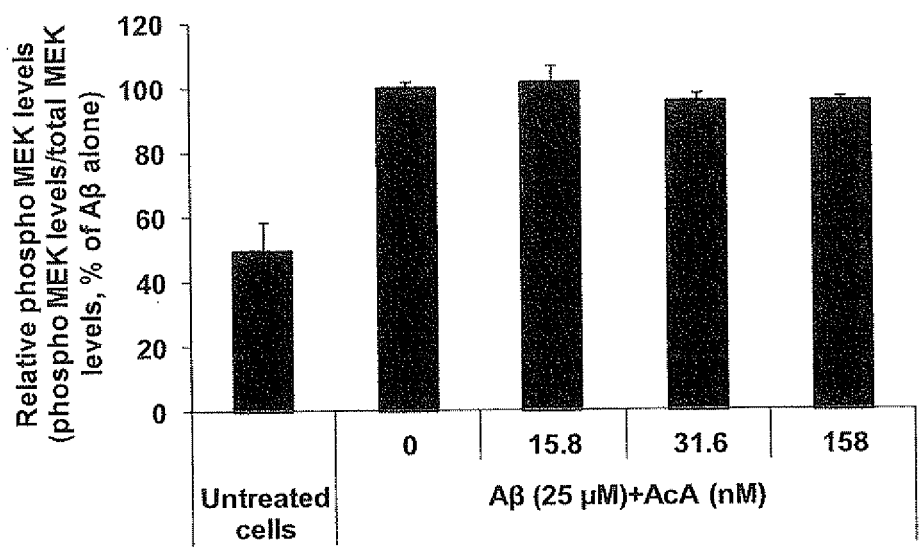
FIG. 30 shows the effect of AcA on the $A\beta_{25-35}$-induced phosphorylation of MEK1 in N2a neuronal cells.

Effect of AcA on the $A\beta_{25-35}$-Induced Phosphorylation of MEK1 in N2a Neuronal Cells N2a cells were treated concomitantly with $A\beta_{25-35}$ and AcA for 40 min. Cells were extracted and the levels of phosphorylated or total MEK1 were determined by specific ELISA kits. The results are the mean±SEM of one experiment (n=2). Results are shown in FIG. 30. Results show that AcA does not affect the $A\beta_{25-35}$-induced phosphorylation of MEK1 in N2a neuronal cells.

Example 31

Achillolide A Protects N2a Neuronal Cells from Glutamate-Induced Cell Death

Achillolide A was added to N2a cells before (−2 h, −1 h) concomitant (0) or after (1 h, 2 h) the addition of glutamate. Cytotoxicity was measured 20 h later by the levels of LDH in the conditioned media. Results are means±SEM of two experiments (n=16). P<0.01, *P<0.001, compared to cells that were treated with glutamate only. Results are shown in FIG. 31. Results show that achillolide A protects N2a neuronal cells from glutamate-induced cell death.

Example 32

Achillolide A Prevents the Glutamate-Induced Neuronal Cell Death

N2a neuronal cells were treated with $A\beta_{25-35}$ (25 μM) and achillolide A. Cytotoxicity was measured 20 hr later. The results are the means±SEM of two different experiments (n=16). Results are shown in FIG. 32. Results show that achillolide A (AcA) prevents the glutamate-induced neuronal cell death.

Example 33

Achillolide A Prevents the Glutamate-Induced Neuronal Cell Death

N2a neuronal cells were treated with $A\beta_{25-35}$ (25 μM) and achillolide A or memantine. Cytotoxicity was measured 20 hr later. The results are the mean±SEM of two different experiments (n=16) for AcA and one experiment (n=8) for memantine. Results are shown in FIG. 33. Results show that AcA prevents the glutamate-induced neuronal cell death.

Example 34

Achillolide A Prevents the Glutamate-Induced Reactive Oxygen Species (ROS) Elevation in N2a Cells N2a neuronal cells were treated with glutamate (100 μM) and achillolide A. ROS levels were measured 20 hr later. The results are the mean±SEM of three different experiments (n=24). Results are shown in FIG. 34. Results show that Achillolide A prevents the glutamate-induced reactive oxygen species (ROS) elevation in N2a cells.

Example 35

Achillolide A Protects N2a Neuronal Cells from Glutamate-Induced ROS

Achillolide A was added to N2a cells before (−2 h, −1 h) concomitant (0) or after (1 h, 2 h) the addition of glutamate. ROS levels were measured 20 h later. Results are means±SEM of two experiments (n=16). P<0.01, *P<0.001, compared to cells that were treated with glutamate only. Results are shown in FIG. 35. Results show that achillolide A protects N2a neuronal cells from glutamate-induced ROS.

Example 36

Figure 36:
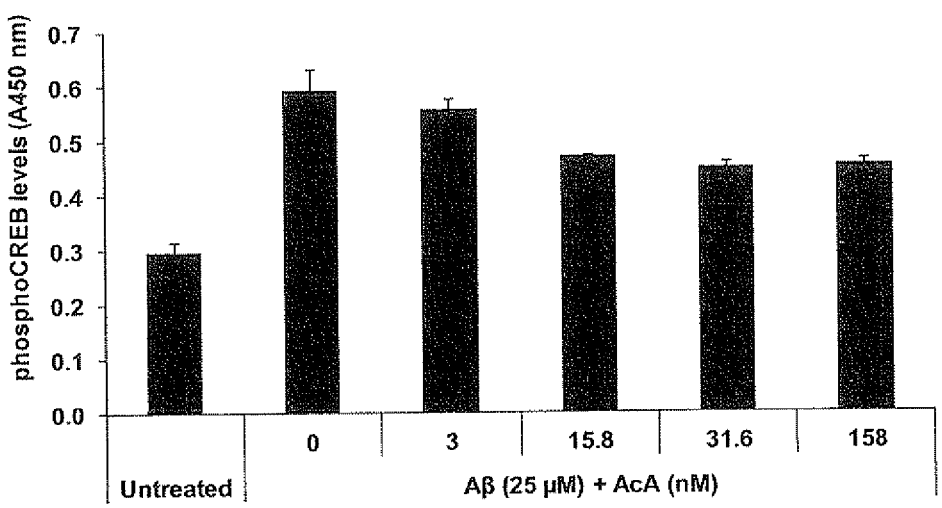
FIG. 36 shows that AcA down-regulates the $A\beta_{25-35}$-induced phosphorylation of CREB in N2a neuronal cells.

AcA Down-Regulates the $A\beta_{25-35}$-Induced Phosphorylation of CREB in N2a Neuronal Cells N2a cells were treated concomitantly with $A\beta_{25-35}$ and AcA for 30 min. Cells were extracted and the levels of phosphorylated CREB were determined by A specific ELISA kit. The results are the mean±SEM of one experiment (n=2). Results are shown in FIG. 36. Results show that AcA down-regulates the $A\beta_{25-35}$-induced phosphorylation of CREB in N2a neuronal cells.

Example 37

Achillolide A Protects Astrocytes from $H_2O_2$-Induced Cell Death

Figure 37A:
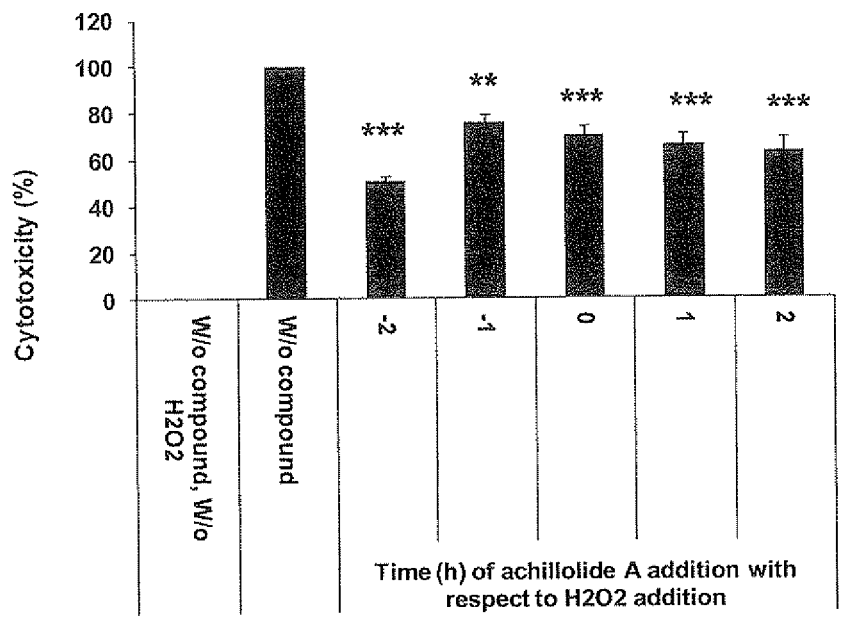
FIG. 37A-B show that achillolide A protects astrocytes from $H_2O_2$-induced cell death.

Achillolide A (80 µM) was added to astrocytes before (−2 h, −1 h) concomitant (0) or after (1 h, 2 h) the addition of $H_2O_2$. Cytotoxicity was measured 20 h later by the levels of LDH in the conditioned media. "W/o" means without. Results are means±SEM of two experiments (n=8). P<0.01, *P<0.001, compared to cells that were treated with $H_2O_2$ only. Results are shown in FIG. 37A.

Figure 37B:
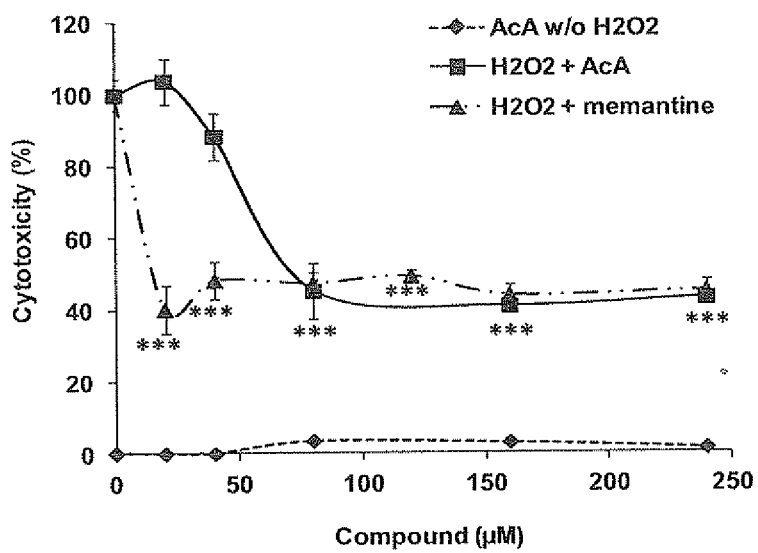

Astrocytes were treated with different concentrations of achillolide A or memantine (as a control drug) or vehicle. $H_2O_2$ (200 µM) was added 2 h after the addition of compounds and cell death was determined 20 h later by the LDH method. The results are means±SEM of two experiments (n=8). ***P<0.001, compared to cells that were treated with $H_2O_2$ only. Results are shown in FIG. 37B. Results show that achillolide A protects astrocytes from $H_2O_2$-induced cell death.

Example 38

Hydrogen Peroxide Scavenging

Figure 38:
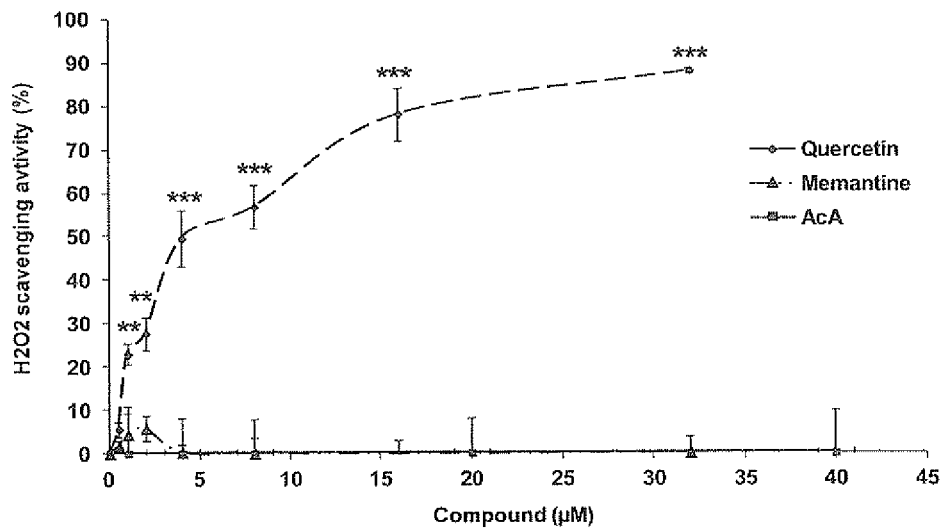
FIG. 38 shows the hydrogen peroxide scavenging ability of AcA.

For invention of $H_2O_2$ scavenging activity, 1 mM $H_2O_2$ and different concentrations of achillolide A, quercetin or memantine were co-incubated in PBS. Optical density was measured 10 min later. The results are means±SEM of two experiments performed in duplicates (n=4). P<0.01, *P<0.001, compared to $H_2O_2$ in the absence of compound Results are shown in FIG. 38. Results show the hydrogen peroxide scavenging ability of AcA.

Example 39

Achillolide A Attenuates $H_2O_2$-Induced ROS Production in Astrocytes

Figure 39A:
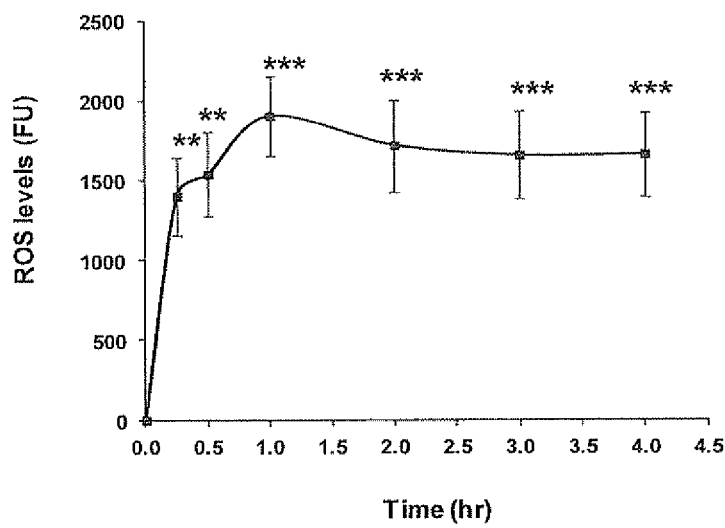
FIG. 39A-B show that achillolide A attenuates $H_2O_2$-induced ROS production in astrocytes.

Astrocytes were preloaded with DCF-DA for 30 min and washed. $H_2O_2$(175 µM) was added and the fluorescence intensity representing ROS levels was measured at the indicated time points. P<0.01, *P<0.001, compared to ROS levels in astrocytes in the absence of $H_2O_2$. Results are shown in FIG. 39A.

Figure 39B:
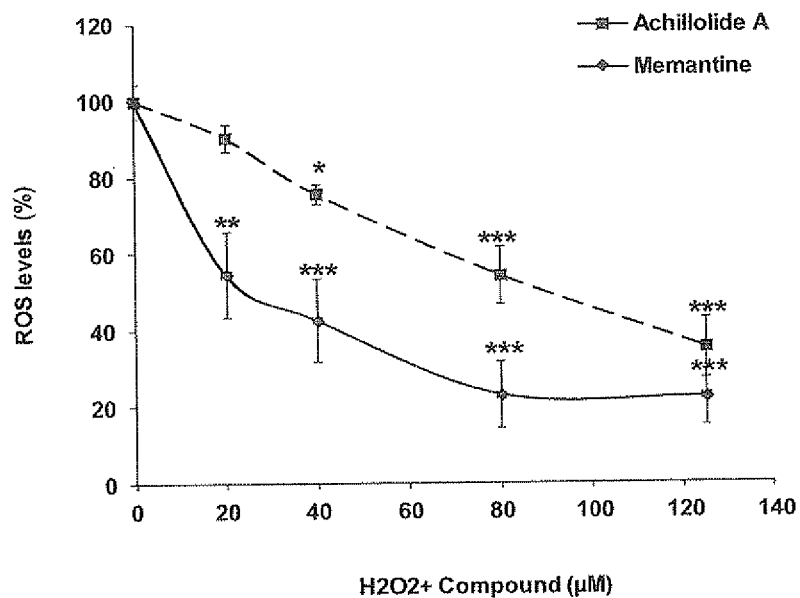

Preloaded astrocytes were then preincubated for 2 h with various concentrations of achillolide A or memantine. $H_2O_2$ (175 µM) was added and the fluorescence intensity was measured 20 h later. The results represent means±SEM of two different experiments (n=8). ***P<0.001. Results are shown in FIG. 39B. Results show that achillolide A attenuates $H_2O_2$-induced ROS production in astrocytes.

Example 40

Figure 40A:
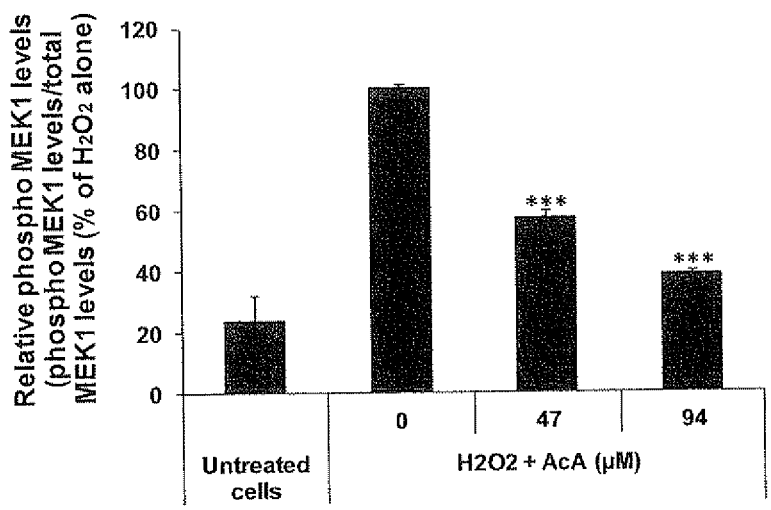
FIG. 40A-D show that achillolide A down-regulates the $H_2O_2$-induced phosphorylation of MEK1, ERK1/2, SAPK/JNK and p38 in astrocytes without affecting the levels of the total related protein.
Figure 40B:
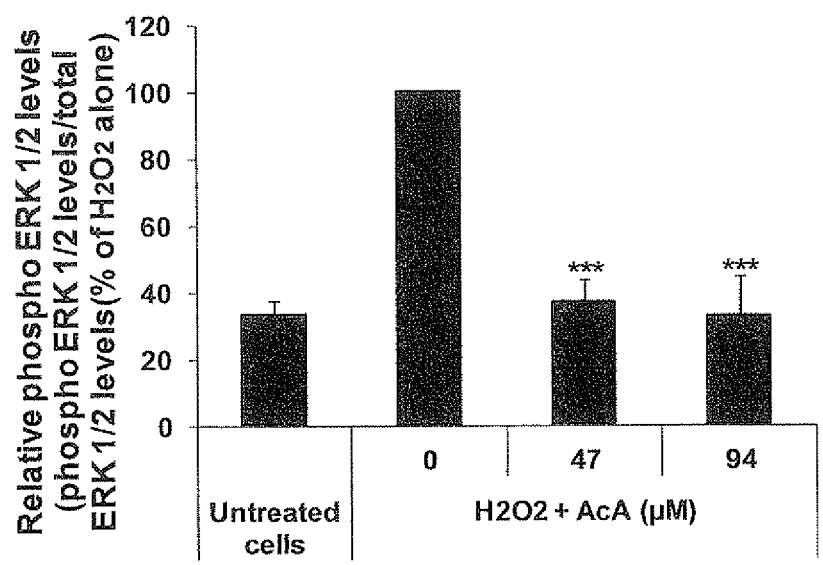
Figure 40C:
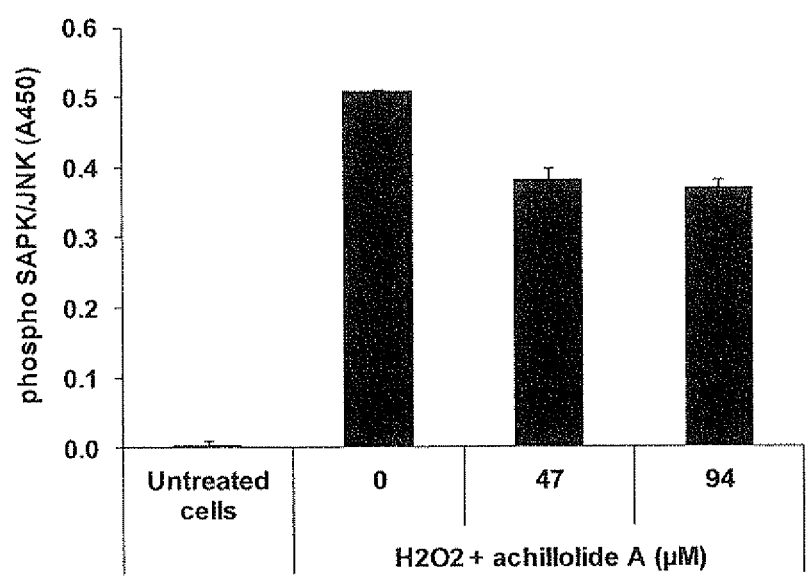
Figure 40D:
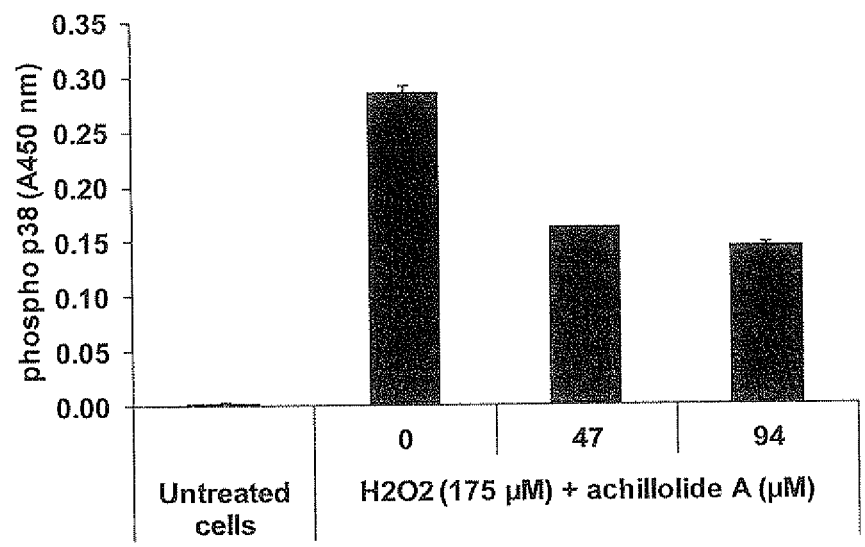

Inhibitory Effect of Achillolide A on $H_2O_2$-Induced Phosphorylation of ERK1/2, MEK1, SAPK/JNK and p38 in Astrocytes Astrocytes were treated with 175 µM of $H_2O_2$ for 40 min following preincubation with achillolide A for 2 h. The levels of phosphorylated and total MEK1 (FIG. 40A), phosphorylated and total ERK1/2 (FIG. 40B), phosphorylated SAPK/JNK (FIG. 40C) and phosphorylated p38 (FIG. 40D) were measured by ELISA. The results are means±SEM of two experiments (n=4) for MEK1 and ERK 1/2, one experiment for SAPK/JNK and p38 (n=2). ***p<0.001. Results show that achillolide A has inhibitory effect on $H_2O_2$-induced phosphorylation of ERK1/2, MEK1, SAPK/JNK and p38 in astrocytes.

Example 41

Figure 41:
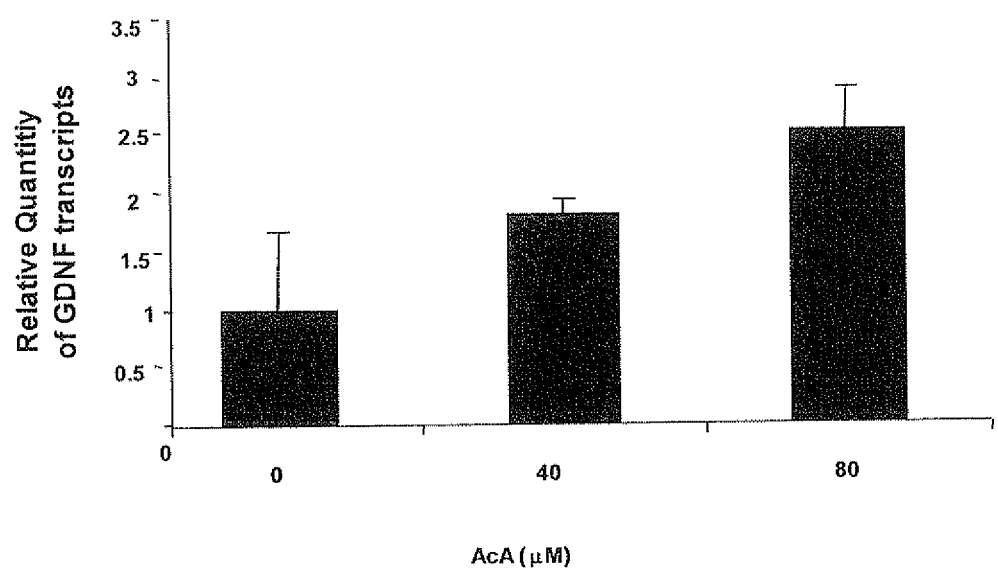
FIG. 41 shows that treatment with achillolide A increases the levels of GDNF transcript in primary astrocytes.
Figure 42A:
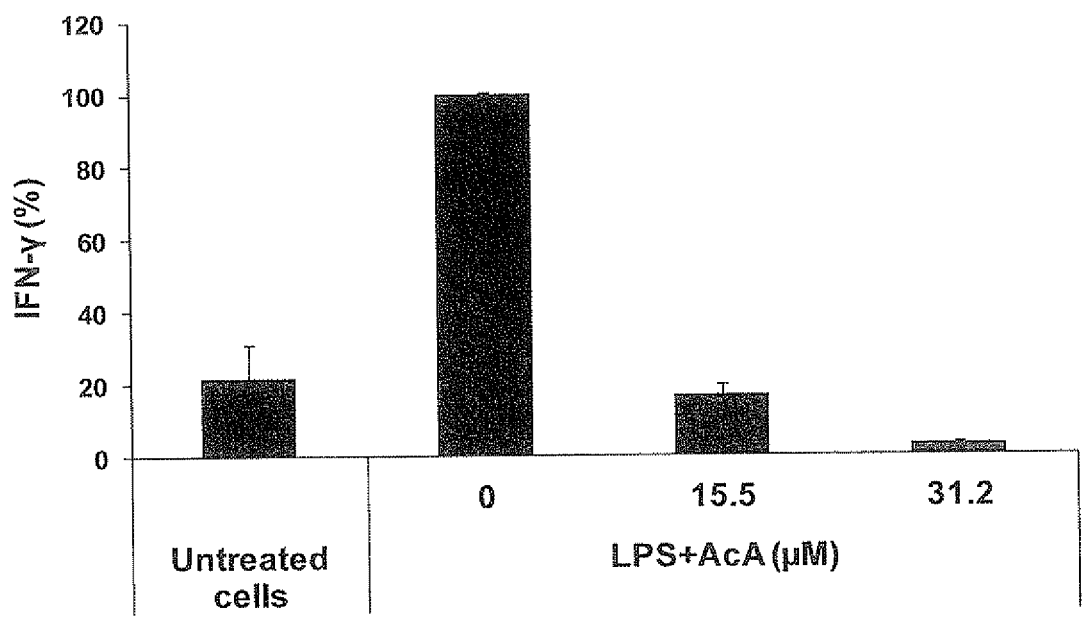
FIGS. 42A-F show that achillolide A downregulates cytokine secretion from LPS-activated splenocytes of naive mice.
Figure 42B:
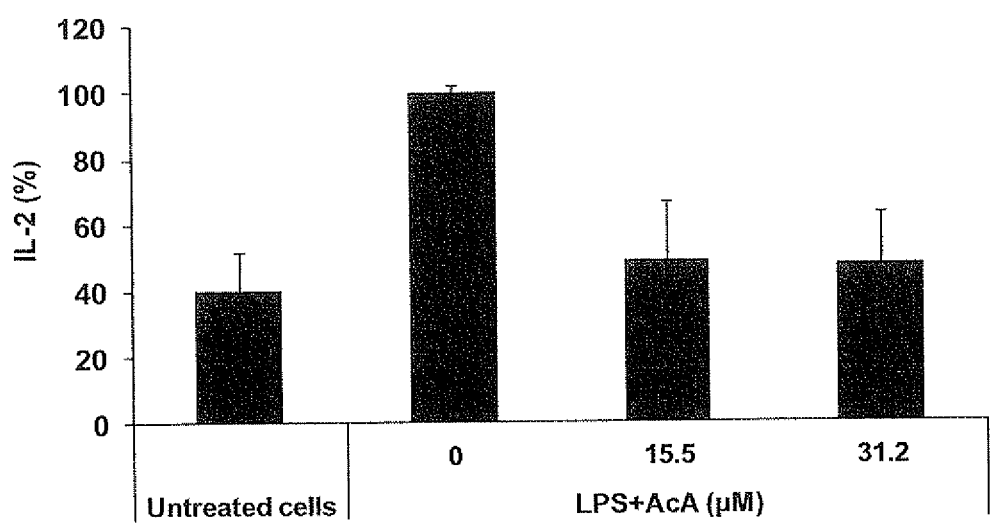
Figure 42C:
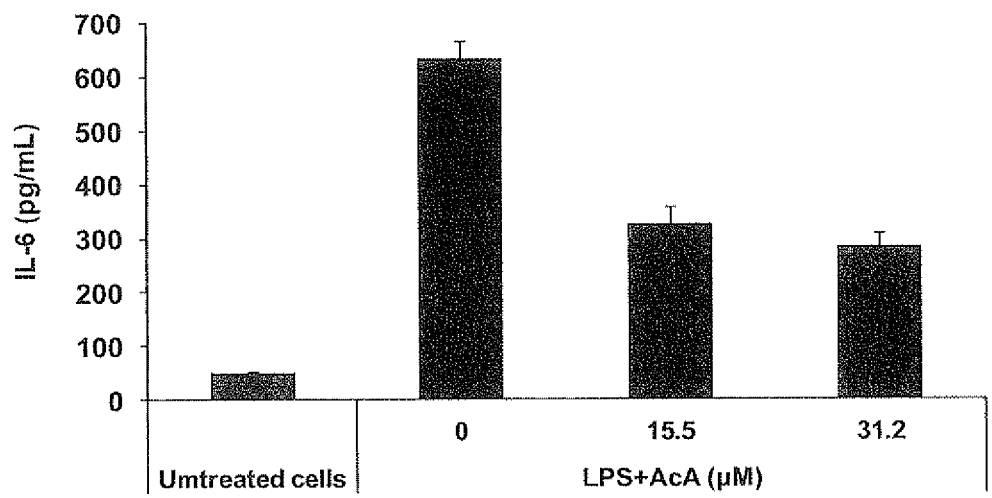
Figure 42D:
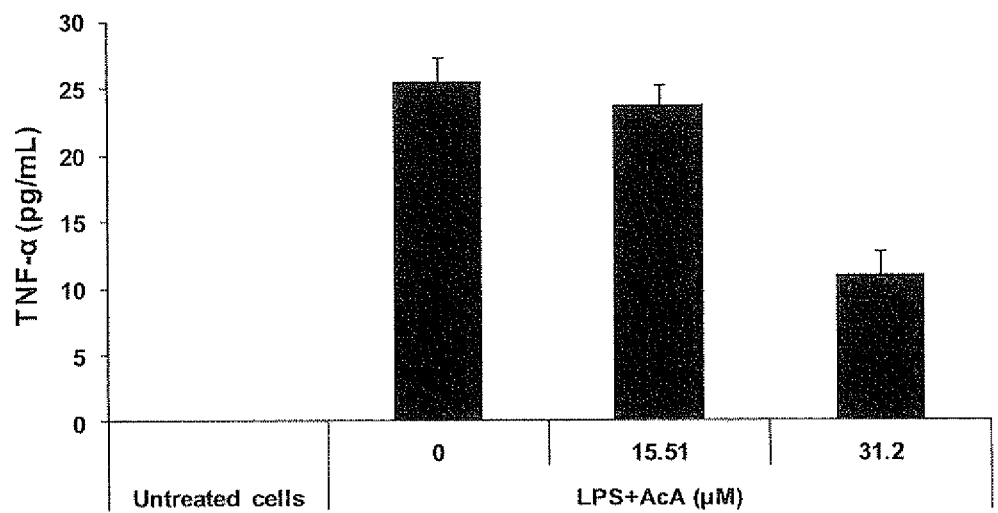
Figure 42E:
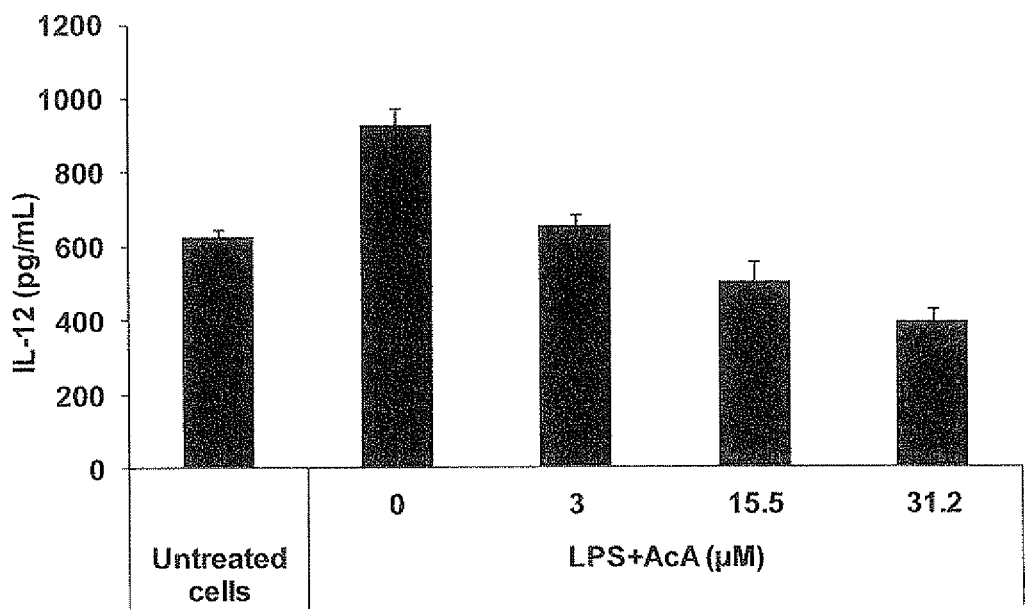
Figure 42F:
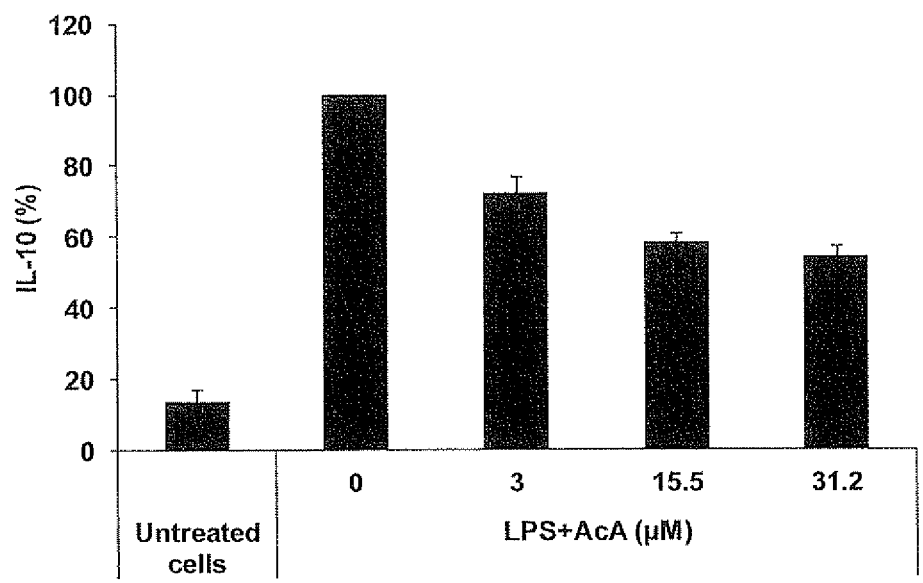

Treatment with Achillolide A Increases the Levels of GDNF Transcript in Primary Astrocytes Astrocytes were treated with achillolide A for 24 h. Total RNA was then extracted. GDNF transcripts were measured using quantitative real time PCR. The results of three technical replicates were normalized to glyceraldehyde-3-phosphate (GAPDH) and are expressed as relative quantities of GDNF transcripts. Real time PCR was performed according to the protocol for "assay-on demand" primers (Applied Biosystems). The results are means±SD of one out of three (for 24 h) or two (for 6 h) identical biological experiments. Results are shown in FIG. 41. Results show that treatment with achillolide A increases the levels of GDNF transcript in primary astrocytes.

Example 42

Achillolide A Downregulates Cytokine Secretion from LPS-Activated Splenocytes of Naive Mice Ten naive Balb/c mice were sacrificed by decapitation. Spleens were removed Spleens were removed from mice, pooled and squeezed to single cell suspension. Red blood cells were lysed using lysis buffer, cells were washed several times, and were plated ($5\times10^6$ cells/well/ml) on a 24-well tissue culture plate. Cells were then stimulated with LPS (5 µg/mL) in the presence or absence of achillolide A. Conditioned media of the cells were collected for analysis: IL-2, after 24 h; IFNγ, TNF-α, IL-10, IL-12 and IL-6 after 48 hr. Cytokine levels were measured by ELISA in supernatants collected at the indicated time points. Data represent the mean±SEM from two different experiments performed in duplicates. 100% for each cytokine: IL-2-210 pg/mL, IFNγ-1505 pg/mL, IL-10-297 pg/mL.

Example 43

Figure 43:
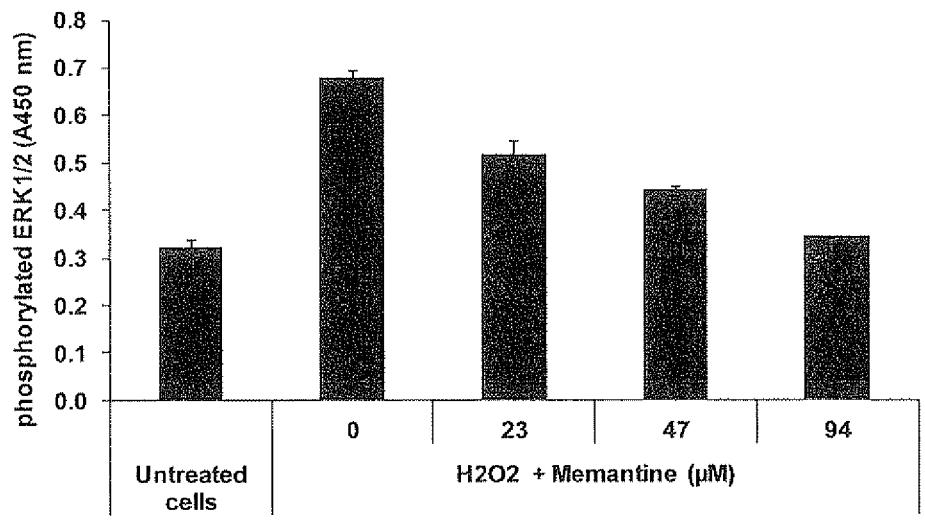
FIG. 43 shows the inhibitory effect of memantine on $H_2O_2$-induced phosphorylation of ERK1/2 in astrocytes.

Inhibitory Effect of Memantine on $H_2O_2$-Induced Phosphorylation of ERK1/2 in Astrocytes Astrocytes were treated with 175 µM of $H_2O_2$ for 40 min following preincubation with memantine for 2 h. The levels of phosphorylated p44/42 MAPK were measured by ELISA. The results are means±SEM of one experiments (n=2). Results are shown in FIG. 43. Results show that memantine has inhibitory effect on $H_2O_2$-induced phosphorylation of ERK1/2 in astrocytes.

Example 44

Figure 44:
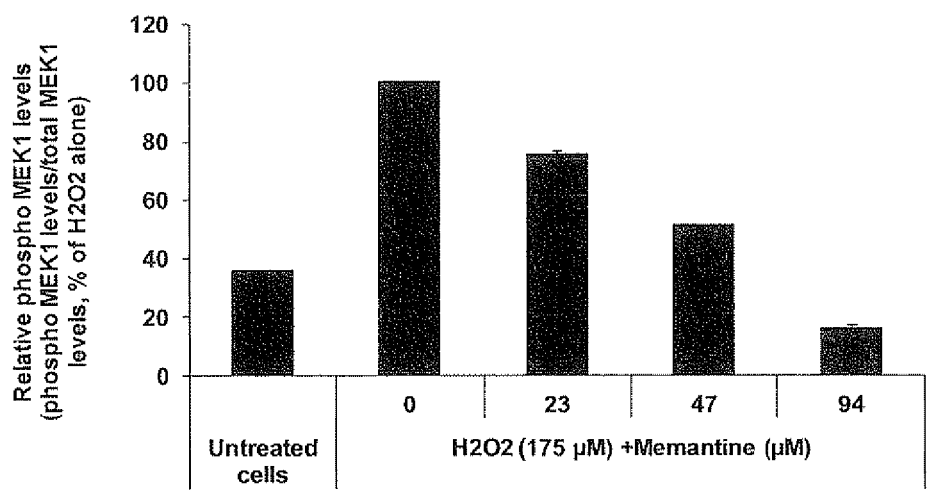
FIG. 44 shows the inhibitory effect of memantine on $H_2O_2$-induced phosphorylation of MEK1 in astrocytes.

Inhibitory Effect of Memantine on $H_2O_2$-Induced Phosphorylation of MEK1 in Astrocytes Astrocytes were treated with 175 μM of $H_2O_2$ for 40 min following preincubation with memantine for 2 h. The levels of phosphorylated and total MEK1 were measured by ELISA. The results are means±SEM of one experiment (n=2). Results are shown in FIG. 44. Results show that memantine has inhibitory effect on $H_2O_2$-induced phosphorylation of MEK1 in astrocytes.

Example 45

Figure 45:
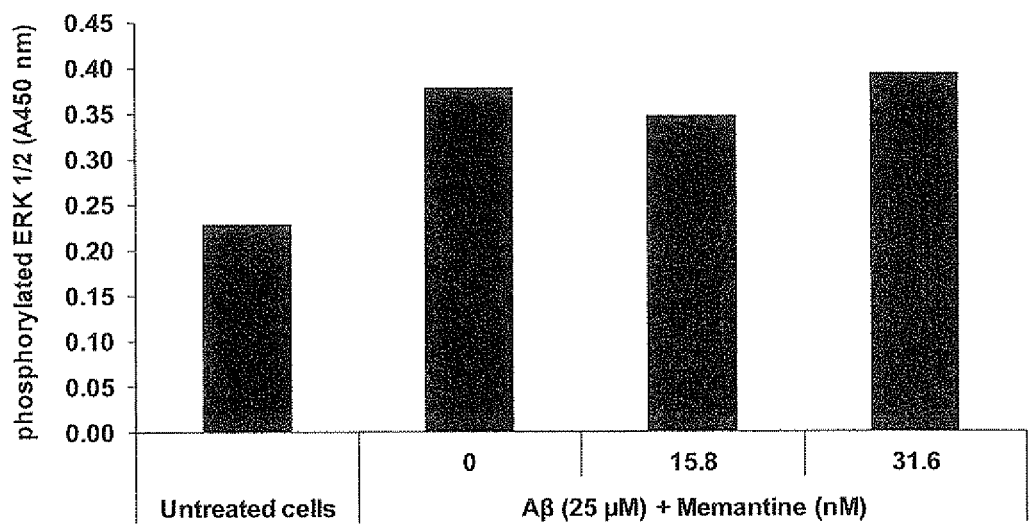
FIG. 45 shows that memantine does not affect the $A\beta_{25\text{-}35}$-induced phosphorylation of ERK1/2 in N2a neuronal cells.

Memantine does not Affect the $A\beta_{25-35}$-Induced Phosphorylation of ERK1/2 in N2a Neuronal Cells N2a cells were treated concomitantly with $A\beta_{25-35}$ and memantine for 30 min. Cells were extracted and the levels of phosphorylated ERK1/2 were determined by a specific ELISA kit. The results are the mean±SEM of one experiment (n=2). Results are shown in FIG. 45. Results show that Memantine does not affect the $A\beta_{25-35}$-induced phosphorylation of ERK1/2 in N2a neuronal cells.

Example 46

Figure 46:
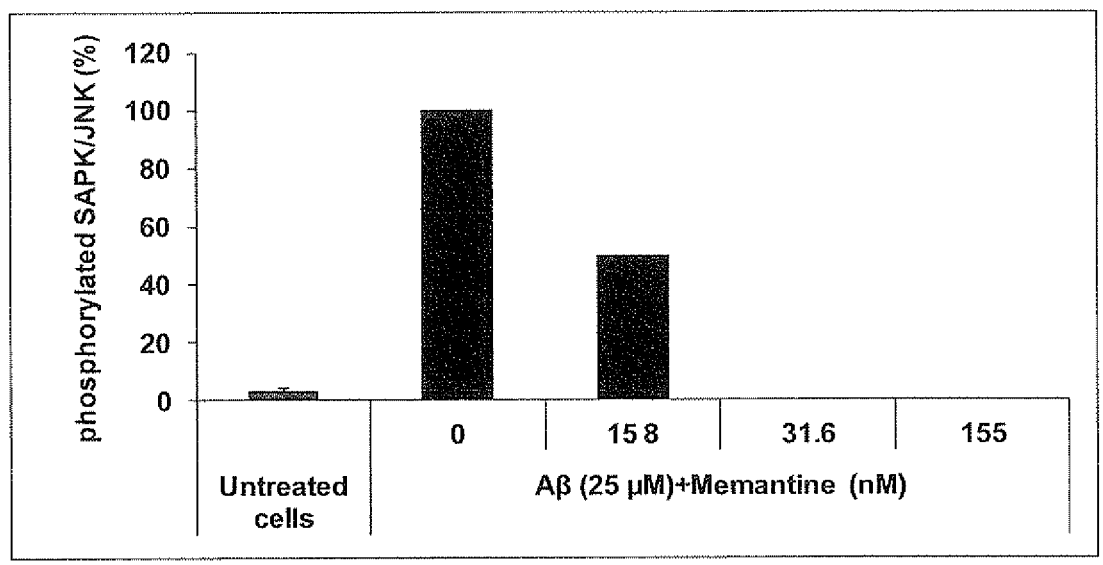
FIG. 46 shows that memantine down-regulates the $A\beta_{25\text{-}35}$-induced phosphorylation of SAPK/JNK in N2a neuronal cells.

Memantine Down-Regulates the $A\beta_{25-35}$-Induced Phosphorylation of SAPK/JNK in N2a Neuronal Cells N2a cells were treated concomitantly with $A\beta_{25-35}$ and memantine for 30 min. Cells were extracted and the levels of phosphorylated SAPK/JNK were determined by a specific ELISA kit. The results are the mean±SEM of one experiment (n=2). Results are shown in FIG. 46. Results show that Memantine down-regulates the $A\beta_{25-35}$-induced phosphorylation of SAPK/JNK in N2a neuronal cells.

Example 47

Memantine Down-Regulates the $A\beta_{25-35}$-Induced Phosphorylation of MEK1 in N2a Neuronal Cells without Affecting the Levels of Total MEK1

Figure 47:
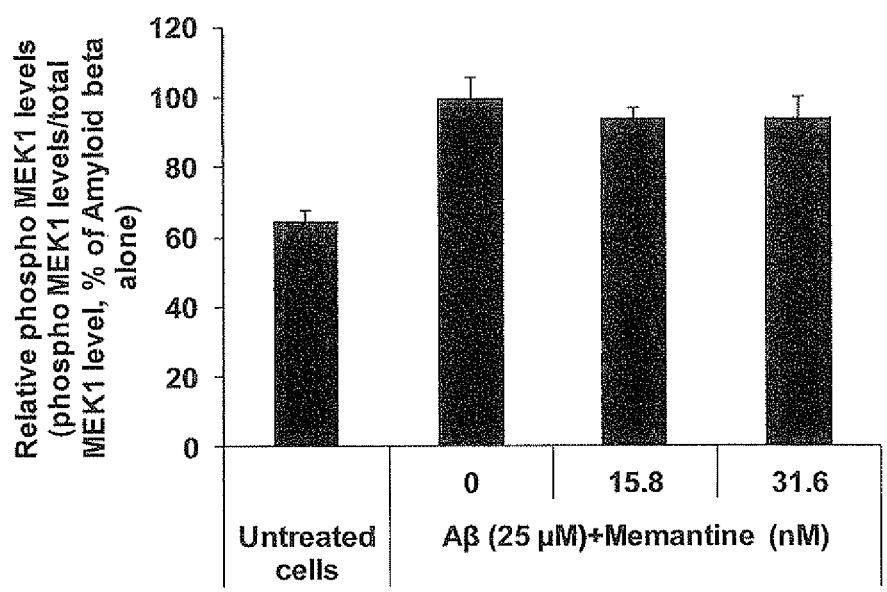
FIG. 47 shows that memantine down-regulates the $A\beta_{25\text{-}35}$-induced phosphorylation of MEK1 in N2a neuronal cells without affecting the levels of total MEK1.

N2a cells were treated concomitantly with $A_{25-35}$ and memantine for 30 min. Cells were extracted and the levels of phosphorylated or total MEK1 were determined by specific ELISA kits. The results are the mean±SEM of one experiment (n=2). Results are shown in FIG. 47. Results show that Memantine down-regulates the $A\beta_{25-35}$-induced phosphorylation of MEK1 in N2a neuronal cells without affecting the levels of total MEK1.

All patents, patent publications, and non-patent publications cited in the present application are incorporated by reference herein.

What is claimed is:

1. A method for treating a mammal suffering from a neurodegenerative condition which involves $H_2O_2$-induced death of astrocytes, the method comprising:
   providing a composition comprising purified 3,5,4'-trihydroxy-6,7,3'-trimethoxyflavone (TTF); and,
   administrating said composition to said mammal, wherein administration of the composition reduces $H_2O_2$-induced death of astrocytes, thereby treating the neurodegenerative condition.

2. The method of claim 1, wherein said neurodegenerative condition is selected from the group consisting of Alzheimer's disease, Parkinson's disease, Amyotrophic Lateral Sclerosis (ALS), ischemia, immunodeficiency virus-1 (HIV-1)-associated dementia, Lewy body associated associated dementia, traumatic brain injury (TBI), glioma, glaucoma and epilepsy.

3. The method of claim 1, wherein said TTF is administered in a form selected from the group consisting of a drug, food, medicinal food, food additive and beverage.

* * * * *